(12) United States Patent
Kubo et al.

(10) Patent No.: US 7,473,695 B2
(45) Date of Patent: Jan. 6, 2009

(54) 4-IMIDAZOLIN-2-ONE COMPOUNDS

(75) Inventors: Akira Kubo, Osaka (JP); Ritsuo Imashiro, Takatsuki (JP); Hiroaki Sakurai, Toyama (JP); Hidetaka Miyoshi, Osaka (JP); Akihito Ogasawara, Toda (JP); Hajime Hiramatsu, Ibaraki (JP); Tatsuo Nakajima, Kawachinagano (JP); Tetsu Nakane, Amagasaki (JP)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 602 days.

(21) Appl. No.: 10/827,294

(22) Filed: Apr. 20, 2004

(65) Prior Publication Data

US 2004/0204426 A1 Oct. 14, 2004

Related U.S. Application Data

(63) Continuation-in-part of application No. PCT/JP02/10937, filed on Oct. 22, 2002.

(30) Foreign Application Priority Data

| Oct. 22, 2001 | (JP) | ............................. 2001-324029 |
| Sep. 10, 2002 | (JP) | ............................. 2002-263680 |
| Apr. 21, 2003 | (JP) | ............................. 2003-116076 |

(51) Int. Cl.
*C07D 403/04* (2006.01)
*A61K 31/4439* (2006.01)

(52) U.S. Cl. .................. 514/274; 514/275; 544/315; 544/316; 544/330; 544/331; 544/332

(58) Field of Classification Search .............. 544/315, 544/316, 330, 331, 332; 514/274, 275
See application file for complete search history.

(56) References Cited

U.S. PATENT DOCUMENTS

| 3,538,104 | A | 11/1970 | Gruenfeld |
| 4,532,250 | A | 7/1985 | Stout et al. |
| 6,329,526 | B1 | 12/2001 | Adams et al. |
| 6,566,357 | B1 | 5/2003 | Laufersweiler et al. |
| 6,579,874 | B2 | 6/2003 | Revesz et al. |
| 6,677,337 | B2 | 1/2004 | Laufersweiler et al. |
| 6,730,668 | B2 | 5/2004 | Clark et al. |
| 2003/0105084 | A1 | 6/2003 | Clark et al. |

FOREIGN PATENT DOCUMENTS

| EP | 1180518 A1 | 2/2002 |
| EP | 1205478 A1 | 5/2002 |
| JP | 10-291982 A | 4/1998 |
| WO | WO 02/076974 A2 | 10/2002 |
| WO | WO 03/035638 | * 5/2003 |

OTHER PUBLICATIONS

Kubo et al., CAPLUS Abstract 138:353990, 2003.*

Damasio, Alzheimer's Disease and related dementias, Cecil Textbook of Medicine, 20th Edition, vol. 2, pp. 1992-1996, 1996.*
Simone, Oncology: Introduction, Cecil Terxtbook of Medicine, 20th Edition, vol. 1, pp. 1004-1010, 1996.*
Robert W. Carling, et al., "1-(3-Cyanobenzylpiperidin-4-yl)-5-methyl-4-phenyl-1,3-dihydroimidazol-2-one: A Selective High-Affinity Antagonist for the Human Dopamine $D_4$ Receptor with Excellent Selectivity over Ion Channels", *J. Med. Chem.* 1999, 42, 2706-2715.
Winton D. Jones, Jr., et al., "The Synthesis and Biological Activity of Pyridyl-2(3H)-Oxazolones", *Proceedings*: NOBCChe '94, vol. 21, Aug. 1994, 100-115.
Jeffrey C. Boehm & Jerry L. Adams, Expert Opinion on Therapeutic Patents, "New inhibitors of p38 kinase", *Ashley Publications Ltd.*, ISSN 1354-3776 (2000), 25-37.
Stephen E. deLaszlo et al., "Pyrroles and Other Heterocycles as Inhibitors of P38 Kinase", *Bioorganic & Medicinal Chemistry Letters 8* (1998) 2689-2694.

* cited by examiner

*Primary Examiner*—Deepak Rao
(74) *Attorney, Agent, or Firm*—Birch, Stewart, Kolasch & Birch, LLP

(57) ABSTRACT

The present invention relates to a compound of the formula [I]:

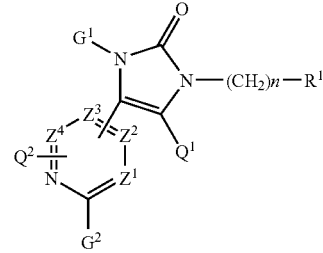

wherein $G^1$ is an alkyl which is substituted by a halogen atom or an alkoxy, or a group of the formula:

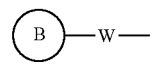

wherein ring B is benzene ring which may be substituted, etc.,
$Q^1$ and $Q^2$ maybe the same or different, and each is hydrogen atom, a halogen atom or an alkyl,
n is 0, 1, 2, 3 or 4,
$R^1$ is hydrogen atom, an alkyl which may be substituted, a cycloalkyl which may be substituted, a phenyl which may be substituted, etc.,
$Z^1$, $Z^2$, $Z^3$ and $Z^4$ may be the same or different, and each is CH or N, provided that 3 or more of $Z^1$, $Z^2$, $Z^3$ and $Z^4$ should not be N at the same time,
$G^2$ is hydrogen atom, $-NR^3R^4$, $-OR^5$, etc., where $R^3$ to $R^8$ each is independently hydrogen atom, an alkyl which may be substituted, an alkenyl, an alkynyl, etc.,
or a pharmaceutically acceptable salt thereof.

17 Claims, No Drawings

4-IMIDAZOLIN-2-ONE COMPOUNDS

This application is a Continuation-in-Part of co-pending PCT International Application No. PCT/JP02/10937 filed on Oct. 22, 2002, which designated the United States, and on which priority is claimed under 35 U.S.C. §120, which claims priority under 35 U.S.C. §119(a) on patent application Ser. No(s). 2001-324029; 2002-263680 and 2003-116076 filed in JAPAN on Oct. 22, 2001; Sep. 10, 2002 and Apr. 21, 2003, the entire contents of which are hereby incorporated by reference.

BACKGROUND OF THE INVENTION

1. Field of the Invention

The present invention relates to a novel 4-imidazolin-2-one compound which has an excellent p38MAP kinase inhibitory action and is useful for a medicament.

2. Background Art

Mitogen-activated protein (MAP) kinase is a member of serine-threonine kinases which transfers a γ-phosphate group of adenosine triphosphate (ATP) to a hydroxy of specific serine or threonine which constitutes a protein, and is involved in various cellular responses against extracellular signals. p38 MAP kinase is an about 38 kDa protein and cloned as a homologue of MAP kinases.

p38MAP kinase is activated by inflammatory cytokines such as tumor necrosis factor a (TNF-α) and interleukin 1 (IL-1), and by stimulation caused by stress such as ultraviolet irradiation. p38 MAP kinase recognizes various transcription factors and protein kinases as a substrate. It has been clearly shown that, being activated by p38 MAP kinase, these transcription factors and protein kinases become involved in promoting transcription, post-transcriptional regulation (e.g. stabilizing mRNA and promoting protein translation) or stabilizing proteins, etc. of various proteins including inflammatory cytokines, which are involved in inflammatory reactions. From these findings, it is thought that p38 MAP kinase is critically involved in the various inflammatory reactions by regulating the production and the signal transduction of inflammatory cytokines, and an inhibitor of p38 MAP kinase can highly expected to serve as a therapeutic agent for various diseases including inflammatory diseases.

As the inhibitors for p38 MAP kinase, there have been disclosed imidazole derivatives in PCT Japanese Provisional Patent Publication No.2000-503304, 1,3-thiazole derivatives in Japanese Provisional Patent Publication No. 2001-114690, 1,3-thiazole derivatives and 1,3-oxazole derivatives in Japanese Provisional Patent Publication No. 2001-114779, imidazole derivatives, pyrrole derivatives, furan derivatives, 3-pyrazolin-5-one derivatives, pyrazole derivatives and thiophene derivative, etc. in Expert Opinion on Therapeutic Patents (2000) 10(1) :25-37, respectively. However, there has been no description on 4-imidazolin-2-one derivatives in any of these.

An object of the present invention is to provide a novel compound having an excellent p38 MAP kinase inhibitory action and is useful as a pharmaceutical.

SUMMARY OF THE INVENTION

The present inventions are as disclosed as follows.

[1] A compound of the formula [I]:

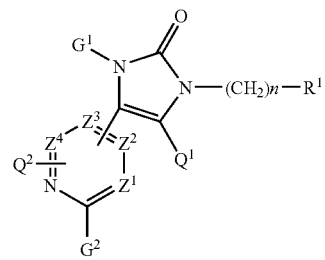

[I]

wherein $G^1$ is an alkyl which is substituted by a halogen atom or an alkoxy, or a group of the formula:

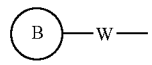

wherein ring B is benzene ring, naphthalene ring, a monocyclic or bicyclic aromatic heterocycle or a cycloalkane, and the benzene ring, the naphthalene ring, the monocyclic or bicyclic aromatic heterocycle and the cycloalkane may be substituted by 1 to 3 substituent(s), which is (are) the same or different, and selected from the group consisting of a halogen atom, nitro, an optionally substituted alkyl, an optionally substituted alkoxy, an optionally substituted amino, an optionally substituted carbamoyl, hydroxy and cyano, W is a single bond, or a $c_1$-$c_4$ alkylene which may be substituted by 1 or 2 alkyl(s), $Q^1$ and $Q^2$ maybe the same or different, and each is hydrogen atom, a halogen atom or an alkyl, n is 0, 1, 2, 3 or 4, $R^1$ is hydrogen atom, an optionally substituted alkyl, an optionally substituted cycloalkyl, an optionally substituted phenyl or an optionally substituted heterocyclic group, $Z^1$, $Z^2$, $Z^3$ and $Z^4$ may be the same or different, and each is CH or N, provided that 3 or more of $Z^1$, $Z^2$, $z^3$ and $Z^4$ should not be N at the same time, $G^2$ is hydrogen atom, —$NR^3R^4$, —$OR^5$, —$SR^5$ —$COR^6$, —$CHR^7R^8$, or a heterocyclic group, where $R^3$ to $R^8$ each independently is hydrogen atom, an optionally substituted alkyl, an alkenyl, an alkynyl, hydroxy, an alkoxy, an optionally substituted amino, an optionally substituted alkanoyl, an optionally substituted carbamoyl, an alkoxyoxalyl, an alkylsulfonyl, an optionally substituted cycloalkyl, an optionally substituted phenyl, an optionally substituted heterocyclic group, a carbonyl substituted by an optionally substituted cycloalkyl, a carbonyl substituted by an optionally substituted phenyl or a carbonyl substituted by an optionally substituted heterocyclic group, or a pharmaceutically acceptable salt thereof.

[2] A compound of the formula [Ia]:

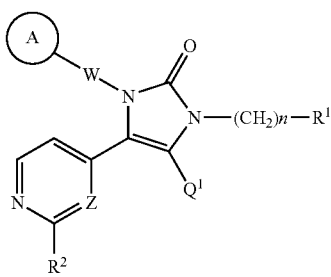

wherein ring A is benzene ring or a monocyclic aromatic heterocycle, and the benzene ring and the monocyclic aromatic heterocycle may be substituted by 1 to 3 substituent(s), which is (are) the same or different, and selected from the group consisting of a halogen atom, nitro, an optionally substituted alkyl, an optionally substituted alkoxy, an optionally substituted amino, an optionally substituted carbamoyl, hydroxy and cyano,
$Q^1$ is hydrogen atom, a halogen atom or an alkyl, W is a single bond, or a $c_1$-$c_4$ alkylene which may be substituted by 1 or 2 alkyl(s),
n is 0, 1, 2, 3 or 4,
$R^1$ is hydrogen atom, an optionally substituted alkyl, an optionally substituted cycloalkyl, an optionally substituted phenyl or an optionally substituted heterocyclic group,
Z is CH or N,
$R^2$ is hydrogen atom, $—NR^3R^4$, $—OR^5$, $—COR$ or $—CHR^7R^8$,
where $R^3$ to $R^8$, each independently is hydrogen atom, an optionally substituted alkyl, an alkenyl, an alkynyl, hydroxy, an alkoxy, an optionally substituted amino, an optionally substituted alkanoyl, an optionally substituted carbamoyl, an alkoxyoxalyl, an alkylsulfonyl, an optionally substituted cycloalkyl, an optionally substituted phenyl, an optionally substituted heterocyclic group, a carbonyl substituted by an optionally substituted cycloalkyl, a carbonyl substituted by an optionally substituted phenyl or a carbonyl substituted by an optionally substituted heterocyclic group, or a: pharmaceutically acceptable salt thereof.
[3] The compound according to [2], wherein $Q^1$ is hydrogen atom, or a pharmaceutically acceptable salt thereof.
[4] The compound according to [2] or [3], wherein the ring A is a benzene ring which may be substituted by 1 to 3 substituent(s), which is(are) the same or different, and selected from the group consisting of a halogen atom, nitro, an optionally substituted alkyl, an optionally substituted alkoxy, an optionally substituted amino and cyano, and W is a single bond, or a pharmaceutically acceptable salt thereof.
[5] The compound according to any one of [2] to [4], wherein n is 0 or 1, or a pharmaceutically acceptable salt thereof
[6] The compound according to any one of [2] to [4], wherein (1) n is 0 and $R^1$ is an optionally substituted alkyl, (2) n is 1 and $R^1$ is an optionally substituted cycloalkyl, (3) n is 1 and $R^1$ is an optionally substituted phenyl, (4) n is 1 and $R^1$ is an optionally substituted heterocyclic group, (5) n is 0 and $R^1$ is an optionally substituted cycloalkyl, and (6) n is 0 and $R^1$ is an optionally substituted heterocyclic group, or a pharmaceutically acceptable salt thereof.

[7] The compound according to any one of [2] to [6], wherein $R^2$ is $—NR^3R^4$ or $—OR^5$, or a pharmaceutically acceptable salt thereof.
[8] The compound according to any one of [2] to [7], wherein $R^2$ is $—NHR^4$, and $R^4$ is an optionally substituted alkyl, an alkenyl, an optionally substituted alkanoyl, an optionally substituted carbamoyl, an optionally substituted cycloalkyl, an optionally substituted phenyl, an optionally substituted heterocyclic group, a carbonyl substituted by an optionally substituted cycloalkyl or a carbonyl substituted by an optionally substituted heterocyclic group, or a pharmaceutically acceptable salt thereof.
[9] The compound according to [3], wherein the ring A is a benzene ring which may be substituted by 1 or 2 substituent(s), which is (are) the same or different, and selected from the group consisting of a halogen atom, an optionally substituted alkyl, an optionally substituted alkoxy, an optionally substituted amino and cyano,
W is a single bond,
n is 0 or 1,
$R^1$ is hydrogen atom, an optionally substituted alkyl, an optionally substituted cycloalkyl, an optionally substituted phenyl or an optionally substituted heterocyclic group,
Z is CH or N,
$R^2$ is hydrogen atom, $—NR^3R^4$, $—OR^5$, $—COR^1$ or $—CHR^7R^8$,
Where $R^3$ to $R^8$ each independently is hydrogen atom, an optionally substituted alkyl, an alkenyl, an alkoxy, an optionally substituted alkanoyl, an optionally substituted carbamoyl, an alkoxyoxalyl, an optionally substituted cycloalkyl, an optionally substituted phenyl, an optionally substituted heterocyclic group, a carbonyl substituted by an optionally substituted cycloalkyl or a carbonyl substituted by an optionally substituted heterocyclic group, or a pharmaceutically acceptable salt thereof.
[10] The compound according to [3], wherein the ring A is a benzene ring which may be substituted by 1 or 2 substituent(s), which is (are) the same or different, and selected from the group consisting of a halogen atom, an alkyl optionally substituted by halogen(s), an alkoxy, an amino optionally substituted by alkyl(s) and cyano,
W is a single bond,
n is 0 or 1,
$R^1$ is
(1) hydrogen atom,
(2) an alkyl optionally substituted by group(s) selected from the group consisting of phenyl, an alkoxy, an alkylamino, a dialkylamino, an alkanoylamino, an alkylsulfonylamino, a carbamoyl optionally substituted by alkyl(s), hydroxy, carboxy and cyano,
(3) a cycloalkyl optionally substituted by group(s) selected from the group consisting of the following (i) to (v):
  (i) hydroxy,
  (ii) an alkoxy optionally substituted by alkoxy(s),
  (iii) an amino optionally substituted by group(s) selected from the group consisting of an alkyl, an alkanoyl and an alkylsulfonyl,
  (iv) a carbamoyl optionally substituted by alkyl(s), and
  (v) an alkyl optionally substituted by group(s) selected from the group consisting of hydroxy, an alkoxy and amino, (4) a phenyl optionally substituted by group(s) selected from the group consisting of the following (i) to (vi):
  (i) a halogen atom,
  (ii) an alkyl optionally substituted by group(s) selected from the group consisting of a halogen atom, hydroxy and phenylsulfonyl,
  (iii) cyano,
  (iv) an alkoxy,
  (v) an amino optionally substituted by group(s) selected from the group consisting of an alkyl and, an alkylsulfonyl,
  (vi) a carbonyl substituted by a heterocyclic group, or
(5) a heterocyclic group optionally substituted by group(s) selected from the group consisting of the following (i) to (iv):
  (i) an alkoxycarbonyl,
  (ii) an alkyl optionally substituted by group(s) selected from the group consisting of hydroxy, an alkoxy and a carbamoyl optionally substituted by alkyl(s),
  (iii) an alkanoyl and
  (iv) an alkylsulfonyl,
Z is CH or N,
$R^2$ is hydrogen atom, $-NR^3R^4$, $-OR^5$, $-COR^6$ or $-CHR^7R^8$,
where $R^3$ to $R^8$ each independently is:
(1) hydrogen atom,
(2) an alkyl optionally substituted by group(s) selected from the group consisting of the following (i) to (vii):
  (i) hydroxy,
  (ii) an alkoxy,
  (iii) an amino optionally substituted by group(s) selected from the group consisting of an alkyl, an alkanoyl and an alkylsulfonyl,
  (iv) an alkoxycarbonyl,
  (v) a cycloalkyl optionally substituted by group(s) selected from the group consisting of the following a) to g):
    a) hydroxy,
    b) an amino optionally substituted by alkyl(s),
    c) an alkanoylamino,
    d) an alkylsulfonylamino,
    e) an alkyl optioinally substituted by group(s) selected from the group consisting of hydroxy, an alkoxy, amino, a carbamoyl optionally substituted by alkyl(s),
    f) carboxy and
    g) a carbamoyl optionally substituted by alkyl (3),
  (vi) a phenyl optionally substituted by group(s) selected from the group consisting of a halogen atom, an alkoxy and morpholinylcarbonyl, and
  (vii) a heterocyclic group optionally substituted by alkyl(s),
(3) an alkenyl,
(4) an alkoxy,
(5) an alkanoyl optionally substituted by group(s) selected from the group consisting of the following (i) to (iv):
  (i) hydroxy,
  (ii) an alkoxy,
  (iii) an amino optionally substituted by group(s) selected from the group consisting of an alkyl and an alkanoyl,
  (iv) an alkoxycarbonyl,
(6) a carbamoyl optionally substituted by alkyl(s),
(7) an alkoxyoxalyl,
(8) a cycloalkyl optionally substituted by group(s) selected from the group consisting of the following (i) to (vii):
  (i) a halogen atom,
  (ii) hydroxy,
  (iii) an alkoxy,
  (iv) an amino optionally substituted by group(s) selected from the group consisting of an alkyl, an alkanoyl, an alkoxycarbonyl and an alkylsulfonyl,
  (v) an alkyl optionally substituted by group(s) selected from the group consisting of hydroxy, an alkoxy, amino, a carbamoyl optionally substituted by alkyl(s),
  (vi) an alkanoyloxy and
  (vii) a carbamoyl optionally substituted by alkyl(s),
(9) a phenyl optionally substituted by group(s) selected from the group consisting of a halogen atom and an alkoxy,
(10) a heterocyclic group optionally substituted by group(s) selected from the group consisting of the following (i) to (vii):
  (i) an alkyl optionally substituted by group(s) selected from the group consisting of phenyl, hydroxy, an alkoxy, amino and a carbamoyl optionally substituted by alkyl(s),
  (ii) an alkoxycarbonyl,
  (iii) an alkanoyl,
  (iv) an alkylsulfonyl,
  (v) oxo,
  (vi) a carbamoyl optionally substituted by alkyl(s),
  (vii) an aminosulfonyl optionally substituted by alkyl(s),
(11) a carbonyl substituted by a cycloalkyl optionally substituted by group(s) selected from the group consisting of hydroxy, amino and an alkanoylamino, or
(12) a heterocyclic group-substituted carbonyl, or a pharmaceutically acceptable salt thereof.

[11] The compound according to [3], wherein the ring A is a benzene ring which may be substituted by 1 or 2 substituent(s), which is (are) the same or different, and selected from the group consisting of fluorine atom, chlorine atom, an alkyl optionally substituted by halogen(s) and an alkoxy,
W is a single bond,
n is 0 or 1,
$R^1$ is
  (1) hydrogen atom,
  (2) an alkyl optionally substituted by group(s) selected from the group consisting of phenyl, an alkoxy, an alkylamino, a dialkylamino, an alkanoylamino, an alkylsulfonylamino, a carbamoyl optionally substituted by alkyl(s), hydroxy, carboxy, cyano, and cycloalkyl,
  (3) a cycloalkyl optionally substituted by group(s) selected from the group consisting of the following (i) to (v):
    (i) hydroxy,
    (ii) an alkoxy optionally substituted by alkoxy(s),
    (iii) an amino optionally substituted by group(s) selected from the group consisting of an alkyl, an alkanoyl and an alkylsulfonyl,
    (iv) a carbamoyl optionally substituted by alkyl(s),
    (v) an alkyl optionally substituted by group(s) selected from the group consisting of hydroxy and amino,
  (4) a phenyl optionally substituted by group(s) selected from the group consisting of the following (i) to (iv):

(i) a halogen atom,
(ii) an alkyl optionally substituted by halogen atom(s),
(iii) cyano, and
(iv) an alkoxy, or
(5) a heterocyclic group optionally substituted by alkylsulfonyl or alkanoyl,
Z is CH or N,
$R^2$ is hydrogen atom, —$NR^3R^4$, —$OR^5$, or —$COR^6$,
Where $R^3$ to $R^6$ each independently is:
(1) hydrogen atom,
(2) an alkyl optionally substituted by group(s) selected from the group consisting of the following (i) to (vii):
(i) hydroxy,
(ii) an alkoxy,
(iii) an alkoxycarbonyl,
(iv) a cycloalkyl optionally substituted by group(s) selected from the group consisting of the following a) to e):
a) hydroxy,
b) an amino optionally substituted by alkyl(s),
c) an alkanoylamino,
d) an alkyl optionally substituted by group(s) selected from the group consisting of hydroxy, amino and a carbamoyl optionally substituted by alkyl(s), and
e) a carbamoyl optionally substituted by alkyl(s),
(v) a phenyl optionally substituted by alkoxy(s),
(vi) a heterocyclic group, and
(vii) an amino optionally substituted by the group(s) selected from alkanoyl(s) and alkylsulfonyl(s),
(3) an alkenyl,
(4) an alkoxy,
(5) an alkanoyl optionally substituted by group(s) selected from the group consisting of an alkoxy, an amino optionally substituted by alkanoyl(s), and an alkoxycarbonyl,
(6) a cycloalkyl optionally substituted by group(s) selected from the group consisting of the following (i) to (v):
(i) hydroxy,
(ii) an alkoxy,
(iii) an amino optionally substituted by group(s) selected from the group consisting of an alkyl, an alkanoyl, an alkoxycarbonyl and an alkylsulfonyl,
(iv) an alkyl optionally substituted by group(s) selected from the group consisting of hydroxy, amino and a carbamoyl optionally substituted by alkyl(s),
(v) a carbamoyl optionally substituted by alkyl(s),
(7) a heterocyclic group optionally substituted by group(s) selected from the group consisting of the following (i) to (vi):
(i) an alkyl optionally substituted by phenyl(s),
(ii) an alkoxycarbonyl,
(iii) an alkylsulfonyl
(iv) an alkanoyl,
(v) a carbamoyl optionally substituted by alkyl(s), and
(vi) an aminosulfonyl optionally substituted by alkyl(s),
(8) a carbonyl substituted by a cycloalkyl optionally substituted by group(s) selected from the group consisting of hydroxy and amino, or
(9) a heterocyclic group-substituted carbonyl, or a pharmaceutically acceptable salt thereof.

[12] A compound of the formula [Ib]:

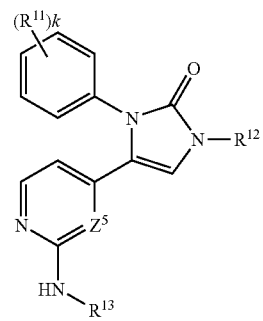

wherein $R^{11}$ is a group selected from the group consisting of hydrogen atom, a halogen atom, a $c_1$-$c_4$ alkyl optionally substituted by halogen(s) and a $c_1$-$c_4$ alkoxy,
k is 1 or 2, and when k is 2, two of $R^{11}$s may be the same or different,
$R^{12}$ is
(1) a $c_1$-$c_5$ alkyl optionally substituted by group(s) selected from the group consisting of hydroxy, an alkoxy, cyano, amino, tetrahydropyranyl, tetrahydrofuryl and a carbamoyl optionally substituted by alkyl(s),
(2) a $C_3$-$c_4$ cycloalkylmethyl,
(3) a $C_3$-$c_4$ cycloalkyl,
(4) carbamoylmethyl,
(5) a benzyl optinally substituted by group(s) selected from the group consisting of cyano, a halogen atom, a $c_1$-$c_3$ alkoxy, a $c_1$-$c_3$ alkyl and a halogen-substituted $c_1$-$c_3$ alkyl,
(6) tetrahydropyranyl,
(7) tetrahydrofuryl and
(8) a piperidyl optionally substituted by group(s) selected from the group consisting of an alkyl, an alkanoyl, an alkylsulfonyl, an alkoxycarbonyl and a carbamoylalkyl optionally substituted by alkyl(s),
$Z^5$ is CH or N,
$R^{13}$ is
(1) a $c_1$-$c_6$ alkyl optionally substituted by group(s) selected from the group consisting of the following (i) to (xiv):
(i) a $c_5$-$c_7$ cycloalkyl optionally substituted by group(s) selected from the group consisting of the following a) to e):
a) hydroxy
b) an amino optionally substituted by $c_1$-$c_4$ alkyl(s),
c) a $c_1$-$c_4$ alkanoylamino,
d) a $c_1$-$c_4$ alkyl optionally substituted by group(s) selected from the group consisting of hydroxy, amino, and a carbamoyl optionally substituted by $c_1$-$c_4$ alkyl(s), and
e) a carbamoyl optionally substituted by $c_1$-$c_4$ alkyl(s),
(ii) hydroxy,
(iii) a carbamoyl optionally substituted by $c_1$-$c_4$ alkyl(s),
(iv) a piperidyl optionally substituted by group(s) selected from the group consisting of an alkyl, an alkanoyl, an alkylsulfonyl and oxo,
(v) a pyrrolidinyl optionally substituted by group(s) selected from the group consisting of an alkyl, an alkanoyl, an alkylsulfonyl and oxo,
(vi) a tetrahydropyranyl optionally substituted by hydroxy(s), (vii) an imidazolinyl optionally substituted by group(s) selected from the group consisting of an alkyl and oxo,
(viii) an imidazolidinyl optionally substituted by group(s) selected from the group consisting of an alkyl and oxo,
(ix) a piperadinyl optionally substituted by group(s) selected from the group consisting of an alkyl and oxo,
(x) a hexahydropyrimidinyl optionally substituted by group(s) selected from the group consisting of an alkyl and oxo,
(xi) a pyridyl optionally substituted by alkyl(s),
(xii) furyl,
(xiii) tetrahydroisothiazolyl optionally substituted by oxo(s), and
(xiv) amino optionally substituted by the group(s) selected from alkanoyl(s) and alkylsulfonyl(s),
(2) a $c_5$-$c_7$ cycloalkyl optionally substituted by group(s) selected from the group consisting of the following (i) to (v):
(i) hydroxy,
(ii) a $c_1$-$c_4$ alkoxy,
(iii) a $c_1$-$c_4$ alkyl optionally substituted by group(s) selected from the group consisting of hydroxy, amino and a carbamoyl optionally substituted by $c_1$-$c_4$ alkyl(s),
(iv) a carbamoyl optionally substituted by $c_1$-$c_4$ alkyl(s), and
(v) an amino optionally substituted by group(s) selected from the group consisting of $c_1$-$c_4$ alkyl(s) and $c_1$-c4 alkylsulfonyl(s), or
(3) a heterocyclic group optionally substituted by group(s) selected from the group consisting of the following (i) to (vii):
(i) an alkyl optionally substituted by group(s) selected from the group consisting of a halogen, amino, hydroxy, phenyl and oxo,
(ii) an aminosulfonyl optionally substituted by alkyl(s),
(iii) an alkylsulfonyl optionally substituted by halogen(s),
(iv) a carbamoyl optionally substituted by alkyl(s),
(v) hydroxy,
(vi) an alkoxycarbonyl, and
(vii) oxo, or a pharmaceutically acceptable salt thereof.

[13] The compound according to [12], wherein $R^{12}$ is
(1) a $c_1$-$c_5$ alkyl optionally substituted by group(s) selected from the group consisting of hydroxy, alkoxy, tetrahydropyranyl and tetrahydrofuryl
(2) a $c_3$-$c_4$ cycloalkylmethyl,
(3) a $c_3$-$c_4$ cycloalkyl,
(4) carbamoylmethyl,
(5) a benzyl optinally substituted by group(s) selected from the group consisting of cyano, a halogen atom, a $c_1$-$c_3$ alkoxy, a $c_1$-$c_3$ alkyl and a halogen-substituted $c_1$-$c_3$ alkyl,
(6) tetrahydropyranyl,
(7) tetrahydrofuryl, or
(8) a piperidyl optionally substituted by alkylsulfonyl or alkanoyl,
$R^{13}$ is (1) a $c_1$-$c_6$ alkyl optionally substituted by group(s) selected from the group consisting of the following (i) to (iv):

(i) a $c_5$-$c_7$ cycloalkyl optionally substituted by group(s) selected from the group consisting of the following a) to e):
a) hydroxy
b) an amino optionally substituted by $c_1$-$c_4$ alkyl(s),
c) a $c_1$-$c_4$ alkanoylamino,
d) a $c_1$-c4 alkyl optionally substituted by group(s) selected from the group consisting of hydroxy, amino, and a carbamoyl optionally substituted by $c_1$-$c_4$ alkyl(s), and
e) a carbamoyl optionally substituted by $c_1$-$c_4$ alkyl(s),
(ii) hydroxy,
(iii) a carbamoyl optionally substituted by $c_1$-$c_4$ alkyl(s), and
(iv) an amino optionally substituted by the group(s) selected from alkanoyl(s) and alkylsulfonyl(s),
(2) a $c_5$-$c_7$ cycloalkyl optionally substituted by group(s) selected from the group consisting of the following (i) to (v):
(i) hydroxy,
(ii) a $c_1$-$c_4$ alkoxy,
(iii) a $c_1$-$c_4$ alkyl optionally substituted by group(s) selected from the group consisting of hydroxy, amino and a carbamoyl optionally substituted by $c_1$-$c_4$ alkyl(s),
(iv) a carbamoyl optionally substituted by $c_1$-$c_4$ alkyl(s), and
(v) an amino optionally substituted by group(s) selected from the group consisting of $c_1$-$c_4$ alkyl(s) and $c_1$-$c_4$ alkylsulfonyl(s), or
(3) a heterocyclic group optionally substituted by group(s) selected from the group consisting of the following (i) to (vi):
(i) alkylsulfonyl(s),
(ii) alkoxycarbonyl(s),
(iii) carbamoyl(s) optionally substituted by alkyl(s),
(iv) alkanoyl(s),
(v) aminosulfonyl(s) optionally substituted by alkyl(s), and
(vi) alkyl(s), or a pharmaceutically acceptable salt thereof.

[14] The compound according to [12] or [13], wherein $R^{11}$ is a group selected from the group consisting of hydrogen atom, fluorine atom, chlorine atom, methyl, trifluoromethyl and methoxy,
k is 1 or 2, and when k is 2, two of $R^{11}$s may be the same or different,
$R^{12}$ is a $c_1$-$c_5$ alkyl optionally substituted by hydroxy, cyclopropylmethyl, cyclobutyl, carbamoylmethyl, tetrahydropyranyl, tetrahydrofuryl, tetrahydropyranylmethyl, tetrahydrofurylmethyl or piperidyl optionally substituted by the group selected from alkylsulfonyl and alkanoyl, or a pharmaceutically acceptable salt thereof.

[15] The compound according to [12] or [13], wherein $R^{11}$ is hydrogen atom, fluorine atom, chlorine atom, trifluoromethyl or methyl,
k is 1,
$R^{12}$ is ethyl, isopropyl, isobutyl, 2-hydroxy-2-methylpropyl, cyclopropylmethyl, cyclobutyl, carbamoylmethyl, 4-tetrahydropyranyl, 3-tetrahydrofuryl, tetrahydropyranylmethyl, tetrahydrofurylmethyl methoxymethyl, 3-hydroxy-3-methylbutyl or 4-piperidyl substituted by methanesulfonyl or acetyl, $R^{13}$ is (1) a $c_1$-$c_6$ alkyl optionally substituted by group(s) selected from the group consisting of the following (i) and (iii):
  (i) a $c_5$-$c_7$ cycloalkyl optionally substituted by group(s) selected from the group consisting of hydroxy, a $c_1$-$c_4$ alkyl, a hydroxy $c_1$-$c_4$ alkyl, an amino optionally substituted by $c_1$-$c_4$ alkyl(s) and a carbamoyl optionally substituted by $c_1$-$c_4$ alkyl(s),
  (ii) hydroxy, and
  (iii) an amino optionally substituted by group(s) selected from the group consisting of alkyl(s) and alkylsulfonyl(s), (2) a $c_5$-$c_7$ cycloalkyl optionally substituted by group(s) selected from the group consisting of the following (i) to (v):
  (i) hydroxy,
  (ii) a $c_1$-$c_4$ alkoxy,
  (iii) a $c_1$-$c_4$ alkyl optionally substituted by group(s) selected from the group consisting of hydroxy, amino and a carbamoyl optionally substituted by $c_1$-$c_4$ alkyl(s),
  (iv) a carbamoyl optionally substituted by $c_1$-$c_4$ alkyl(s), and
  (v) an amino optionally substituted by group(s) selected from the group consisting of alkyl(s) and alkylsulfonyl(s), (3) piperidinyl optionally substituted by group(s) selected from the group consisting of the following (i) to (vi):
  (i) alkylsulfonyl(s),
  (ii) alkoxycarbonyl(s),
  (iii) carbamoyl(s) optionally substituted by alkyl(s),
  (iv) alkanoyl(s),
  (v) aminosulfonyl(s) optionally substituted by alkyl(s), and
  (vi) alkyl(s), (4) pirrolidinyl optionally substituted by alkylsulfonyl, or a pharmaceutically acceptable salt thereof.

[16] A pharmaceutical composition comprising the compound according to any one of [1] to [15] or a pharmaceutically acceptable salt thereof and a pharmaceutically acceptable carrier.

[17] The method of inhibiting of p38 MAP kinase which comprises administering the compound according to any one of [1] to [15] or a pharmaceutically acceptable salt thereof to a human in need thereof.

[18] The method of prophylaxis or treatment for diseases related to the activation of p38 MAP kinase or the excessive production of inflammatory mediators concerned with p38 MAP kinase, which comprises administering the compound according to any one of [1] to [15] or a pharmaceutically acceptable salt thereof to a human in need thereof.

[19] The method of prophylaxis or treatment for diseases selected from the group consisting of arthritis, inflammatory bowel disease, inflammatory dermal disease, inflammatory respiratory disease, inflammatory optical disease, nephritis, hepatitis, systemic inflammatory disease, shock, cerebrovascular disease, ischemic cardiac diseases, osteoporosis, multiple sclerosis, diabetes, malignant tumor, cachexia, Alzheimer's disease, Parkinson's disease, acquired immunodeficiency syndrome, arterial sclerosis, disseminated intravascular coagulation syndrome, rejection and graft-versus-host diseases by organ transplantation, which comprises administering the compound according to any one of [1] to [15] or a pharmaceutically acceptable salt thereof to a human in need thereof.

DETAILED DESCRIPTION OF THE INVENTION

In the present invention, "an alkyl" and alkyls in "an alkylthio", "an alkylsulfinyl" and "an alkylsulfonyl" are exemplified by a straight or branched chain $c_1$-$c_6$ alkyl, and specifically, methyl, ethyl, propyl, isopropyl, butyl, isobutyl, pentyl, hexyl, etc. Preferred is a $c_1$-$c_4$ alkyl.

"An alkoxy" and alkoxys in "an alkoxycarbonyl" and "an alkoxyoxalyl" are exemplified by a straight and branched chain $c_1$-$c_6$ alkoxy, and specifically, methoxy, ethoxy, propoxy, isopropoxy, butoxy, isobutoxy, pentoxy, hexoxy, etc. Preferred is a $c_1$-$c_4$ alkoxy.

"An alkenyl" is exemplified by a straight or branched chain $c_2$-$c_7$ alkenyl, and specifically, vinyl, allyl, 3-butenyl, 2-pentenyl, 3-hexenyl, etc. Preferred is a $c_2$-$c_5$ alkenyl, etc.

"An alkynyl" is exemplified by a straight or branched chain $c_2$-$c_7$ alkynyl, and specifically, ethynyl, propargyl, 3-butynyl, 2-pentynyl, 3-hexynyl, etc. Preferred is a $c_2$-$c_5$ alkynyl.

"An alkanoyl" is exemplified by a straight or branched chain $c_2$-$c_7$ alkanoyl, and specifically, acetyl, propionyl, butyryl, isobutyryl, pentanoyl, hexanoyl, etc. Preferred is a $c_2$-$c_5$ alkanoyl.

"A cycloalkyl" is exemplified by a $c_3$-$c_8$ cycloalkyl, and preferred is a $c_3$-$c_6$ cycloalkyl.

"A cycloalkane" is exemplified by a $c_3$-$c_8$ cycloalkane, and preferred is a $c_5$-$c_7$ cycloalkane.

"A halogen atom" is exemplified by fluorine atom, chlorine atom, bromine atom, iodine atom, and preferred are fluorine atom and chlorine atom.

"A heterocyclic group" is exemplified by a monocyclic, bicyclic or tricyclic heterocyclic group containing 1 to 3 heteroatoms selected from nitrogen atom, oxygen atom, and sulfur atom, a part or whole portion of which may be saturated. Preferred is a 5- or 6-membered monocyclic heterocyclic group, and specific examples are furyl, tetrahydrofuryl, tetrahydropyranyl, tetrahydrothiapyranyl, thienyl, tetrahydrothienyl, thiazolyl, isothiazolyl, tetrahydroisothiazolyl, oxazolyl, isoxazolyl, oxadiazolyl, tetrazolyl, pyrrolyl, pyrrolidinyl, pyrrolinyl, imidazolidinyl, imidazolinyl, pyrazolidinyl, pyridyl, pyridazinyl, pyrimidinyl, hexahydropyrimidinyl, pyrazinyl, triazinyl, piperidinyl, pyrazolyl, piperazinyl, morpholinyl, dioxanyl, imidazolyl, triazolyl, imidazolinyl, pyrazolinyl, thiazinyl, tetrahydrothiazinyl, etc.

"A monocyclic or bicyclic aromatic heterocycle" is exemplified by a monocyclic or bicyclic aromatic heterocycle containing 1 to 3 heteroatoms selected from nitrogen atom, oxygen atom, and sulfur atom. Additionally, "monocyclic aromatic heterocycle" is exemplified by a monocyclic aromatic heterocycle containing 1 to 3 heteroatoms selected from nitrogen atom, oxygen atom, and sulfur atom, for example, 5- or 6-membered monocyclic aromatic heterocycle. Specific examples for the monocyclic and bicyclic aromatic heterocycle include thiophene, furan, furazane, pyrrole, imidazole, pyrazole, thiazole, isothiazole, oxazole, isoxazole, oxadiazole, pyridine, pyridazine, pyrimidine, pyrazine, triazine, quinazoline, isoquinoline, phthalazine, naphthyridine, quinazoline, quinoline, chromene, indolizine, isoindole, indole, purine, benzofuran, benzothiophene, etc. Preferred monocyclic aromatic heterocycles are thiophene, furan, etc.

When a substituent of the ring B in the compound [I] or a substituent of the ring A in the compound [Ia] is "an optionally substituted alkyl", examples for substituent of the alkyl include a halogen atom, hydroxy, amino, etc. The said alkyl may have 1 to 3 substituents mentioned above, and when the number of the substituents is two or more, each of the substituents may be the same or different. Specific examples for the substituted alkyl include hydroxymethyl, trifluoromethyl, aminomethyl, chloroethyl, etc.

When a substituent of the ring B or a substituent of the ring A is "an optionally substituted alkoxy", examples for substituent of the alkoxy include hydroxy, amino, etc. The said alkoxy may have 1 to 3 substituents mentioned above, and when the number of the substituents is two or more, each of the substituents may be the same or different.

When a substituent of the ring B or a substituent of the ring A is "an optionally substituted amino", examples for the substituent of the amino include an alkyl (said alkyl may be substituted with 1 to 3 groups which are the same or different, selected from the group consisting of an alkoxy, amino and carboxy), an alkanoyl, etc. The said amino may have 1 or 2 substituents mentioned above, and when the number of the substituents is two, each of the substituents may be the same or different.

When a substituent of the ring B or a substituent of the ring A is "an optionally substituted carbamoyl", examples for the substituents of the carbamoyl include alkyl, etc. The said carbamoyl may have 1 or 2 substituents mentioned above, and when the number of the substituents is two, each of the substituents may be the same or different.

A substituent of the ring B in the compound [I] or a substituent of the ring A in the compound [Ia] is preferably exemplified by a halogen atom, nitro, an optionally substituted alkyl, an optionally substituted alkoxy, an optionally substituted amino, and cyano. Particularly preferred are a halogen atom, a $c_1$-$c_4$alkyl, a $c_1$-$c_4$alkoxy, etc., and specific examples are fluorine atom, chlorine atom, methyl, methoxy, etc.

When $R^1$ of the compound [I] and the compound [Ia] is "an optionally substituted alkyl", examples for substituent of the alkyl include analkynyl, cyano, analkoxy, hydroxy, amino (said amino may be substituted with 1 or 2 substituents selected from the group consisting of an alkyl, an alkanoyl, and an alkylsulfonyl.), carboxy, an alkoxycarbonyl, carbamoyl (said carbamoyl may be substituted with 1 or 2 alkyl(s).), phenyl, naphthyl, etc. The said alkyl may have 1 to 3 substituents mentioned above, and when the number of the substituents is two or more, each of the substituents may be the same or different. Specific examples for the substituents include cyano, an alkoxy, hydroxy, amino, carboxy, a carbamoyl which may be substituted by an alkyl, phenyl, etc.

When $R^1$ is "an optionally substituted cycloalkyl", examples for the substituents of the cycloalkyl include (1) hydroxy, (2) an alkoxy (said alkoxy may be substituted by 1 to 3 alkoxy(s)), (3) amino [said amino may be substituted by 1 or 2 group(s), being the same or different, and selected from the group consisting of the following (i) to (v) : (i) an alkyl, (ii) an alkanoyl, (iii) an alkoxycarbonyl, (iv) carbamoyl (said carbamoyl may be substituted by 1 or 2 alkyl(s).), and(v) an alkylsulfonyl), (4) carboxy, (5) an alkyl (said alkyl may be substituted by a group selected form the group consisting of hydroxy, an alkoxy and amino), (6) a carbamoyl which may be substituted by alkyl(s), etc. The said cycloalkyl may have 1 to 3 substituents mentioned above, and when the number of the substituents is two or more, each of the substituents may be the same or different.

When $R^1$ is "an optionally substituted phenyl", examples for the substituents of the phenyl include (1) a halogen atom, (2) nitro, (3) an alkyl (said alkyl may be substituted by 1 to 3 group(s), being the same or different, selected from the group consisting of a halogen atom, hydroxy, amino, carboxy, and phenylsulfonyl), (4) an alkenyl, (5) cyano, (6) hydroxy, (7) an alkoxy (said alkoxy may be substituted by 1 to 3 group(s), being the same or different, and selected from the group consisting of a halogen atom, carboxy, an alkoxycarbonyl, carbamoyl, phenyl and morpholinylcarbonyl), (8) amino [said amino may be substituted with 1 or 2 group(s), being the same or different, and selected from the group consisting of the following (i) to (iv) : (i) an alkyl, (ii) an alkanoyl, (iii) carbamoyl (said carbamoyl may be substituted by 1 or 2 group(s), being the same or different, and selected from the group consisting of an alkyl and a cycloalkyl), and (iv) an alkylsulfonyl], (9) an alkanoyl, (10) carboxy, (11) an alkoxycarbonyl, (12)carbamoyl [said carbamoyl may be substituted by 1 or 2 group(s), being the same or different, and selected from the group consisting of the following (i) and (ii): (i) an alkyl (said alkyl may be substituted by 1 to 3 hydroxy(s)) and (ii) a cycloalkyl], (13) an alkylthio, (14) an alkylsulfinyl, (15) an alkylsulfonyl, (16) phenyl, (17) tetrazolyl, (18) a heterocyclic group-substituted carbonyl (said heterocyclic group may be substituted by 1 to 3 group(s), being the same or different, and selected from the group consisting of an alkyl and an alkoxycarbonyl), etc. When $R^1$ is an optionally substituted phenyl, said phenyl may have 1 to 3 substituent(s) mentioned above, and when the number of the substituents is 2 or more, each of the substituents may be the same or different. Preferred substituents are (1) a halogen atom, (2) an alkyl (said alkyl may be substituted by 1 to 3 group(s), being the same or different, and selected from the group consisting of a halogen atom, hydroxy, amino, carboxy, and phenylsulfonyl), (3) cyano, (4) an alkoxy (said alkoxy may be substituted by 1 to 3 group(s), being the same or different, and selected from the group consisting of a halogen atom, carboxy, an alkoxycarbonyl, carbamoyl, phenyl and morpholinyl carbonyl), etc. There is no limitation regarding positions of the substituents, as long as it is possible to substitute, and a particularly preferred position is 2-position.

When $R^1$ is "a phenyl substituted by a heterocyclic group-substituted carbonyl", examples for the heterocyclic group include the above-mentioned heterocyclic groups, and preferred are 5- or 6-membered monocyclic nitrogen-containing aliphatic heterocyclic groups. Specific examples are pyrrolidinyl, piperidyl, piperazinyl, morpholinyl, etc.

When R is "an optionally substituted heterocyclic group", examples for the heterocyclic group include the above-mentioned heterocyclic groups, and preferred are 5- or 6-membered monocyclic heterocyclic groups. Specific examples are furyl, tetrahydrofuryl, thienyl, thiazolyl, isoxazolyl, oxadiazolyl, pyridyl, pyrimidinyl, pyrazinyl, piperidinyl, pyrrolidinyl, pyrazolyl, tetrazolyl, tetrahydropyranyl, etc. Particularly preferred are piperidinyl, tetrahydropyranyl, etc. Further, the substituents of the heterocyclic group are exemplified by a halogen atom, nitro, an alkyl (said alkyl may be substituted by a group selected from the group consisting of hydroxy, an alkoxy, a carbamoyl which may be substituted by alkyl(s) and carboxy(s)), cyano, hydroxy, amino, an alkanoyl, carboxy, an alkoxycarbonyl, carbamoyl (said carbamoyl may be substituted by 1 or 2 alkyl(s)), an alkylsulfonyl, phenyl, etc. The said heterocyclic group may have 1 to 3 substituent(s) mentioned above, and when the number of the substituents is 2 or more, each of the substituents may be the same or different.

A preferred combination of n and $R^1$ in the compound [I] and the compound [Ia] are exemplified by (1) those in which n is 0 and $R^1$ is an optionally substituted alkyl, (2) those in which n is 1 and $R^1$ is an optionally substituted cycloalkyl, (3) those in which n is 1 and $R^1$ is an optionally substituted phenyl, (4) those in which n is 1 and $R^1$ is an optionally substituted heterocyclic group, (5) those in which n is 0 and $R^1$ is an optionally substituted cycloalkyl, and (6) those in which n is 0 and $R^1$ is an optionally substituted heterocyclic group, etc. Particularly preferred are (1) those in which n is 0 and $R^1$ is an optionally substituted alkyl, (2) those in which n is 1 and $R^1$ is an optionally substituted phenyl, (3) those in which n is 0 and $R^1$ is an optionally substituted cycloalkyl, and (4) those in which n is 0 and $R^1$ is an optionally substituted heterocyclic group, etc. Further preferred are (1) those in which n is 0 and $R^1$ is a $c_1$-$c_4$ alkyl optionally substituted by hydroxy, (2) those in which n is 1 and $R^1$ is a phenyl (said phenyl may be substituted by a group selected from the group consisting of cyano, fluorine atom, chlorine atom and methyl), (3) those in which n is 0 and $R^1$ is $c_3$-$c_4$ cycloalkyl, and (4) those in which n is 0 and $R^1$ is 4-tetrahydropyranyl, etc.

When $R^3$ to $R^8$ in the compound [I] and the compound [Ia] is "an optionally substituted alkyl", the substituents of the alkyl are exemplified by (1) hydroxy, (2) an alkoxy group, (3) amino (said amino may be substituted by 1 or 2 group(s), being the same or different, and selected from the group consisting of an alkyl, an alkanoyl and an alkylsulfonyl), (4) an alkoxycarbonyl, (5) a cycloalkyl [said cycloalkyl may be substituted by 1 to 3 group(s), being the same or different, and selected from the group consisting of hydroxy, an amino which may be substituted by alkyl(s), an alkanoylamino, an alkylsulfonylamino, an alkyl (said alkyl may be substituted by a group selected from hydroxy, an alkoxy, amino and a carbamoyl which may be substituted by alkyl(s)), carboxy and a carbamoyl which may be substituted by alkyl(s)], (6) phenyl [said phenyl maybe substituted by 1 to 3 group(s), being the same or different, and selected from the group consisting of the following (i) to (vi): (i) a halogenatom, (ii) an alkoxy, (iii) amino (said amino maybe substituted by 1 or 2 group(s), being the same or different, and selected from the group consisting of an alkyl and an alkoxycarbonyl), (iv) an alkoxycarbonyl, (v) carbamoyl, and (vi) morpholinylcarbonyl], (7) a heterocyclic group [said heterocyclic group may be substituted by 1 to 3 group(s), being the same or different, and selected from the group consisting of the following (i) to (viii): (i) an alkyl (said alkyl may be substituted by 1 to 3 hydroxy(s)), (ii) hydroxy, (iii) amino, (iv) an alkoxycarbonyl, (v) carbamoyl, (vi) alkanoyl, (vii) alkylsulfonyl and (viii) oxo], (8) mercapto, etc. When $R^3$ to $R^8$ is an optionally substituted alkyl, said alkyl may have 1 to 3 substituent(s) mentioned above, and when the number of the substituents is 2 or more, each of the substituents may be the same or different.

When $R^3$ to $R^8$ is "a heterocyclic group-substituted alkyl", said heterocyclic group are exemplified by the above-mentioned heterocyclic groups, and preferred are 5- or 6-membered monocyclic heterocyclic groups. Specific examples are pyridyl, pyrimidinyl, pyrazinyl, piperidyl, pyrrolidinyl, morpholinyl, thienyl, furyl, tetrahydropyranyl, imidazolinyl, imidazolidinyl, piperazinyl, hexahydropyrimidinyl, etc.

When $R^3$ to $R^8$ is "an optionally substituted amino", substituents of the amino are exemplified by an alkyl (said alkyl may be substituted by 1 to 3 group(s), being the same or different, and selected from the group consisting of hydroxy, an alkoxy and a heterocyclic group), a cycloalkyl (said cycloalkyl may be substituted by 1 to 3 hydroxy(s)), a heterocyclic group, etc. The said amino may have 1 or 2 substituent(s) mentioned above, and when the number of the substituents is 2 or more, each of the substituents may be the same or different.

When $R^3$ to $R^8$ is "an amino substituted by a heterocyclic group-substituted alkyl" or "an amino substituted by a heterocyclic group", the heterocyclic group are exemplified by the above-mentioned heterocyclic groups. Preferred are 5- or 6-membered monocyclic heterocyclic groups, specific examples are pyridyl, piperidyl, pyrrolidinyl, morpholinyl, etc.

When $R^3$ to $R^8$ is "an optionally substituted alkanoyl", substituents of the alkanoyl are exemplified by hydroxy, an alkoxy, amino (said amino may be substituted by 1 or 2 group(s), being the same or different, and selected from the group consisting of an alkyl and an alkanoyl), an alkoxycarbonyl, etc. The said alkanoyl may have 1 to 3 substituent(s) mentioned above, and when the number of the substituents is 2 or more, each of the substituents may be the same or different.

When $R^3$ to $R^8$ is "an optionally substituted carbamoyl", substituents of the carbamoyl are exemplified by an alkyl, a cycloalkyl, a heterocyclic group, etc. The said carbamoyl may have 1 or 2 substituent(s) mentioned above, and when the number of the substituents is 2, each of the substituents may be the same or different.

When $R^3$ to $R^8$ is "carbamoyl substituted by a heterocyclic group", the heterocyclic group is exemplified by the above-mentioned heterocyclic group, and preferred are 5- or 6-membered monocyclic heterocyclic groups. Specific examples are pyridyl, pyrimidinyl, piperidinyl, etc.

When $R^3$ to $R^8$ is "an optionally substituted cycloalkyl", substituents of the cycloalkyl are exemplified by a halogen atom, an alkyl (said alkyl may be substituted by 1 to 3 group(s) selected from the group consisting of hydroxy, mercapto, an alkoxy, amino and a carbamoyl which may be substituted by an alkyl), hydroxy, an alkoxy, amino (said amino may be substituted by 1 or 2 group(s), being the same or different, and selected from the group consisting of an alkyl, an alkanoyl, carboxy, an alkoxycarbonyl, a carbamoyl optionally substituted by alkyl(s), an aminosulfonyl optionally substituted by alkyl(s), and an alkylsulfonyl optionally substituted by halogen(s)), carboxy, an alkanoyloxy, an alkoxycarbonyl, a carbamoyl (said carbamoyl may be substituted by 1 or 2 group(s), being the same or different, and selected from the group consisting of an alkyl, a cycloalkyl and a heterocyclic group), a carbamoyloxy optionally substituted by alkyl(s), etc. Preferable examples are an alkyl [said alkyl may be substituted by 1 to 3 group(s) selected from the group consisting of hydroxy and a carbamoyl which may be substituted by alkyl(s)], hydroxy, amino [said amino may be substituted by 1 or 2 group(s), being the same or different, and selected from the group consisting of an alkyl, an alkanoyl, an alkoxycarbonyl and an alkylsulfonyl),an alkanoyloxy, and a carbamoyl which may be substituted by alkyl(s). When $R^3$ to $R^8$ is an optionally substituted cycloalkyl, the said cycloalkyl may have 1 to 3 substituent(s) mentioned above, and when the number of the substituents is 2 or more, each of the substituents may be the same or different. Preferable examples of the substituted cycloalkyl are 4-hydroxycyclohexyl, 4-methyl-4-hydroxycyclohexyl, 4-aminocyclohexyl, 4-acetylaminocyclohexyl, 4-dimethylaminocyclohexyl, 4-carbamoylmethylaminocyclohexyl, 4-acetoxycyclohexyl, 4-hydroxymethylcyclohexyl, 2-hydroxycyclopentyl, 4-carbamoylcyclohexyl, 4-methanesulfonylaminocyclohexyl, 4-methoxycarbonylaminocyclohexyl, 4-methylcarbamoylcyclohexyl, 4-(1-hydroxy-1-methylethyl)cyclohexyl, 1-hydroxymethylcyclopentyl, etc. When $R^3$ to $R^8$ is "a cycloalkyl substituted by a heterocyclic group-substituted carbamoyl", the heterocyclic group is exemplified by the above-mentioned heterocyclic groups, and preferred are 5- or 6-membered monocyclic heterocyclic groups. Specific examples are pyridyl, pyrimidinyl, piperidinyl, etc.

When $R^3$ to $R^8$ is "an optionally substituted phenyl", substituents for the phenyl are exemplified by an alkyl optionally substituted by hydroxy, hydroxy, an alkoxy, a halogen atom, amino (said amino may be substituted by 1 or 2 alkyl(s) or alkylsulfonyl(s)), etc. The said phenyl may have 1 to 3 substituent(s) mentioned above, and when the number of the substituents is 2 or more, each of the substituents may be the same or different.

When $R^3$ to $R^8$ is "an optionally substituted heterocyclic group", the heterocyclic group is exemplified by the above-mentioned heterocyclic groups, and preferred are 5- or 6-membered monocyclic heterocyclic groups. Specific examples are piperazinyl, piperidyl, pyridyl, pyrimidinyl, pyrazinyl, pyrazolyl, pyrrolidinyl, morpholinyl, oxazolyl, thiazolyl, tetrahydropyranyl, tetrahydrothienyl, hexahydropyrimidinyl, tetrahydrothiapyranyl, tetrahydroisothiazolyl, tetrahydrothiazinyl, etc. Preferable examples of the heterocyclic group are piperazinyl, piperidyl, pyridyl, tetrahydropyranyl, tetrahydrothienyl, hexahydropyrimidinyl, tetrahydrothiapyranyl, tetrahydroisothiazolyl or tetrahydrothiazinyl. Further, substituents of the heterocyclic group are exemplified by an alkyl (said alkyl may be substituted by 1 to 3 group(s), being the same or different, and selected from the group consisting of phenyl, hydroxy, a halogen atom, oxo, an alkoxy, amino and a carbamoyl which may be substituted by an alkyl), carboxy, an alkoxycarbonyl, an alkanoyl, an alkylsulfonyl optionally substituted by halogen(s), a carbamoyl optionally substituted by alkyl(s), hydroxy, an aminosulfonyl optionally substituted by alkyl(s), oxo, etc. The said heterocyclic group may have 1 to 3 substituent(s) mentioned above, and when the number of the substituents is 2 or more, each of the substituents may be the same or different.

When $R^3$ to $R^8$ is "a carbonyl substituted by an optionally substituted cycloalkyl", substituents of the cycloalkyl are exemplified by hydroxy, an alkoxy, amino (said amino may be substituted by 1 or 2 group(s), being the same or different, and selected from the group consisting of an alkyl and an alkanoyl), an alkoxycarbonyl, etc. The said cycloalkyl may have 1 to 3 substituent(s) mentioned above, and when the number of the substituents is 2 or more, each of the substituents may be the same or different.

When $R^3$ to $R^8$ is "a carbonyl substituted by an optionally substituted phenyl", substituents of the phenyl are exemplified by a halogen atom, hydroxy, an alkoxy, amino (said amino may be substituted by 1 or 2 group(s), being the same or different, selected from the group consisting of an alkyl and an alkanoyl), etc. The said phenyl may have 1 to 3 substituent(s) mentioned above, and when the number of the substituents is 2 or more, each of the substituents may be the same or different.

When $R^3$ to $R^8$ is "a carbonyl substituted by an optionally substituted heterocyclic group", the heterocyclic group is exemplified by the above-mentioned heterocyclic groups, and preferred are 5- or 6-membered monocyclic heterocyclic groups. Specific examples are piperidyl, pyrrolidinyl, pyridyl, pyrimidinyl, morpholinyl, etc. Further, substituents of the heterocyclic group are exemplified by a halogen atom, an alkyl, hydroxy, amino (said amino may be substituted by 1 or 2 alkyl(s)), an alkanoyl, oxo, etc. The said heterocyclic group may have 1 to 3 substituent(s) mentioned above, and when the number of the substituents is 2 or more, each of the substituents may be the same or different.

$R^2$ in the compound [Ia] are preferably exemplified by —$NR^3R^4$ and —$OR^5$, and particularly preferably exemplified by —$NR^3R^4$, and further more preferably exemplified by —$NHR^4$.

When $R^2$ is —$NHR^4$, preferred examples of $R^4$ may include an optionally substituted alkyl, an alkenyl, an optionally substituted alkanoyl, an optionally substituted carbamoyl, an optionally substituted cycloalkyl, an optionally substituted phenyl, an optionally substituted heterocyclic group, a carbonyl substituted by an optionally substituted cycloalkyl and a carbonyl substituted by an optionally substituted heterocyclic group. Particularly preferred examples are an optionally substituted alkyl, an optionally substituted cycloalkyl and an optionally substituted heterocyclic group, and more preferred examples are a $c_3$-$c_6$ alkyl (said alkyl may be substituted by hydroxy(s)), a $c_5$-$c_7$ cycloalkyl (said cycloalkyl maybe substituted by a group selected from the group consisting of hydroxy, methyl, hydroxymethyl and carbamoyl), 4-piperidinyl (said 4-piperidinyl may be substituted by a $c_1$-$c_3$ alkylsulfonyl, $c_1$-$c_3$ alkylcarbamoyl or $c_1$-$c_3$ alkoxycarbonyl) and 4-tetrahydropyranyl etc.

Although an optical isomer based on an asymmetric carbon can be present in the compounds [I], [Ia] and [Ib] of the present invention, the present invention includes any of these optical isomers as well as mixtures thereof. The compounds [I], [Ia] and [Ib] can be used for a pharmaceutical use, in either a free form or in a form of a pharmaceutically acceptable salt. A pharmaceutically acceptable salt of the compound [I], [Ia] and [Ib] are exemplified by an inorganic acid salt such as a hydrochloride, a sulfate, a phosphate and a hydrobromide, and an organic acid salt such as acetate, fumarate, oxalate, citrate, methanesulfonate, benzenesulfonate, tosylate and maleate, etc. Further, in case of having a substituent such as carboxy, etc., there are mentioned a salt with a base (for example, an alkali metal salt such as a sodium salt, a potassium salt, etc. and an alkaline earth metal such as a calcium salt) The compounds [I], [Ia] and [Ib] of the present invention or a salt thereof include an internal salt thereof and a solvate thereof, such as a hydrate, etc.

The compounds [I], [Ia] and [Ib] of the present invention or a pharmaceutically acceptable salt thereof have an excellent p38 MAP kinase inhibitory action and is useful for the prophylaxis and treatment for diseases related to the activation of p38 MAP kinase and the excessive production of inflammatory mediators concerned with p38 MAP kinase such as TNF-α, IL-1, etc. Therefore, the compounds [I], [Ia] and [Ib] of the present invention or a pharmaceutically acceptable salt thereof is expected to be useful for a therapeutic and prophylactic agent for inflammatory diseases, etc. such as arthritis (rheumatoid arthritis, osteoarthritis, infectious arthritis, gouty arthritis, traumatic arthritis, synovitis, periarthritis, etc.), inflammatory bowel disease (ulcerative colitis, Crohn's disease, etc.), inflammatory dermal disease [psoriasis, dermatitis (atopic dermatitis, contact dermatitis urticaria, eczema, etc.), etc.], inflammatory respiratory disease (asthma, bronchitis, pneumonia, pleurisy, pharyngitis, rhinitis, etc.), inflammatory optical disease (conjunctivitis, keratitis, uveitis, etc.), nephritis, hepatitis, systemic inflammatory disease (Behcet's syndrome, systemic lupus erythematosus, etc.), shock (septic shock, endotoxin shock, etc.), cerebrovascular disease (cerebral hemorrhage, cerebral infarction, cerebral edema, etc.), ischemic cardiac diseases (angina pectoris, cardiac infarction, congestive heart failure, etc.), osteoporosis, multiple sclerosis, diabetes, malignant tumor, cachexia, Alzheimer's disease, Parkinson's disease, acquired immuno-deficiency syndrome, arterial sclerosis, disseminated intravascular coagulation syndrome, rejection and graft-versus-host diseases by organ transplantation, etc.

The compound of the present invention can be used in combination with one or more drugs selected from the group consisting of non-steroidal anti-inflammatory drugs, anti-rheumatic drugs, anti-cytokine drugs, immunosuppressants and steroids.

Examples of the non-steroidal anti-inflammatory drug include alcofenac, aceclofenac, sulindac, tolmetin, fenoprofen, thiaprofenic acid, tenoxicam, lornoxicam, aspirin, mefenamic acid, flufenamic acid, diclofenac, loxoprofen, phenylbutazone, indomethacin, ibuprofen, ketoprofen, naproxen, flurbiprofen, pranoprofen, piroxicam, zaltoprofen, celecoxib, rofecoxib, valdecoxib, salts thereof and the like.

Examples of the anti-rheumatic drug include gold preparation (Auranofin, etc.), penicillamine, bucillamine, lobenzarit, actarit, sulfasalazine, chloroquine, leflunomide, and the like.

Examples of the anti-cytokine drug include etanercept, infliximab, soluble TNF-α receptor, anti-TNF-α antibody, anti-interleukin-6 antibody, anti-interleukin-12 antibody and the like.

Examples of the immunosuppressant include methotrexate, cyclophosphamide, brequinar sodium, deoxyspergualin, mizoribine, 2-morphorinoethyl mycophenolate, rimexolone, cyclosporine, rapamycin, tacrolimus, gusperimus, azathiopurine and the like.

Examples of the steroid include dexamethasone, betamethasone, triamcinolone, fluocinonide, prednisolone, methylprednisolone, cortisone acetate, hydrocortisone and the like.

When the compound of the present invention is used in combination with one or more drugs above, two or more ingredients can be administered simultaneously, subsequently or separately with intervals.

The present compound (I) or a pharmaceutically acceptable salt thereof can be formulated into a pharmaceutical composition comprising a therapeutically effective amount of the compound (I) and a pharmaceutically acceptable carrier therefor. The pharmaceutically acceptable carriers include diluents, binders (e.g., syrup, gum arabic, gelatine, sorbit, tragacanth, polyvinylpyrrolidone), excipients (e.g., lactose, sucrose, corn starch, potassium phosphate, sorbit, glycine), lubricants (e.g., magnesium stearate, talc, polyethylene glycol, silica), disintegrants (e.g., potato starch) and wetting agents (e.g., sodium lauryl sulfate), and the like.

The compound (I) of the present invention or a pharmaceutically acceptable salt thereof can be administered orally or parenterally, and be used as an appropriate pharmaceutical preparation. Examples of an appropriate preparation for oral administration include solid preparations (tablets, granules, capsules, powders, etc.), solutions, suspensions and emulsions. Examples of an appropriate preparation for parenteral administration include suppository, injections or preparation for continuous infusion prepared using distilled water for injection, physiological saline or aqueous glucose solution, etc., or inhalant.

An administration amount of the compound [I], [Ia] and [Ib] of the present invention or a pharmaceutically acceptable salt thereof depends on an administration method, age, body weight, and condition of the patient, and usually, it is preferably 0.003 to 30 mg/kg, and particularly preferably, 0.01 to 10 mg/kg.

The compounds [I], [Ia] and [Ib] of the present invention can be prepared suitably by a method selected from the following [Method A] to [Method D], however, it is not limited to these. Production method will be described in detail using the compound [Ia'] which is the compound [Ia] wherein $Q^1$ is hydrogen as follow, however, the other compounds [I], [Ia] and [Ib] can be produced in a similar manner.

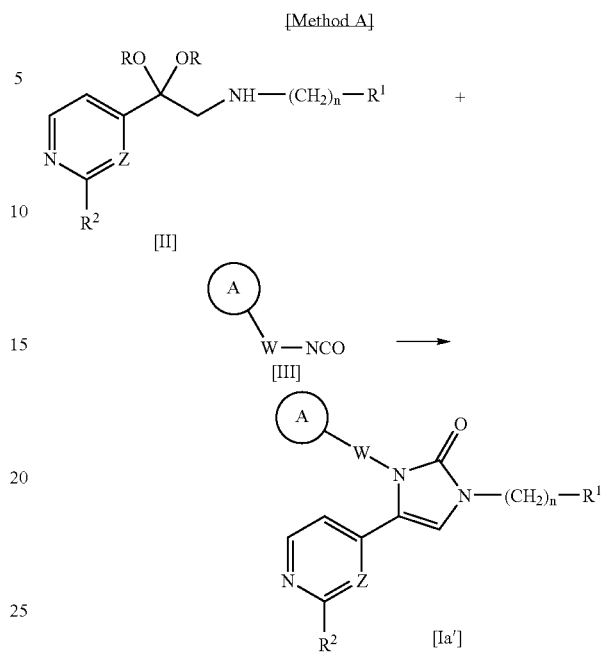

(wherein R is an alkyl, and other symbols have the same meanings as mentioned above.)

The compound [Ia'] of the present invention can be produced by reacting a compound [II] with a compound [III], followed by treating the reaction product with an acid. This reaction can be carried out in a solvent (Journal of Medicinal Chemistry, 9, 858(1966)). As the solvent, there is no limitation as long as it does not affect the reaction, for example, there are mentioned tetrahydrofuran (THF), chloroform, methylene chloride, dioxane, ethyl acetate, ether, toluene, etc. The present reaction proceeds preferably at −20 to 80° C., particularly preferably at 0 to 30° C. Further, as an acid for an acid treatment, there are mentioned, for example, hydrochloric acid, sulfuric acid, phosphoric acid, p-toluenesulfonic acid, methanesulfonic acid, etc. Additionally, as an alkyl of R in the formula [II], there are mentioned, for example, methyl, ethyl, propyl, butyl, etc., and particularly preferred are methyl and ethyl.

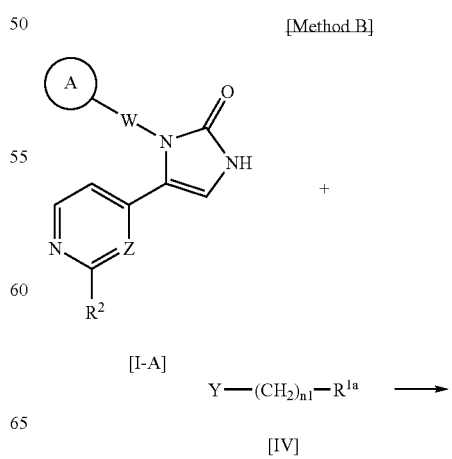

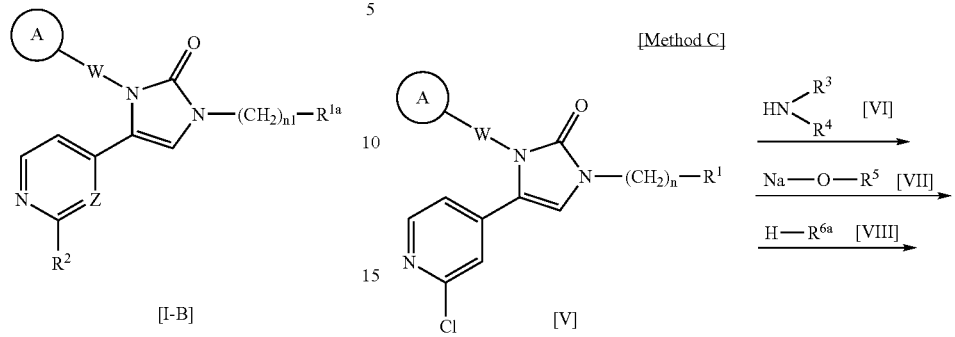

[I-B]

(wherein Y is a halogen atom, hydroxy, or dihydroxyboranyl, n1 is 0, 1,2,3 or 4, $R^{1a}$ is hydrogen atom, an optionally substituted alkyl, an optionally substituted cycloalkyl, an optionally substituted phenyl, or an optionally substituted heterocyclic group (provided that the case where n1 is 0 and $R^{1a}$ is hydrogen atom is excluded.), and other symbols have the same meanings as the above.)

The compound [I-B] which is categorized in the compound [Ia'] can be produced by reacting a compound [I-A], which is a compound [Ia'] where n is 0 and $R^1$ is hydrogen atom, with a compound [IV] for alkylation.

When Y in the formula [IV] is a halogen atom, this reaction can be carried out in a solvent, in the presence of a base. Any solvent can be used as long as it does not affect the reaction, and there are mentioned, for example, dimethylformamide (DMF), dimethylsulfoxide, 1-methylpyrrolidone, 1,3,-dimethyl-2-imidazolidinone, etc. As the base, there are mentioned, for example, sodium hydride, sodium hydroxide, potassium t-butoxide, butyllithium, lithium diisopropylamide, etc. The reaction proceeds preferably at −20 to 100° C., particularly preferably at 0 to 30° C. Further, as the halogen atom at Y, there are mentioned chlorine, bromine and iodine, and bromine and iodine are particularly preferred.

When Y in the formula [IV] is hydroxy, the reaction can be carried out in a solvent, in the presence of an additive and an activator (Synthesis, 1 (1981)). Any solvent can be used as long as it does not affect the reaction, and there are mentioned, for example, methylene chloride, THF, dioxane, chloroform, etc. As the additive, there are mentioned, for example, triphenylphosphine, tributylphosphine, trimethylphosphine, etc. As the activator, there are mentioned, for example, diethyl azodicarboxylate, dimethyl azodicarboxylate, 1,1-azobis(N,N-dimethylformamide), 1,1-(azodicarbonyl)dipiperidine, etc. This reaction proceeds preferably at −30 to 100° C., and particularly preferably at 0 to 50° C.

When Y in the formula [IV] is dihydroxyboranyl, the reaction can be carried out in a solvent, in the presence of acatalystandabase (Tetrahedron Letters, 39, 2933(1998)) Any solvent can be used as long as it does not affect the reaction, and there are mentioned, for example, methylene chloride, chloroform, DMF, etc. As the catalyst, there are mentioned, for example, copper (II) acetate, etc. As the base, there are mentioned, for example, triethylamine, diisopropylethylamine, 4-methylmorpholine, pyridine, etc. This reaction proceeds preferably at −10 to 100° C., and particularly preferably at 20 to 60° C.

[Method C]

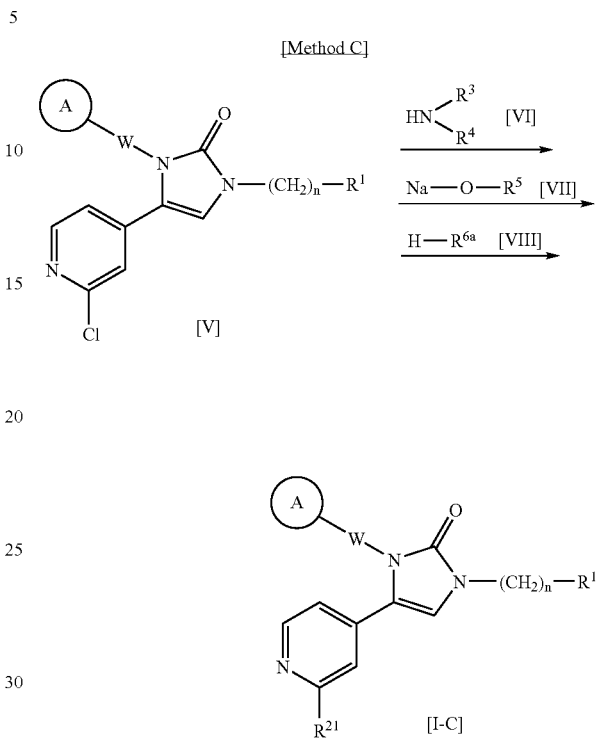

[V]

[I-C]

(wherein $R^{21}$ is —$NR^3R^4$, —$OR^5$ or —$COR^{6a}$, $R^{6a}$ is an alkoxy, and other symbols have the same meanings as the above.)

The compound [I-C] which is categorized in the compound [Ia'] of the present invention can be produced by reacting a compound [V] with a compound [VI], a compound [VII] or a compound [VIII].

The reaction between the compound [V] and the compound [VI] can be carried out in a solvent, in the presence of a catalyst, a base and an additive (Journal of Organic Chemistry, 61, 7240(1996)). Any solvent can be used as long as it does not affect the reaction, and there are mentioned, for example, toluene, xylene, dimethoxyethane, dioxane, etc.

As the catalyst, there are mentioned, for example, palladium acetate, bis(dibenzylideneacetone)dipalladium, etc. As the base, there are mentioned, for example, sodium t-butoxide, potassium t-butoxide, lithium t-butoxide, triethylamine, etc. As the additive, there are mentioned, for example, 2,2'-bis(diphenylphosphino)-1,1'binaphthyl, etc. The reaction proceeds preferably at 30 to 150° C., and particularly preferably at 60 to 80° C.

The reaction between the compound [V] and the compound [VII] can be carried out in a solvent. Any solvent can be used as long as it does not affect the reaction, and there are mentioned, for example, THF, dioxane, DMF, toluene, methanol, ethanol, etc. The reaction proceeds preferably at 20 to 150° C., and particularly preferably at 70 to 100° C.

The reaction between the compound [V] and the compound [VIII] can be carried out in a solvent, in the copresence of carbon monoxide, and in the presence of a catalyst and an additive (Tetrahedron, 55, 393(1999)). Any solvent can be used as long as it does not affect the reaction, and there are mentioned, for example, toluene, dioxane, DMF, etc. As the catalyst, there are mentioned, for example, palladium acetate, palladium chloride, bis(triphenylphosphine)palladium dichloride, tetrakis(triphenylphosphine)palladium, etc. As the additive, there are mentioned, for example, 1,1'-bis(diphenylphosphino)ferrocene, 1,4-bis(diphenylphosphino)butane, 1,3-bis(diphenylphosphino) propane, triphenylphosphine, etc. The reaction proceeds preferably at 30 to 250° C., and particularly preferably at 80 to 120° C.

[Method D]

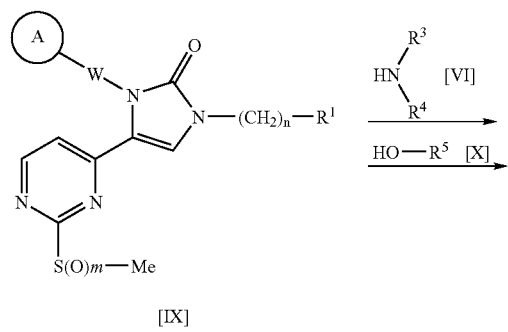

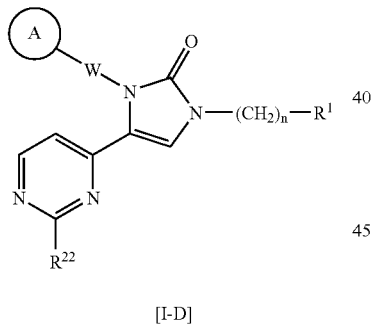

(wherein m is 1 or 2, $R^{22}$ is —$NR^3R^4$ or —$OR^5$ and other symbols have the same meanings as the above.)

The compound [I-D] which is categorized in the compound [Ia'] of the present invention can be produced by reacting a compound [IX] with a compound [VI] or a compound [X].

The reaction between the compound [IX] and the compound [VI] can be carried out in a solvent. Any solvent can be used as long as it does not affect the reaction, and there are mentioned, for example, dioxane, THF, DMF, dimethylsulfoxide, etc. The reaction proceeds preferably at 0 to 150 ° C., and particularly preferably at 50 to 100° C.

The reaction between the compound [IX] and the compound [X] can be carried out in a solvent, in the presence of a base. Any solvent can be used as long as it does not affect the reaction, and there are mentioned, for example, THF, dioxane, DMF, dimethylsulfoxide, etc. As the base, there are mentioned, for example, sodium hydride, sodium hydroxide, potassium t-butoxide, butyllithium, etc. The reaction proceeds preferably at –30 to 100 ° C., and particularly preferably at 0 to 30° C.

The compound [Ia'] produced above can also be derived to other compounds [Ia'] by converting a functional group using properly a conventionally known organic chemistry reaction. Such a method for converting a functional group may be suitably selected depending on a kind of a desired functional group. For example, a conversion of a functional group of $R^2$ in the compound [Ia'] can be carried out according to the following (method a) to (method g).

(Method a)

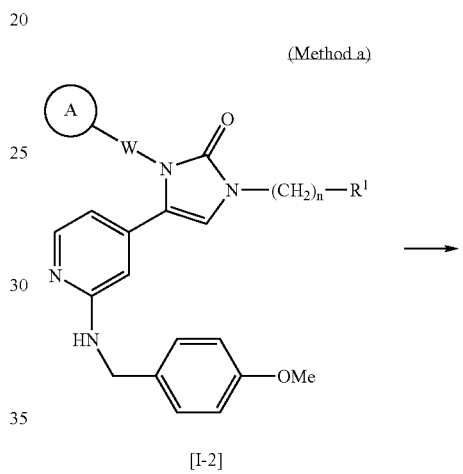

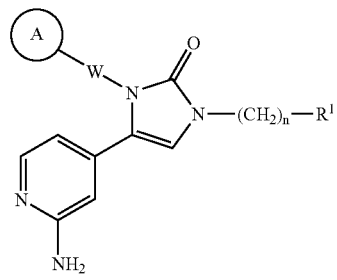

(wherein the symbols have the same meanings as the above.)

The compound [I-1] can be produced by reacting a compound [I-2] with a hydrogen halide. As the hydrogen halide, there are mentioned hydrogen fluoride, hydrogen chloride, hydrogen bromide, hydrogen iodide, etc., and particularly preferred is hydrogen bromide. This reaction proceeds preferably at 0 to 150° C., particularly preferably at 60 t 80° C.

(Method b)

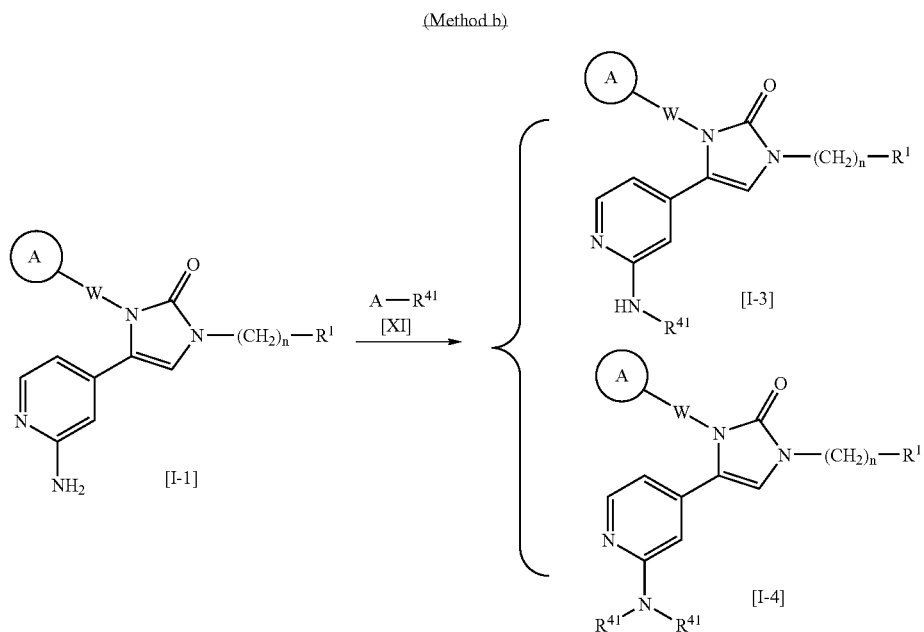

(wherein $R^{41}$ is an alkanoyl which may be substituted, an alkylsulfonyl, carbonyl substituted by a cycloalkyl which may be substituted, carbonyl substituted by a phenyl which may be substituted, or carbonyl substituted by a heterocyclic group which may be substituted. A is a halogen atom or hydroxy.

Other symbols have the same meanings as the above.)

The compound [I-3] and compound [I-4] can be produced by reacting a compound [I-1] with a compound [XI].

When A in the formula [XI] is a halogen atom, this reaction can be carried out in a solvent in the presence of a base. Any solvent can be used as long as it does not affect the reaction, and there are mentioned, for example, methylene chloride, chloroform, THF, DMF, etc. As the base, there are mentioned, for example, triethylamine, diisopropylethylamine, 4-methylmorpholine, pyridine, etc. The reaction proceeds preferably at −40 to 100° C., particularly preferably at −10 to 30° C. Further, as the halogen atom at X, there are mentioned fluorine, chlorine, bromine, and iodine, and particularly preferred are chlorine and bromine.

When A in the formula [XI] is hydroxy, this reaction can be carried out in a solvent in the presence of a condensing agent. Any solvent can be used as long as it does not affect the reaction, and there are mentioned, for example, methylene chloride, chloroform, THF, DMF, etc. As the condensing agent, there are mentioned, for example, 1,1'-carbonyldiimidazole, 1,3-dicyclohexylcarbodiimide, 1,(3-dimethylaminopropyl)-3-ethylcarbodiimide hydrochloride, etc. The reaction proceeds preferably at −40 to 100° C., particularly preferably at −10 to 30° C.

(Method c)

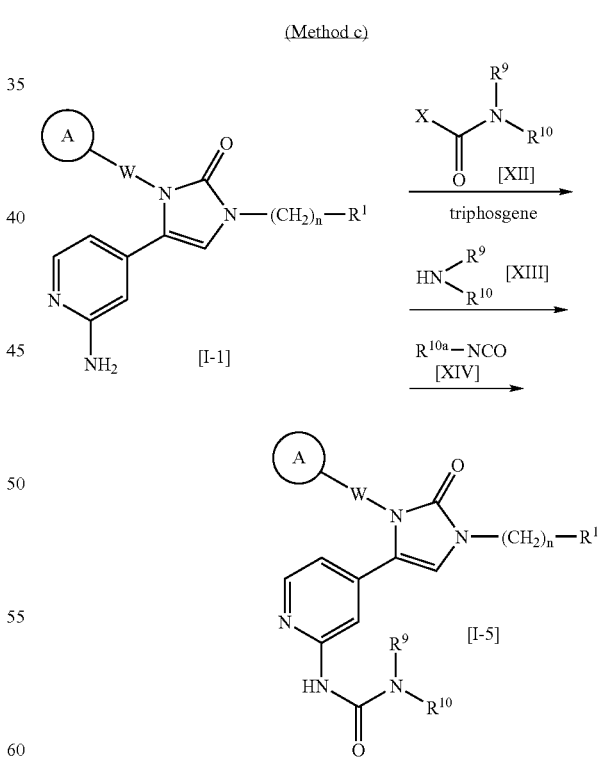

(wherein $R^9$ and $R^{10}$ are independently hydrogen atom, or an alkyl.

$R^{10a}$ is an alkyl. X is a halogen atom. Other symbols have the same meanings as the above.)

The compound [I-5] can be produced by reacting a compound [I-1] with a compound [XII], with triphosgene and a compound [XIII], or with a compound [XIV].

The compound [I-5] can be produced by reacting a compound [I-1] with a compound [XII] in a solvent. Any solvent can be used as long as it does not affect the reaction, and there are mentioned, for example, methylene chloride, chloroform, THF, etc. As the halogen atom at X in the formula [XII], fluorine, chlorine, bromine, and iodine are mentioned, and preferred is chlorine. The reaction proceeds preferably at −20 to 100° C. and particularly at 10 to 60° C.

Further, the compound [I-5] can be produced by reacting a compound [I-1] with triphosgene in a solvent, and then, by reacting with a compound [XIII]. Any solvent can be used as long as it does not affect the reaction, and there are mentioned, for example, methylene chloride, chloroform, THF, etc. The reaction proceeds preferably at −20 to 100° C. and particularly at 10 to 60° C.

Still further, a compound [I-5] in which $R^9$ is a hydrogen atom and $R^{10}$ is an alkyl can be produced by reacting a compound [I-1] with a compound [XIV] in a solvent. Any solvent can be used as long as it does not affect the reaction, and there are mentioned, for example, THF, methylene chloride, chloroform, etc. The reaction proceeds preferably at −20 to 100° C. and particularly at 10 to 60° C.

(Method d)

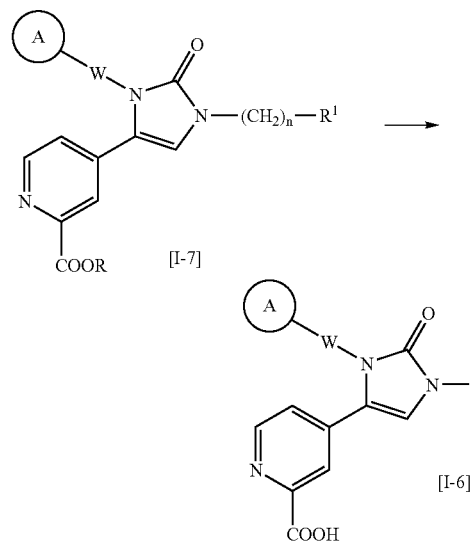

(wherein R is an alkyl, and other symbols have the same meanings as the above.)

The compound [I-6] can be produced by hydrolyzing a compound [I-7] by a conventional method.

(Method e)

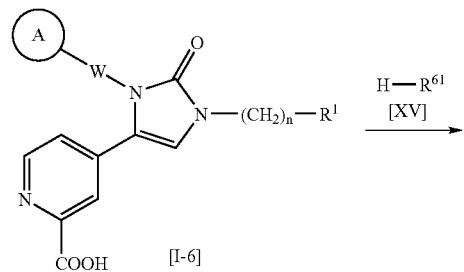

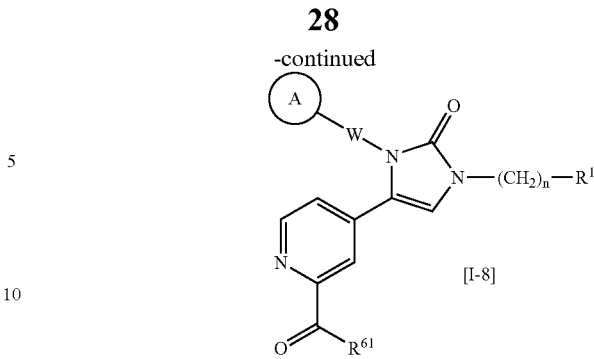

(wherein $R^{61}$ is an amino which may be substituted, and other symbols have the same meanings as the above.)

The compound [I-8] can be produced by reacting a compound [I-6] with a compound [XV] in a solvent, in the presence of a condensing agent. Any solvent can be used as long as it does not affect the reaction, and there are mentioned, for example, methylene chloride, acetonitrile, DMF, THF, etc. As the condensing agent, there are mentioned, for example, 1,1'-carbonyldiimidazole, 1,3-dicyclohexylcarbodiimide, 1,(3-dimethylaminopropyl)-3-ethylcarbodiimide hydrochloride, etc. The reaction proceeds preferably at −30 to 100° C. and particularly at 0 to 70° C.

(Method f)

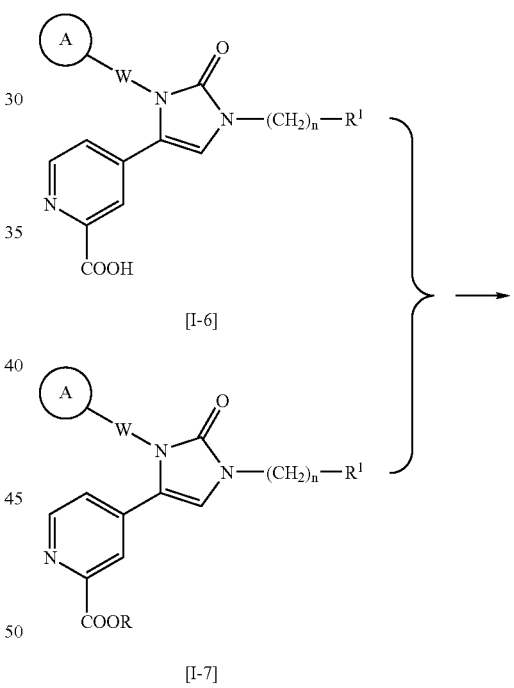

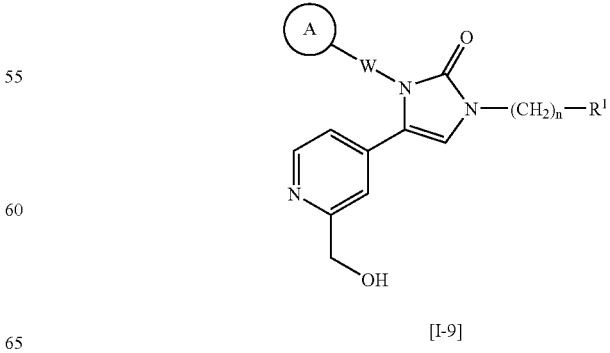

(wherein symbols have the same meanings as the above.)

The compound [I-9] can be produced by reducing a compound [I-6] or a compound [I-7] in a solvent. Any solvent can be used as long as it does not affect the reaction, and there are mentioned, for example, THF, diethyl ether, etc. As the reducing agent, there are mentioned, for example, lithium aluminum hydride, sodium borohydride, lithium borohydride, etc. The reaction proceeds preferably at −20 to 70° C. and particularly at 0 to 40° C.

(Method g)

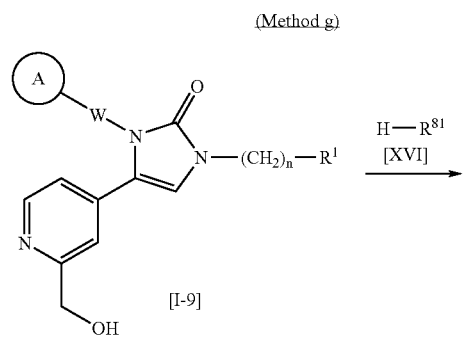

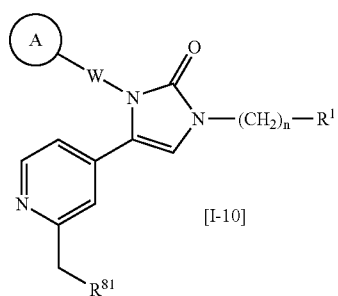

(wherein $R^{81}$ is an optionally substituted amino, and other symbols have the same meanings as the above.)

The compound [I-10] can be produced by reacting a compound [I-9] with a compound [XVI] in a solvent, in the presence of a base and an activating agent. Any solvent can be used as long as it does not affect the reaction, and there are mentioned, for example, methylene chloride, THF, chloroform, toluene, etc.

As the base, there are mentioned, for example, triethylamine, diisopropylethylamine, pyridine, etc. As the activating agent, there are mentioned, for example, methanesulfonyl chloride, p-toluenesulfonyl chloride, etc. The reaction proceeds preferably at −10 to 60° C. and particularly at 0 to 30° C.

The compound [Ia'] of the present invention obtained according to the above described [Method A] to (Method D] or (Method a) to (Method g) can be optionally converted to a pharmaceutically acceptable salt. Conversion to a pharmaceutically acceptable salt may be carried out by methods known to the person skilled in the art.

In the following, production methods for starting materials used in the above methods are described.

The starting material (II) can be produced as follows.

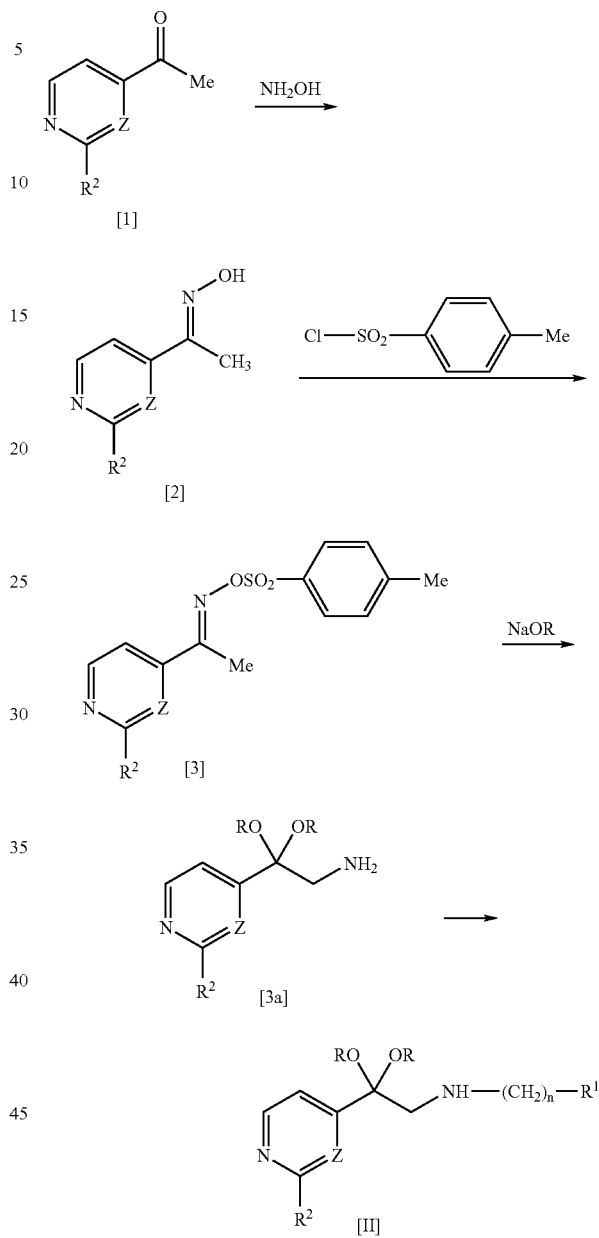

(wherein the symbols have the same meanings as the above.)

The reaction for producing the compound [2] from the compound [1] and hydroxylamine can be carried out in a solvent. 20 Any solvent can be used as long as it does not affect the reaction, and there are mentioned, for example, ethanol, methanol, etc. The reaction proceeds preferably at 0 to 150° C., and particularly preferably at 60 to 80° C.

The reaction for producing the compound [3] from the compound [2] and tosyl chloride can be carried out in a solvent. Any solvent can be used as long as it does not affect the reaction, and there are mentioned, for example, methylene chloride, chloroform, THF, toluene, etc. As the base, there are mentioned, for example, triethylamine, diisopropylethylamine, pyridine, etc. The reaction proceeds preferably at −20 to 80° C., and particularly preferably at 0 to 30° C.

The reaction for producing the compound [3a] from the compound [3] can be carried out in a solvent, by reacting the compound [3] with sodium alkoxide, followed by treating the reactant with an acid. Any solvent can be used as long as it does not affect the reaction, and there are mentioned, for example, methanol, ethanol, dioxane, THF, dimethoxyethane, etc. As the acid, there are mentioned, for example, hydrogen chloride, etc. The reaction proceeds preferably at −20 to 60° C., and particularly preferably at 0 to 30° C.

The reaction for producing the compound [II] from the compound [3a] can be carried out by reacting a corresponding aldehyde using a conventional reductive alkylation (Journal of Organic Chemistry, 61, 3849(1996)).

A starting material [V] can be produced, for example, as follows.

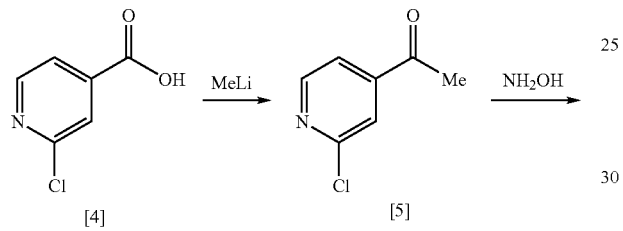

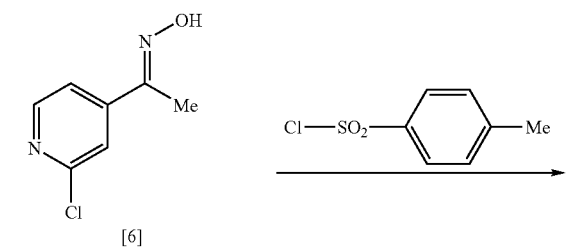

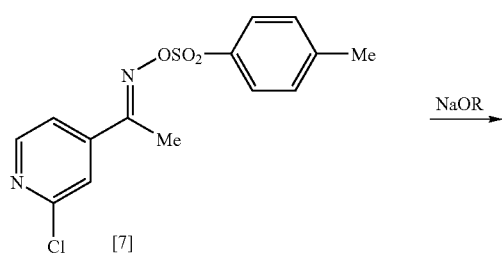

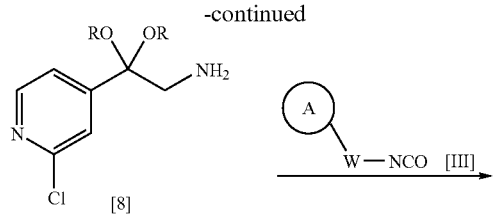

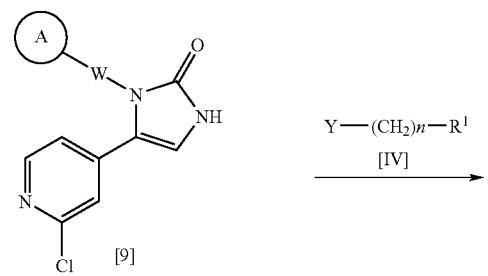

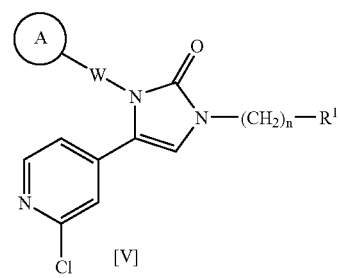

(wherein the symbols have the same meanings as the above.)

The reaction for producing the compound [5] from the compound [4] and methyl lithium can be carried out in a solvent. Any solvent can be used as long as it does not affect the reaction, and there are mentioned, for example, THF, diethyl ether, dimethoxyethane, etc. The reaction proceeds preferably at −90 to 0° C., and particularly preferably at −60 to −40° C.

The method for producing the compound [8] from the compound [5] via the compound [6] and the compound [7] can be carried out in a similar manner to the above-mentioned method for producing the compound [II] from the compound [1] via the compound [2] and the compound [3].

The reaction for producing the compound [9] from the compound [8] and the compound [III] can be carried out in a similar manner to the above-mentioned [Method A].

The reaction for producing the compound [V] from the compound[9] and the compound [IV] can be carried out in a similar manner to the above-mentioned [Method B].

A starting material [IX] can be produced, for example, as follows.

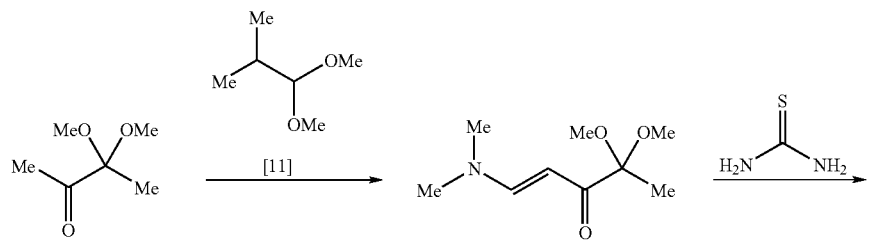
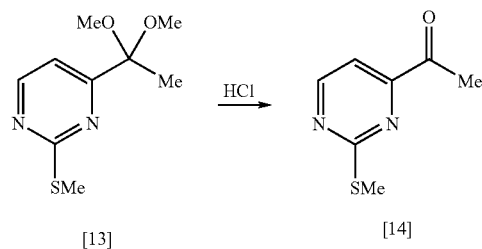
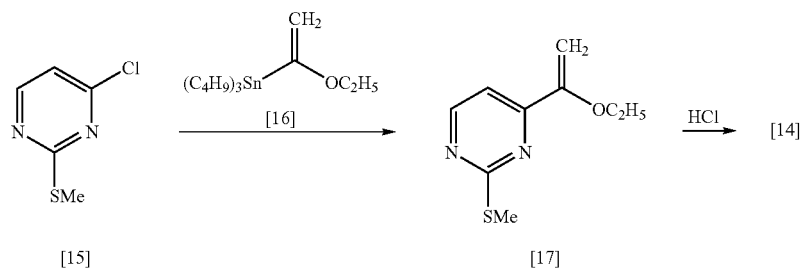
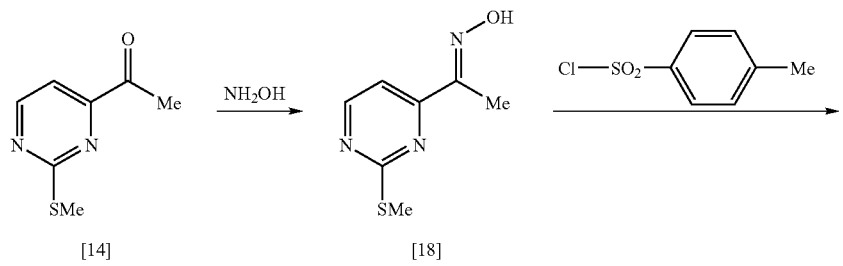
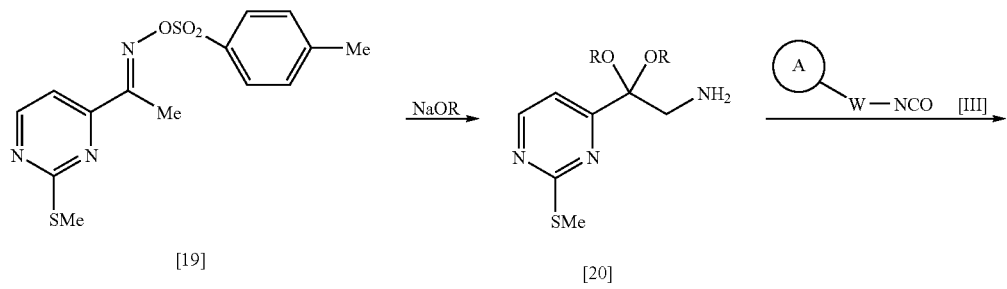

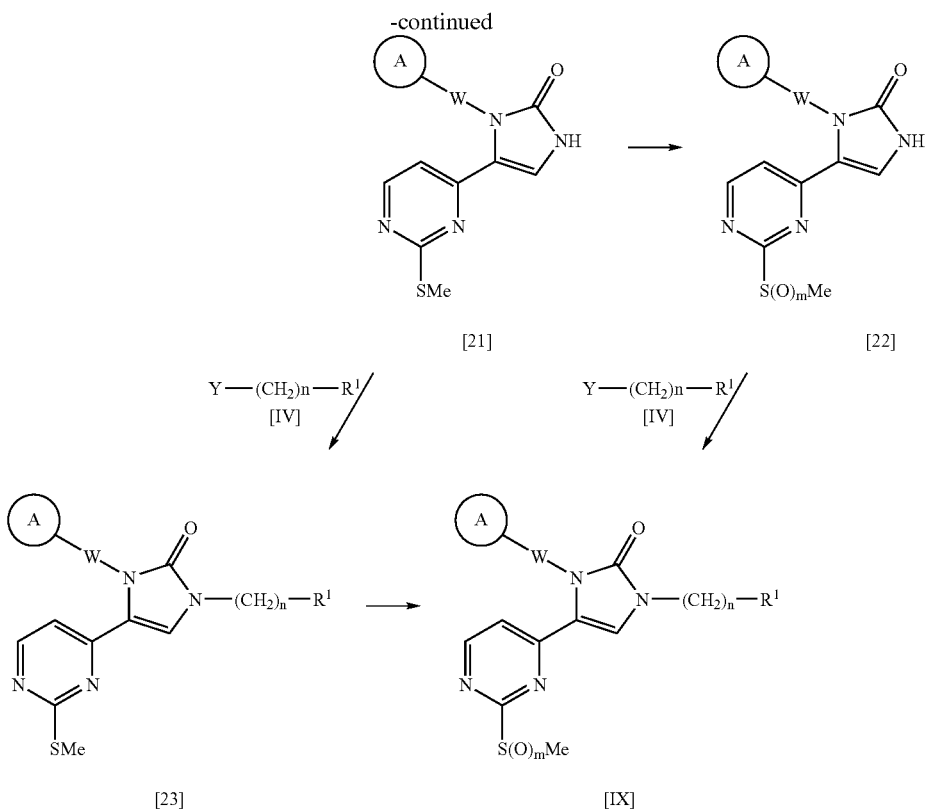

(wherein m is 1 or 2, and other symbols have the same meanings as the above.)

The reaction for producing the compound [12] from the compound [10] and the compound [11] can be carried out in a solvent or without solvent. Any solvent can be used as long as it does not affect the reaction, and there are mentioned, for example, toluene, xylene, dioxane, etc. The reaction proceeds preferably at 50 to 150° C., and particularly preferably at 80 to 120° C.

The reaction for producing the compound [13] from the compound [12] can be carried out by reacting the compound [12] with thiourea in a solvent, in the presence of a base, and then, by reacting an alkylating agent. Any solvent can be used as long as it does not affect the reaction, and there are mentioned, for example, methanol, THF, dioxane, etc. As the base, there are mentioned, for example, sodiummethoxide, sodiumhydroxide, potassium t-butoxide, etc. As the alkylating agent, there are mentioned, for example, methyl iodide, dimethyl sulfate, etc. The reaction proceeds preferably at 0 to 100° C., and particularly preferably at 30 to 70° C.

The reaction for producing the compound [14] from the compound [13] can be carried out in a solvent, in the presence of an acid. Any solvent can be used as long as it does not affect the reaction, and there are mentioned, for example, water, acetone, THF, dioxane, etc. As the acid, there are mentioned, for example, hydrochloric acid, sulfuric acid, phosphoric acid, p-toluenesulfonic acid, etc. The reaction proceeds preferably at −10 to 80° C., and particularly preferably at 0 to 30° C.

The compound [14] can be also produced from the compound [15] via the compound [17].

The reaction for producing the compound [17] from the compound [15] and the compound [16] can be carried out in a solvent, in the presence of a catalyst. Any solvent can be used as long as it does not affect the reaction, and there are mentioned, for example, DMF, toluene, xylene, etc. As the catalyst, there are mentioned, for example, bis(triphenylphosphine)palladium dichloride, tetrakis(triphenylphosphine) palladium, etc. The reaction proceeds preferably at 50 to 150° C., and particularly preferably at 70 to 90° C.

The reaction for producing the compound [14] from the compound [17] can be carried out in a similar manner to the above-mentioned method for producing the compound [14] from the compound [13].

The reaction for producing the compound [20] from the compound [14] via the compound [18] and the compound [19] can be carried out in a similar manner to the above-mentioned method for producing the compound [II] from the compound [1] via the compound [2] and the compound [3].

The reaction for producing the compound [21] from the compound [20] and the compound [III] can be carried out in a similar manner to the above-mentioned [Method A].

The reaction for producing the compound [22] from the compound [21] can be carried out in a solvent, using an oxidizing agent. Any solvent can be used as long as it does not affect the reaction, and there are mentioned, for example, water, methanol, THF, dioxane, chloroform, methylene chloride, etc. As the oxidizing agent, there are mentioned, for example, Oxon (trade name, manufactured by DuPont Co. Ltd.), 3-chloroperoxybenzoic acid, hydrogen peroxide, etc. The reaction proceeds preferably at −20 to 60° C., and particularly preferably at −10 to 30° C.

The reaction for producing the compound [IX] from the compound [22] and the compound [IV] can be carried out in a similar manner to the above-mentioned [Method B].

The compound [IX] can be also produced from the compound [21] via the compound [23].

The reaction for producing the compound [23] from the compound [21] and the compound [IV] can be carried out in a similar manner to the above-mentioned [Method B].

The reaction for producing the compound [IX] from the compound [23] can be carried out in a similar manner to the reaction for producing the compound [22] from the compound [21].

Incidentally, in the above production methods, it is possible to optionally protect or deprotect a functional group. As the protecting group for the functional group, those used in a field of conventional organic synthetic chemistry can be used, examples of which include those described in "Protective Groups in Organic Synthesis" by T. W. Greene, P. M. G. Wuts, (published by John Wiley and Sons, 1991). For conditions for introducing protecting groups or condition for de-protection, the method described in the above reference can be mentioned.

Further, each compound and each intermediate produced in the above production methods can be purified by means of a conventional method, for example, column chromatography, recrystallization, etc. As a solvent for recrystallization, there are mentioned, for example, an alcohol solvent such as methanol, ethanol, 2-propanol, etc., an ether solvent such as diethyl ether, etc., an ester solvent such as ethyl acetate, etc., an aromatic solvent such as toluene, etc., a ketone solvent such as acetone, etc., a hydrocarbon solvent such as hexane, etc., water, etc., and a mixed solvent thereof. Further, the compounds [I], [Ia] and [Ib] of the present invention can be converted to a pharmaceutically acceptable salt according to the conventional method, and recrystallization can be carried out afterwards.

EXAMPLES

Hereinbelow, the present invention will be explained in more detail with reference to the following Examples, which should not be construed as limiting the scope of the present invention.

Each of the following symbols used in the present specification represents the meaning as described below.

Me : methyl
Et ethyl
THF: tetrahydrofuran
DMF: N,N-dimethylformamide
t-: tert-

Example 1

1-(4-Fluorophenyl)-5-(pyridin-4-yl)-4-imidazolin-2-one

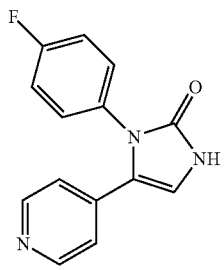

A solution of 3.00 g of 2,2-diethoxy-2-pyridin-4-ylethylamine (a compound obtained in Reference Example 2) dissolved in 30 ml of THF was cooled by water, and 1.97 g of 4-fluorophenylisocyanate was added by dropwise. After addition, the reaction mixture was concentrated under reduced pressure, and then, 30 ml of conc. hydrochloric acid was added to the obtained residue, and the mixture was stirred at room temperature overnight. To 180 ml of an ice cold aqueous 2N NaOH solution was added the reaction mixture for neutralization, and precipitated crystals were collected by filtration. They were washed with water and ether, air-dried at 60° C., to give 3.10 g of the title compound as colorless crystals. Melting point: 261° C. (decomposed)

Example 2

1-cyclopentylmethyl-3-(4-fluorophenyl)-4-(pyridin-4-yl)-4-imidazolin-2-one.hydrochloride

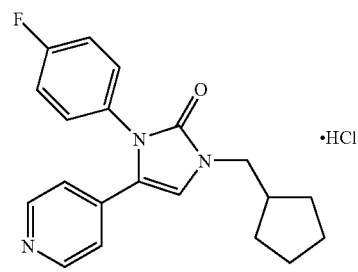

128 mg of 1-(4-Fluorophenyl)-5-(pyridin-4-yl)-4-imidazolin-2-one (the compound of Example 1), 61 µl of cyclopentylmethanol, 197 mg of triphenylphosphine and 295 µl of diethyl azodicarboxylate were dissolved in 2.5 ml of methylene chloride, and the mixture was stirred at room temperature for 24 hours. The reaction mixture was concentrated under reduced pressure, and the residue was purified by silica gel column chromatography (chloroform: ethyl acetate=19:1). The obtained compound was treated with hydrochloric acid, to give 75 mg of the title compound as powder.

Example 3

1-(Oxolan-3-yl)-3-(4-fluorophenyl)-4-(pyridin-4-yl)-4-imida zolin-2-one

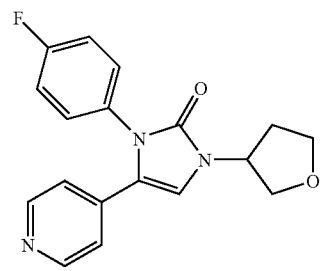

The title compound was given by treating the corresponding starting material in a similar manner to that in Example 2. Melting point: 132-134° C.

Example 4

1-(2-cyanobenzyl)-3-(4-fluorophenyl)-4-[(2-(1-(S)-phenyl-ethylamino)pyridin-4-yl)]-4-imidazolin-2-one

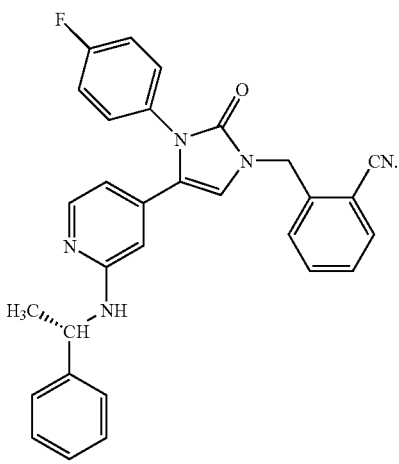

50 mg of 4-(2-chloropyridin-4-yl)-3-(4-fluorophenyl)-1-(2-cyanobenzy 1)-4-imidazolin-2-one (a compound of Reference Example 1 (6)), 79 µl of (S)-(−)-α-methylbenzylamine, 5.5 mg of palladium acetate, 15 mg of 2,2'-bis (diphenylphsophino)-1,1'-binaphthyl and 17 mg of sodium t-butoxide were suspended in 1 ml of toluene, and the mixture was stirred at 70° C. for 18 hours, under nitrogen flow. The reaction mixture was diluted by ethyl acetate, and insoluble matter was removed by filtration through Celite. To the filtrate was added 6N hydrochloric acid, and after separation, an aqueous layer was made alkaline with aqueous sodium bicarbonate solution. The mixture was extracted with chloroform, washed with saturated brine, and dried over anhydrous magnesium sulfate. After concentration under reduced pressure, the residue was purified by silica gel column chromatography (hexane:ethyl acetate=1: 2), to give 38 mg of the title compound as colorless powder.

Examples 5-12

Compounds in Table 1 were obtained by treating the corresponding starting materials in a similar manner to that in Example 4.

TABLE 1

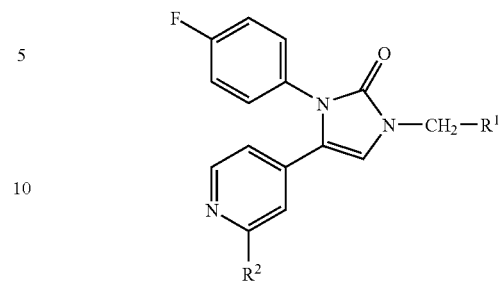

| Example | $R^1$ | $R^2$ | Physical properties, etc. |
|---|---|---|---|
| 5 | 2-Cyanophenyl | 4-Methoxybenzylamino | Melting point 167° C. |
| 6 | 2-Cyanophenyl | 2-Thienylmethylamino | Melting point 171° C. |
| 7 | 2-Cyanophenyl | (S)-1-t-Butoxycarbonylethylamino | Melting point 191-193° C. |
| 8 | 2-Cyanophenyl | Isopropylamino | Melting point 170-171° C. |
| 9 | 2-Cyanophenyl | Allylamino | Melting point 163° C. |
| 10** | 2-Methoxyphenyl | 2-Pyridylmethylamino | Melting point 248-250° C. |
| 11 | 2-Fluorophenyl | 2-(2-Pyridyl)ethylamino | Melting point 132-134° C. |
| 12** | 2-Trifluoromethylphenyl | 2-(2-Pyridyl)ethylamino | Powder |

**Dihydrochloride

Example 13

4-(2-Aminopyridin-4-yl)-1-(2-cyanobenzyl)-3-(4-fluoro-phenyl)-4-imidazolin-2-one

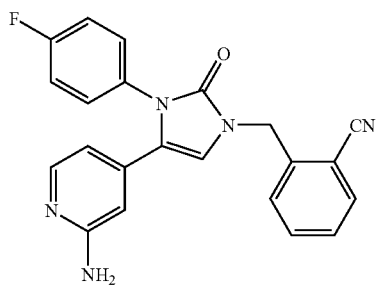

To 1.5 g of 1-(2-cyanobenzyl)-3-(4-fluorophenyl)-4-[2-(4-methoxybenzylamino)pyridin-4-yl]-4-imidazolin-2-one (Compound of Example 5) was added 3 ml of 25% hydrogen bromide-acetic acid solution, and the mixture was stirred at 70° C. for one hour. The reaction mixture was concentrated under reduced pressure, and the residue was made alkali with an aqueous sodium bicarbonate solution. The mixture was extracted with ethyl acetate, washed with brine and dried over anhydrous magnesium sulfate. After concentration under reduced pressure, the residue was purified by silica gel column chromatography (chloroform:methanol=20:1) to give 572 mg of the title compound as colorless crystal. Melting point:182-183° C.

Example 14

4-(2-N-Isobutyroylaminopyridin-4-yl)-1-(2-cyanobenzyl)-3-(4-fluorophenyl)-4-imidazolin-2-one

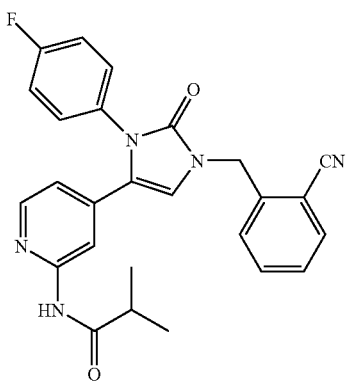

Example 15

4-(2-N,N-Diisobutyroylaminopyridin-4-yl)-1-(2-cyanobenzyl)-3-(4-fluorophenyl)-4-imidazolin-2-one

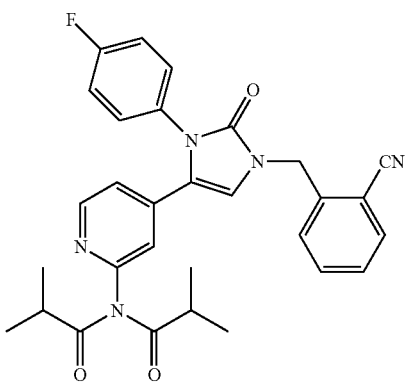

A suspension of 50 mg of 4-(2-aminopyridin-4-yl)-1-(2-cyanobenzyl)-3-(4-fluorophenyl)-4-imidazolin-2-one (Compound of Example 13) and 20 µl of isobutyroyl chloride in methylene chloride was ice-cooled, and after adding 54 µl of triethylamine by dropwise, and the mixture was stirred at room temperature for 3 hours. Water was added to the reaction mixture, and the mixture was extracted with ethyl acetate, washed with brine and dried over anhydrous magnesium sulfate. After concentration under reduced pressure, the residue was purified by silica gel column chromatography (chloroform: acetone=20:1) to give 22 mg of the title compound (Example 14) as colorless crystal and 10 mg of the title compound (Example 15) as colorless crystal, respectively. Melting point:196° C. (Example 14), 185-187° C. (Example 15).

Example 16

4-(2-Ethoxycarbonylpyridin-4-yl)-1-(2-cyanobenzyl)-3-(4-fluorophenyl)-4-imidazolin-2-one

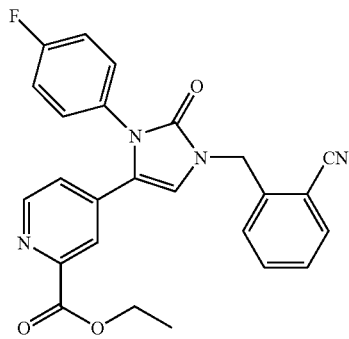

In 20 ml of ethanol were suspended 1 g of 4-(2-chloropyridin-4-yl)-3-(4-fluorophenyl)-1-(2-cyanobenzyl)-4-imid-azolin-2-one (Compound of Reference example 1(6)), 55 mg of palladium acetate, 137 mg of 1,1'-bis(diphenylphosphino)-ferrocene and 608 mg of sodium acetate, the mixture was stirred under carbon monoxide atmosphere at 80° C. for 12 hours. The reaction mixture was concentrated under reduced pressure, the residue was suspended in ethyl acetate, treated with activated charcoal and then filtered. After concentration under reduced pressure, the residue was purified by silica gel column chromatography (hexane:ethyl acetate=1:2) to give 887 mg of the title compound as colorless crystal. Melting point:164° C.

Example 17

1-(2-cyanobenzyl)-3-(4-fluorophenyl)-4-[2-(3-hydroxypropyl-amino)pyrimidin-4-yl]-4-imidazolin-2-one

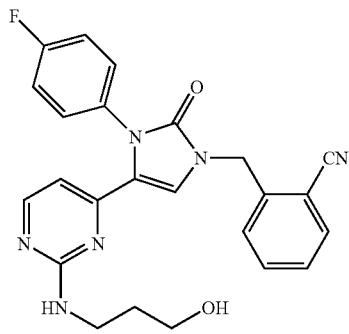

A mixture of 70 mg of 1-(2-cyanobenzyl)-3-(4-fluorophenyl)-4-(2-methylsulfinylpyrimidin-4-yl)-4-imidazolin-2-one (Compound of Reference example 6(2) or Reference example 7(2)), 60.6 mg of 3-aminopropanol and 2 ml of dioxane was stirred at 80° C. for 5 hours. The reaction mixture was concentrated and then purified by silica gel column chromatography (chloroform: methanol=19:1) and crystallized from ether to give 44.6 mg of the title compound. Melting point: 166-167° C.

Examples 18 to 24

The corresponding starting materials were treated in the same manner as in Example 17 to give Compounds in Table 2.

TABLE 2

| Example | R¹ | R² | Physical properties, etc. |
|---|---|---|---|
| 18 | 2-Cyanophenyl | 2-Furylmethylamino | Melting point 174-175° C. |
| 19 | 2-Cyanophenyl | 3-Methoxypropylamino | Melting point 168-169° C. |
| 20 | 2-Cyanophenyl | Isobutylamino | Melting point 145-146° C. |
| 21 | 2-Cyanophenyl | Allylamino | Melting point 189-190° C. |
| 22 | 2-Cyanophenyl | 4-Hydroxybutylamino | Melting point 166-167° C. |
| 23 | 2-Methoxyphenyl | Isopropylamino | Melting point 171-172° C. |
| 24 | 2-Fluorophenyl | Isopropylamino | Melting point 120-122° C. |

Example 25

1-(2-Cyanobenzyl)-3-(4-fluorophenyl)-4-(2-isopropoxy-pyrimidin-4-yl)-4-imidazolin-2-one

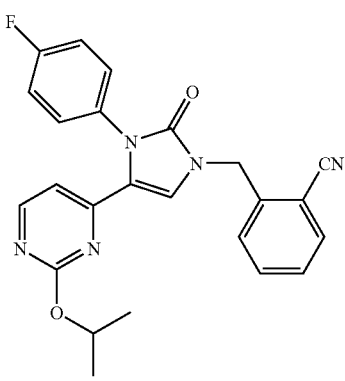

In 5 ml of isopropanol was suspended 100 mg of 1-(2-cyano-benzyl)-3-(4-fluorophenyl)-4-(2-methylsulfinylpyrimidin-4-yl)-4-imidazolin-2-one (Compound of Reference example 6(2) or Reference example 7(2)), 26.3 mg of sodium hydride was added to the mixture and the resulting mixture was stirred at room temperature for 5 hours. To the reaction mixture were successively added an aqueous citric acid solution and an aqueous sodium bicarbonate solution, and the resulting mixture was extracted with ethyl acetate. The organic layer was washed, dried and concentrated, and the residue was purified by silica gel column chromatography (chloroform:methanol=30:1) to give 68 mg of the title compound as powder.

Examples 26 to 79

The compound of Reference example 1(5) and the corresponding starting materials were subjected to N-alkylation in the same manner as in Example 2 or Reference example 1(6), and then, subjected to amination in the same manner as in Example 4 to give the compounds shown in Tables 3 to 6.

TABLE 3

| Example | R¹ | R² | MS ([M + H]⁺) |
|---|---|---|---|
| 26 | 2-Cyanophenyl | Benzylamino | 476 |
| 27 | 2-Cyanophenyl | Cyclopropylamino | 426 |
| 28 | 2-Cyanophenyl | 2-Furylmethylamino | 466 |
| 29 | 2-Cyanophenyl | 2-Pyridylmethylamino | 477 |
| 30 | 2-Cyanophenyl | Cyclopentylamino | 454 |
| 31 | 2-Cyanophenyl | 4-Chlorobenzylamino | 510 |
| 32 | 2-Cyanophenyl | 2-Methoxybenzylamino | 506 |
| 33 | 2-Cyanophenyl | 3-Methoxybenzylamino | 506 |
| 34 | 2-Cyanophenyl | 3-Pyridylmethylamino | 477 |
| 35 | 2-Cyanophenyl | 2-Methylpyridin-4-ylmethyl amino | 491 |
| 36 | 2-Cyanophenyl | 2-(2-Pyridyl)-ethylamino | 491 |
| 37 | 2-Cyanophenyl | (4-Methyl-1-piperazinyl)-amino | 484 |
| 38 | 2-Cyanophenyl | 3-Methoxypropylamino | 458 |
| 39 | 2-Cyanophenyl | 3-Propoxypropylamino | 486 |

TABLE 4

| Example | R¹ | R² | MS ([M + H]⁺) |
|---|---|---|---|
| 40 | 2-Cyanophenyl | Cyclopropylmethylamino | 440 |
| 41 | 2-Cyanophenyl | 3-Isopropoxypropylamino | 486 |

TABLE 4-continued

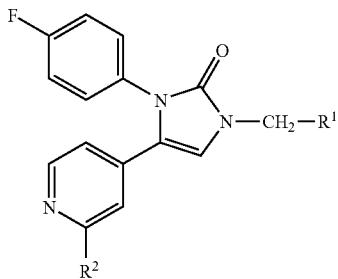

| Example | R¹ | R² | MS ([M + H]⁺) |
|---|---|---|---|
| 42 | 2-Fluorophenyl | 2-Pyridylmethylamino | 470 |
| 43** | 2-Trifluoromethylphenyl | 2-Pyridylmethylamino | 520 |
| 44 | 2-Cyanophenyl | Isobutylamino | 442 |
| 45 | 2-Cyanophenyl | 2-Ethoxyethylamino | 458 |
| 46 | 2-Trifluoromethylphenyl | Isopropylamino | 471 |
| 47 | 2-Fluorophenyl | Isopropylamino | 421 |
| 48 | 2-Methoxyphenyl | Isopropylamino | 433 |
| 49 | 2-Fluorophenyl | Isobutylamino | 435 |
| 50 | 2-Methoxyphenyl | Isobutylamino | 447 |
| 51 | 2-Cyanophenyl | t-Butylamino | 442 |
| 52 | 2-Cyanophenyl | 4-Tetrahydropyranylamino | 470 |
| 53 | 2-Cyanophenyl | (S)-1-(2-Pyridyl)ethylamino | 491 |

**Dihydrochloride

TABLE 5

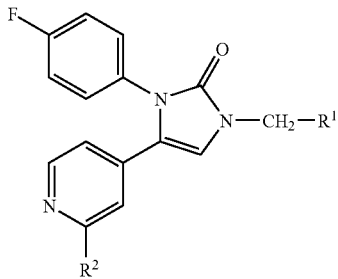

| Example | R¹ | R² | MS ([M + H]⁺) |
|---|---|---|---|
| 54 | 2-Fluorophenyl | trans-4-Hydroxycyclohexylamino | 477 |
| 55 | 4-Methoxyphenyl | Isopropylamino | 433 |
| 56 | 2-Cyanophenyl | trans-4-Hydroxycyclohexylamino | 484 |
| 57 | 4-Methoxyphenyl | (S)-1-(2-Pyridyl)ethylamino | 495 |
| 58 | 2-Fluorophenyl | 4-Methoxybenzylamino | 499 |
| 59 | cis-4-Methoxymethoxycyclohexyl | Isobutylamino | 483 |
| 60 | cis-4-Methoxymethoxycyclohexyl | trans-4-Hydroxycyclohexylamino | 524 |
| 61 | cis-4-Methoxymethoxycyclohexyl | Isopropylamino | 469 |
| 62 | 2-Fluorophenyl | (1-Methyl-4-piperidyl)amino | 476 |
| 63 | 2-Fluorophenyl | (1-t-Butoxycarbonyl-4-piperidyl)amino | 562 |
| 64 | 2-Cyanophenyl | (1-Methyl-4-piperidyl)amino | 483 |

TABLE 5-continued

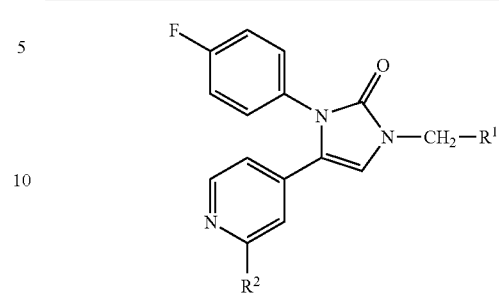

| Example | R¹ | R² | MS ([M + H]⁺) |
|---|---|---|---|
| 65* | Cyclopentyl | Isopropylamino | 395 |
| 66 | Cyclopentyl | trans-4-Hydroxycyclohexylamino | 451 |
| 67* | 4-Tetrahydropyranyl | Isopropylamino | 411 |

*Monohydrochloride;
**Dihydrochloride

TABLE 6

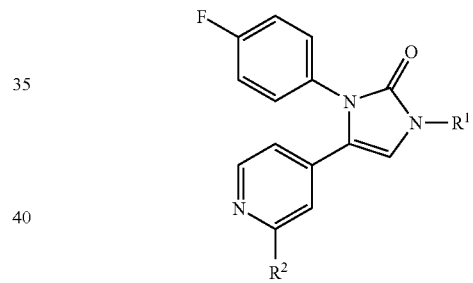

| Example | R¹ | R² | MS ([M + H]⁺) |
|---|---|---|---|
| 68* | 4-Tetrahydropyranylmethyl | trans-4-Hydroxycyclohexylamino | 467 |
| 69 | 2-Methoxyethyl | trans-4-Hydroxycyclohexylamino | 427 |
| 70 | Methoxymethyl | trans-4-Hydroxycyclohexylamino | 413 |
| 71 | Methoxymethyl | Isopropylamino | 357 |
| 72 | Methyl | trans-4-Hydroxycyclohexylamino | 383 |
| 73* | Ethyl | trans-4-Hydroxycyclohexylamino | 397 |
| 74 | Isopropyl | trans-4-Hydroxycyclohexylamino | 411 |
| 75** | Isopropyl | trans-4-Aminocyclohexylamino | 410 |
| 76* | Isopropyl | trans-4-Acetylaminocyclohexylamino | 452 |
| 77* | N-Isopropylcarbamoylmethyl | Isopropylamino | 412 |
| 78** | Isopropyl | trans-4-Dimethylaminocyclohexylamino | 438 |
| 79** | Isopropyl | trans-4-Carbamoylmethylamino-cyclohexylamino | 467 |

*Monohydrochloride;
**Dihydrochloride

Example 80

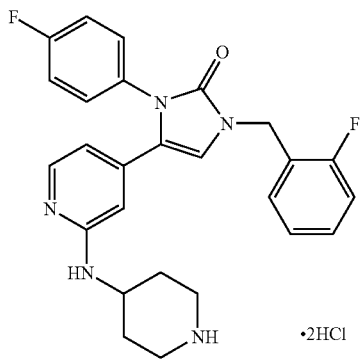

To 146 mg of the compound in Example 63 were added 0.2 ml of ethyl acetate and 1.7 ml of a 4N hydrogen chloride-ethyl acetate solution, and the mixture was stirred at room temperature for 3 hours. The reaction mixture was concentrated under reduced pressure, and ethyl acetate was added to the residue and powder was collected by filtration to give 128 mg of the title compound.

MS 462([M+H]$^+$).

Example 81

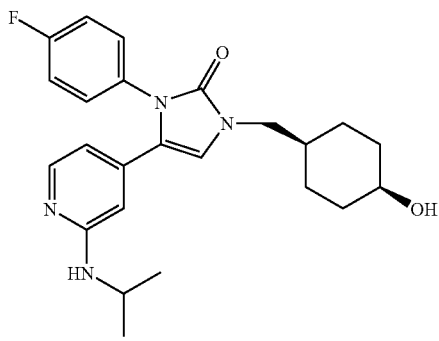

To 2 ml of methanol was dissolved 148 mg of the compound in Example 61, 1 ml of conc. hydrochloric acid was added to the mixture and the resulting mixture was stirred at room temperature overnight. The reaction mixture was concentrated under reduced pressure, and the residue was neutralized with a 4N aqueous NaOH solution and extracted with chloroform. After drying and concentration, diethyl ether and diisopropyl ether were added to the residue and the resulting powder was collected by filtration to give 58 mg of the title compound.

MS 425([M+H]$^+$).

Examples 82 to 107

The compounds of Examples 26 to 79 or the corresponding starting materials obtained in the similar method were treated in the same manner as in Example 80 or Example 81 to give the compounds shown in Tables 7 to 9.

TABLE 7

| Example | R$^1$ | R$^2$ | MS ([M + H]$^+$) |
|---|---|---|---|
| 82** | 4-Piperidyl | Isopropylamino | 410 |
| 83** | 2-Cyanophenyl | 4-Piperidylamino | 469 |
| 84 | cis-4-Hydroxy-cyclohexyl | Isobutylamino | 439 |
| 85** | cis-4-Aminocyclohexyl | Isopropylamino | 424 |
| 86** | cis-4-Aminocyclohexyl | trans-4-Hydroxycyclohexylamino | 480 |
| 87 | cis-4-Hydroxy-cyclohexyl | trans-4-Hydroxycyclohexylamino | 481 |
| 88 | cis-4-Hydroxy-cyclohexyl | (1-Methyl-4-Piperidyl)amino | 480 |
| 89 | trans-4-Amino-cyclohexyl | trans-4-Hydroxycyclohexylamino | 480 |
| 90** | 4-Piperidyl | Isobutylamino | 424 |
| 91** | 4-Piperidyl | trans-4-Hydroxycyclohexylamino | 466 |
| 92** | trans-4-Amino-cyclohexyl | Isobutylamino | 438 |
| 93** | cis-4-Aminocyclohexyl | Isobutylamino | 438 |
| 94*** | cis-4-Aminocyclohexyl | 4-Piperidylamino | 465 |

**Dihydrochloride;
***Trihydrochloride

TABLE 8

| Example | R$^1$ | R$^2$ | MS ([M + H]$^+$) |
|---|---|---|---|
| 95** | cis-4-Hydroxy-cyclohexyl | 4-Piperidylamino | 466 |
| 96*** | trans-4-Amino-cyclohexyl | 4-Piperidylamino | 465 |
| 97** | trans-4-Amino-cyclohexyl | Isopropylamino | 424 |
| 98** | 2-Fluorophenyl | trans-4-Aminocyclohexyl amino | 476 |
| 99** | 2-Cyanophenyl | trans-4-Aminocyclohexyl amino | 483 |
| 100* | trans-4-Hydroxy-cyclohexyl | Isopropylamino | 425 |

TABLE 8-continued

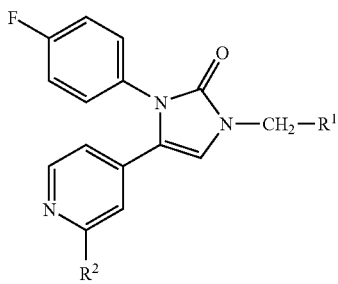

| Example | R¹ | R² | MS ([M + H]⁺) |
|---|---|---|---|
| 101* | trans-4-Hydroxycyclohexyl | Isobutylamino | 439 |
| 102* | trans-4-Hydroxycyclohexyl | trans-4-Hydroxycyclohexylamino | 481 |
| 103 | 1-Hydroxycyclopropyl | Isopropylamino | 383 |
| 104* | 1-Hydroxycyclopropyl | trans-4-Hydroxycyclohexylamino | 439 |

*Monohydrochloride;
**Dihydrochloride;
***Trihydrochloride

TABLE 9

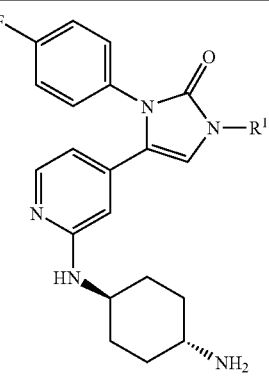

| Example | R¹ | MS ([M + H]⁺) |
|---|---|---|
| 105 | Methoxymethyl | 412 |
| 106** | 2-Methoxyethyl | 426 |
| 107** | Ethyl | 396 |

**Dihydrochloride

Examples 108 to 126

The compound of Reference example 8 and a corresponding isocyanate were reacted in the same manner as in Example 1 to carry out cyclization, and the corresponding amine was reacted in the same manner as in Example 4 to give the compounds shown in Tables 10 and 11.

TABLE 10

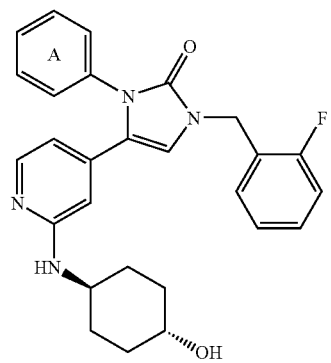

| Example | Ring A | MS ([M + H]⁺) |
|---|---|---|
| 108 | Phenyl | 459 |
| 109* | 2-Fluorophenyl | 477 |
| 110* | 3-Fluorophenyl | 477 |
| 111* | 3,4-Difluorophenyl | 495 |
| 112* | 2,4-Difluorophenyl | 495 |
| 113* | 4-Chlorophenyl | 493 |
| 114* | 4-Methylphenyl | 473 |
| 115* | 4-Methoxyphenyl | 489 |
| 116* | 3-Methoxyphenyl | 489 |
| 117* | 4-Fluorobenzyl | 491 |
| 118* | 3-Trifluoromethylphenyl | 527 |
| 119* | 3-Chlorophenyl | 493 |
| 120* | 3-Methylphenyl | 473 |
| 121* | 4-Fluoro-3-Methoxyphenyl | 507 |
| 122* | 3-Hydroxyphenyl | 475 |
| 123* | 2-Thienyl | 465 |

*Monohydrochloride

TABLE 11

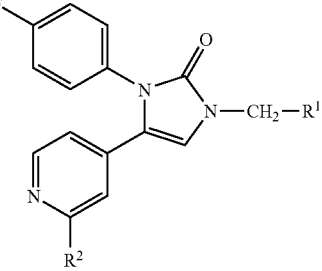

| Example | R² | MS ([M + H]⁺) |
|---|---|---|
| 124* | Isopropylamino | 439 |
| 125* | Isobutylamino | 453 |
| 126** | (1-Methyl-4-piperidyl)amino | 494 |

*Monohydrochloride;
**Dihydrochloride

Example 127

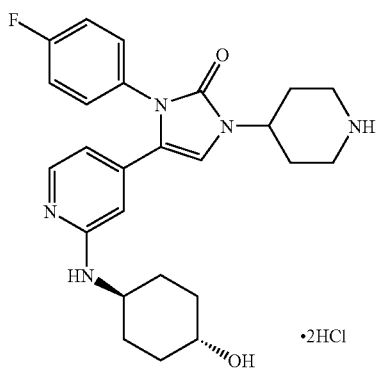

The compound of Reference example 9 was subjected to amination in the same manner as in Example 4, and then, treated in the same manner as in Example 80 to give the title compound.

MS 452 ([M+H]$^+$).

Examples 128 to 141

The compound of Reference example 8 or Reference example 10 and a corresponding starting compound were subjected to amination in the same manner as in Example 4, and then, the resulting compound was treated with a corresponding isocyanate in the same manner as in Example 1 to carry out cyclization to give the compounds shown in Tables 12 and Table 13.

TABLE 12

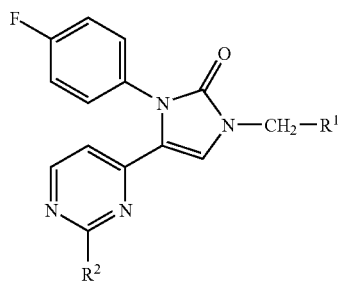

| Example | Ring A | MS ([M + H]$^+$) |
|---|---|---|
| 128* | 3-Amino-4-fluorophenyl | 492 |
| 129* | 3-Aminophenyl | 474 |
| 130* | 3-hydroxymethylphenyl | 489 |
| 131* | 2-Aminophenyl | 474 |
| 132* | 2-Nitrophenyl | 504 |
| 133* | 4-Fluoro-2-nitrophenyl | 522 |
| 134* | 2-Cyanophenyl | 484 |
| 135* | 3,5-Difluorophenyl | 495 |
| 136* | 2-Carbamoylphenyl | 502 |

*Monohydrochloride

TABLE 13

| Example | Ring A | MS ([M + H]$^+$) |
|---|---|---|
| 137* | 3-Chlorophenyl | 413 |
| 138* | 3-Methylphenyl | 393 |
| 139* | 3,4-Difluorophenyl | 415 |
| 140* | 4-Chlorophenyl | 413 |
| 141* | 2-Cyanophenyl | 404 |

*Monohydrochloride

Examples 142 to 156

The compound of Reference example 11 and a corresponding starting compound were subjected to N-alkylation in the same manner as in Reference example 8, and then, the resulting compound was treated with a corresponding isocyanate to carry out cyclization in the same manner as in Example 1 to give the compounds shown in Table 14 and Table 15.

TABLE 14

| Example | R$^1$ | MS ([M + H]$^+$) |
|---|---|---|
| 142* | 4-Tetrahydropyranyl | 397 |
| 143** | 1-Methyl-4-piperidyl | 410 |
| 144* | Cyclohexyl | 395 |
| 145* | Cyclopentyl | 381 |
| 146* | Cyclobutyl | 367 |
| 147* | 4-Piperidyl | 396 |

*Monohydrochloride;
**Dihydrochloride

TABLE 15

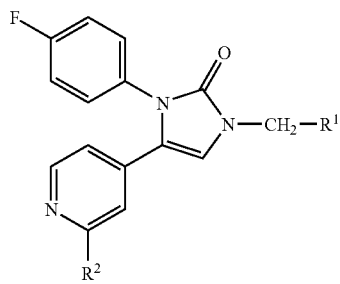

| Example | Ring A | n | R¹ | MS ([M + H]⁺) |
| --- | --- | --- | --- | --- |
| 148* | phenyl | 1 | trans-4-Hydroxycyclohexyl | 407 |
| 149* | 3-Fluorophenyl | 1 | trans-4-Hydroxycyclohexyl | 425 |
| 150* | 3-Chlorophenyl | 1 | trans-4-Hydroxycyclohexyl | 441 |
| 151* | 3-Methylphenyl | 1 | trans-4-Hydroxycyclohexyl | 421 |
| 152* | 3-Methoxyphenyl | 1 | trans-4-Hydroxycyclohexyl | 437 |
| 153* | 2,4-Difluorophenyl | 1 | trans-4-Hydroxycyclohexyl | 443 |
| 154* | 3,4-Difluorophenyl | 1 | trans-4-Hydroxycyclohexyl | 443 |
| 155* | 4-Chlorophenyl | 1 | trans-4-Hydroxycyclohexyl | 441 |
| 156* | 2-Carbamoylphenyl | 0 | Isopropyl | 380 |

*Monohydrochloride

Examples 157 to 161

By using the compound of Example 147, it was reacted with a corresponding starting compound to carry out acylation in the same manner as in Example 14 to give the compounds of Examples 157 and 158 shown in Table 16. Also, by using the compound of Example 147, it was reacted with a corresponding starting compound to carry out N-alkylation in the same manner as in Reference example 10 to give the other compounds shown in Table 16. Incidentally, in synthesis of the compound of Example 160, t-butyl bromoacetate was used as a corresponding starting compound, and after the reaction, the ester was hydrolyzed under the same conditions as in Example 80.

TABLE 16

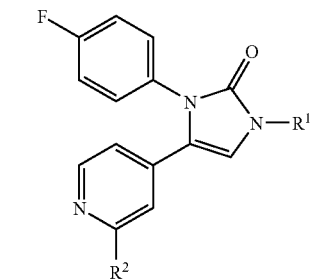

| Example | Rᵃ | MS ([M + H]⁺) |
| --- | --- | --- |
| 157* | Acetyl | 438 |
| 158* | Ethoxycarbonyl | 468 |

TABLE 16-continued

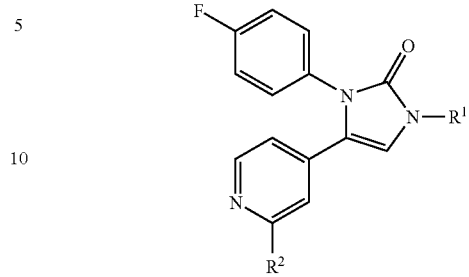

| Example | Rᵃ | MS ([M + H]⁺) |
| --- | --- | --- |
| 159** | Carbamoylmethyl | 453 |
| 160** | Carboxymethyl | 454 |
| 161** | N-Methylcarbamoylmethyl | 467 |

*Monohydrochloride;
**Dihydrochloride

Examples 162 to 168

By using the compound of Reference example 11, it was reacted with a corresponding starting compound to carry out N-alkylation in the same manner as in Reference example 10, and then, the resulting compound was subjected to cyclization in the same manner as in Example 1 to give the compound of Table 17.

TABLE 17

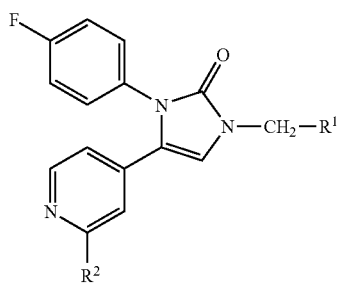

| Example | Ring A | MS ([M + H]⁺) |
| --- | --- | --- |
| 162* | 3-Fluorophenyl | 370 |
| 163* | 3-Chlorophenyl | 386 |
| 164* | 3-Methylphenyl | 366 |
| 165* | 3-Trifluoromethylphenyl | 420 |
| 166* | Phenyl | 352 |
| 167* | 2,4-Difluorophenyl | 388 |
| 168* | 4-Chlorophenyl | 386 |

*Monohydrochloride

Example 169

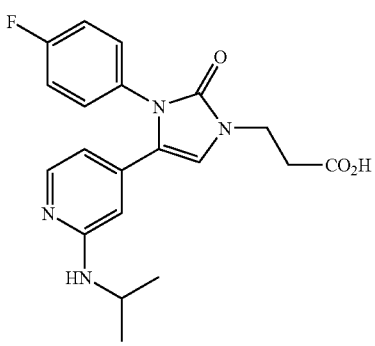

The compound (2.12 g) of Reference example 12 was subjected to cyclization in the same manner as in Example 1 and simultaneously t-butyl ester was hydrolyzed to give 1.28 g of the title compound.
MS 385 ([M+H]$^+$).

Example 170

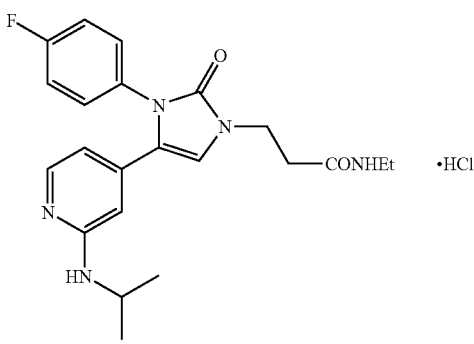

(1) A mixture comprising 100 mg of the compound of Example 169, 48 mg of 1-hydroxybenzotriazole, 60 mg of 1-(3-dimethylamino-propyl)-3-ethylcarbodiimide hydrochloride and 1 ml of methylene chloride was stirred at room temperature for one hour. To the reaction mixture was added 1 ml of a 2N ethylamine-THF solution, and the resulting mixture was stirred at room temperature overnight. The reaction mixture was successively washed with water, a saturated aqueous sodium bicarbonate solution and brine, and dried over anhydrous magnesium sulfate. To the residue obtained by concentration under reduced pressure was added diethyl ether to collect colorless crystal by filtration.

(2) The compound obtained in (1) was dissolved in 2 ml of a mixed solvent comprising chloroform-methanol, and after adding 0.2 ml of 4N hydrochloric acid-ethyl acetate, and the resulting mixture was concentrated under reduced pressure. To the residue was added ethyl acetate and collected by filtration to give 75 mg of the title compound.
MS 412([M+H]$^+$).

Examples 171 to 173

The compound of Example 169 was reacted with a corresponding amine in the same manner as in Example 170 to give the compounds shown in Table 18.

TABLE 18

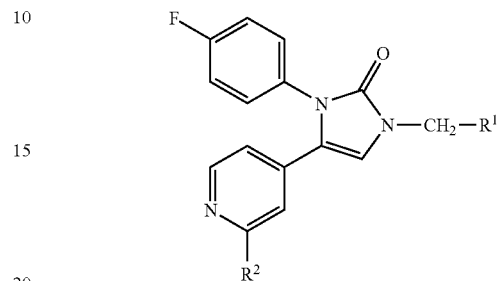

| Example | NR$^b$R$^c$ | MS ([M + H]$^+$) |
|---|---|---|
| 171* | Amino | 384 |
| 172* | Methylamino | 398 |
| 173* | Dimethylamino | 412 |

*Monohydrochloride

Examples 174 to 178

The compound of Reference example 11 was reacted with a corresponding isocyanate in the same manner as in Example 1 to give the compounds shown in Table 19.

TABLE 19

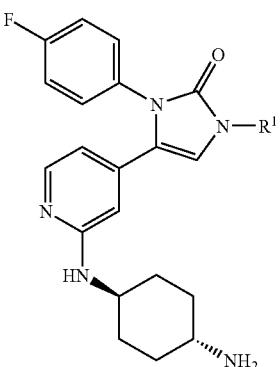

| Example | Ring A | MS ([M + H]$^+$) |
|---|---|---|
| 174* | 3,4-Difluorophenyl | 331 |
| 175* | 4-Methoxyphenyl | 325 |
| 176* | 3-Trifluoromethylphenyl | 363 |
| 177* | 3-Chlorophenyl | 329 |
| 178* | 3-Methylphenyl | 309 |

*Monohydrochloride

Example 179

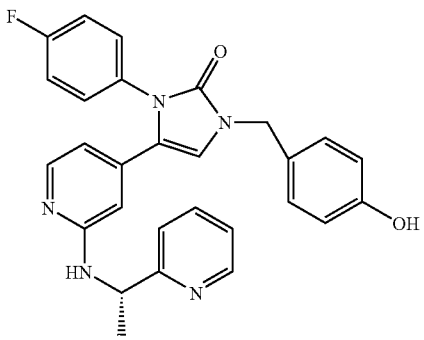

To 5 ml of 25% HBr-acetic acid solution was added 490 mg of the compound of Example 57, and the mixture was stirred at 70° C. for 15 hours. After cooling the reaction mixture, an aqueous sodium bicarbonate solution was added to neutralize the mixture, and the resulting mixture was extracted with ethyl acetate, washed with brine and dried over magnesium sulfate. After concentration under reduced pressure, the residue was purified by silica gel column chromatography to give 237 mg of the title compound as colorless powder.

MS 482 ([M+H]$^+$).

Example 180

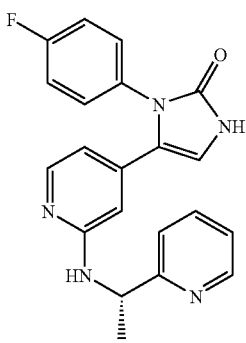

To 200 mg of the compound of Example 179 was added 2 ml of 25% HBr-acetic acid solution, and the mixture was stirred under heating at 80° C. for 3 days. After cooling the reaction mixture, an aqueous sodium bicarbonate solution was added thereto to make alkaline, and the mixture was extracted with ethyl acetate, washed with brine and dried over magnesium sulfate. After concentration under reduced pressure, the residue was purified by silica gel column chromatography to give 71 mg of the title compound as colorless powder.

MS 376 ([M+H]$^+$).

Examples 181 to 183

By using the compound of Example 55, it was reacted in the same manner as in Examples 179 and 180 to give the compounds of Examples 181 and 182 shown in Table 20. Also, in the same manner as in Example 55, a corresponding compound having isobutylamino group was synthesized, and subsequently the compound was reacted in the same manner as in Example 180 to give the compound of Example 183.

TABLE 20

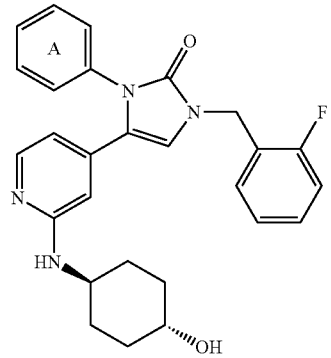

| Example | R$^1$ | n | R$^2$ | MS ([M + H]$^+$) |
|---|---|---|---|---|
| 181 | 4-Hydroxyphenyl | 1 | Isopropylamino | 419 |
| 182 | Hydrogen atom | 0 | Isopropylamino | 313 |
| 183 | Hydrogen atom | 0 | Isobutylamino | 327 |

Examples 184 and 185

By using the compound of Example 70 or the compound of Example 105, it was reacted under the same conditions (conc. hydrochloric acid was used in place of HBr-acetic acid) as in Example 179 to give the compounds shown in Table 21.

TABLE 21

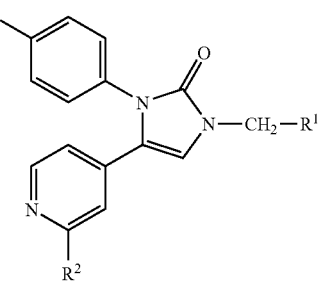

| Example | R$^2$ | MS ([M + H]$^+$) |
|---|---|---|
| 184 | trans-4-Hydroxycyclohexylamino | 369 |
| 185 | trans-4-Aminocyclohexylamino | 368 |

Examples 186 to 197

The compound of Reference example 13 was subjected to amination in the same manner as in Example 4, and then, reacted with a corresponding isocyanate in the same manner as in Example 1, and, if necessary, subjected to acetylation according to the conventional manner to give the compounds shown in Table 22.

TABLE 22

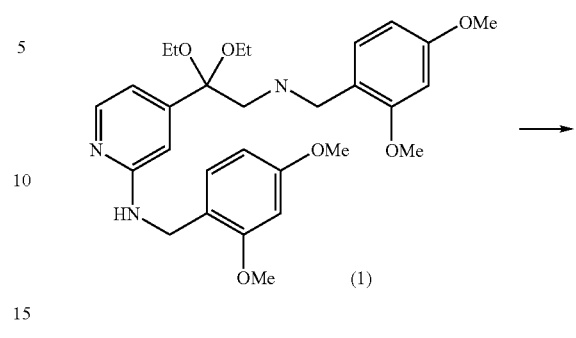

| Example | Ring A | R² | MS ([M + H]⁺) |
|---|---|---|---|
| 186 | 3-Fluorophenyl | Isobutylamino | 327 |
| 187 | 3-Fluorophenyl | Isopropylamino | 313 |
| 188 | 2,4-Difluorophenyl | Isopropylamino | 331 |
| 189 | 2-Fluorophenyl | Isopropylamino | 313 |
| 190 | 2,4-Difluorophenyl | Isobutylamino | 345 |
| 191 | 3-Methoxyphenyl | Isopropylamino | 325 |
| 192 | Phenyl | Isopropylamino | 295 |
| 193 | 2-Fluorophenyl | trans-4-Acetoxycyclohexylamino | 411 |
| 194 | 3-Fluorophenyl | trans-4-Acetoxycyclohexylamino | 411 |
| 195 | 2,4-Difluorophenyl | trans-4-Acetoxycyclohexylamino | 429 |
| 196 | Phenyl | trans-4-Acetoxycyclohexylamino | 393 |
| 197 | 3-Methoxyphenyl | trans-4-Acetoxycyclohexylamino | 423 |

Example 198

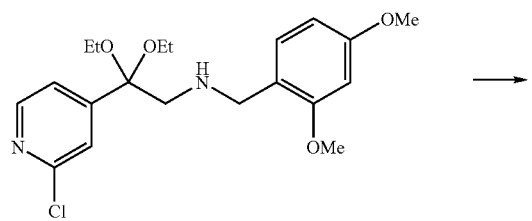

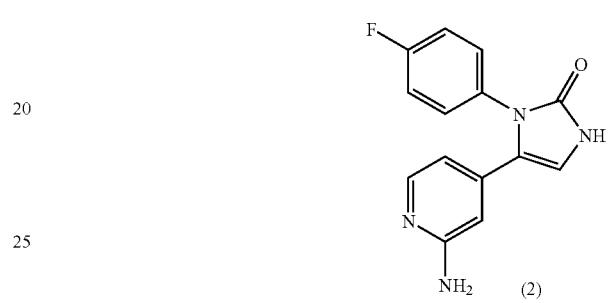

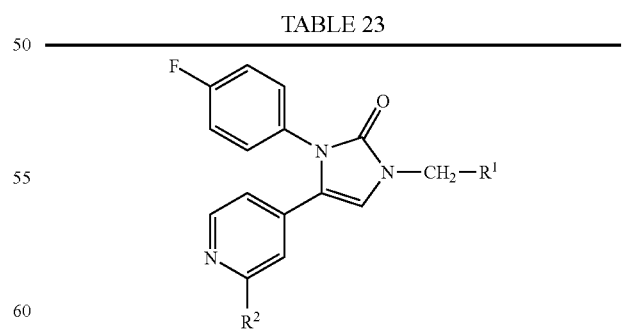

The compound (6.30 g) of Reference example 13 was reacted with 2,4-dimethoxybenzylamine in the same manner as in Example 4 to give Compound (1). Then, Compound (1) was treated in the same manner as in Example 1 to give 744 mg of Compound (2).

MS 271 ([M+H]⁺).

Examples 199 to 221

The compound of Example 182, 192, 189, 187 or 188 was reacted with a corresponding halide in the same manner as in Reference example 1(6) to subject to alkylation to give the compounds shown in Tables 23 and 24. Incidentally, the compound of Example 211 was synthesized by protecting the amino group with a t-butoxycarbonyl for the reaction and deprotecting in the same manner as in Example 80. Also, the compound of Example 214 was synthesized by eliminating a methoxymethyl group of the compound of Example 213 in the same manner as in Example 81.

TABLE 23

| Example | n | R¹ | MS ([M + H]⁺) |
|---|---|---|---|
| 199* | 0 | Methyl | 327 |
| 200 | 0 | 3-hydroxypropyl | 371 |
| 201 | 0 | Butyl | 369 |

TABLE 23-continued

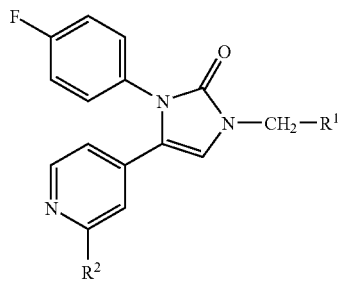

| Example | n | R¹ | MS ([M + H]⁺) |
|---|---|---|---|
| 202* | 0 | 2-Methoxyethyl | 371 |
| 203* | 0 | Carbamoylmethyl | 370 |
| 204 | 0 | Ethyl | 341 |
| 205* | 0 | Isopropyl | 355 |
| 206* | 1 | Cyclobutyl | 381 |
| 207* | 0 | Isobutyl | 369 |
| 208* | 0 | Cyanomethyl | 352 |
| 209* | 0 | Isopentyl | 383 |
| 210* | 1 | Cyclopropyl | 367 |
| 211** | 0 | 3-Aminopropyl | 370 |
| 212* | 0 | Propyl | 355 |
| 213 | 0 | 2-Methoxymethoxyethyl | 401 |
| 214* | 0 | 2-Hydroxyethyl | 357 |
| 215* | 0 | 1-Carbamoylethyl | 384 |

*Monohydrochloride;
**Dihydrochloride

TABLE 24

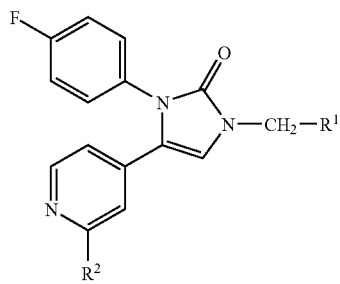

| Example | Ring A | R¹ | MS ([M + H]⁺) |
|---|---|---|---|
| 216 | Phenyl | Ethyl | 323 |
| 217 | 2-Fluorophenyl | Ethyl | 341 |
| 218 | 3-Fluorophenyl | Ethyl | 341 |
| 219* | 2,4-Difluorophenyl | Ethyl | 359 |
| 220 | Phenyl | Methoxymethyl | 339 |
| 221 | 2,4-Difluorophenyl | Methoxymethyl | 375 |

*Monohydrochloride

Examples 222 to 225

The corresponding starting materials obtained in the same manner as in Example 192 were reacted with a corresponding halide in the same manner as in Reference example 1(6) to subject to alkylation to give the compounds shown in Table 25.

TABLE 25

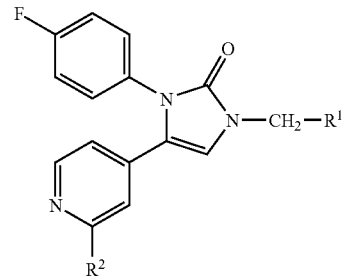

| Example | Ring A | R¹ | MS ([M + H]⁺) |
|---|---|---|---|
| 222 | 3-Fluorophenyl | Ethyl | 397 |
| 223 | 2,4-Difluorophenyl | Ethyl | 415 |
| 224 | 3-Methoxyphenyl | Ethyl | 409 |
| 225 | 2,4-Difluorophenyl | Methoxymethyl | 431 |

Example 226

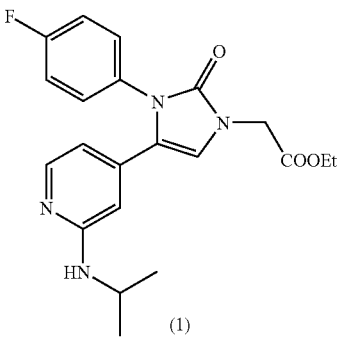

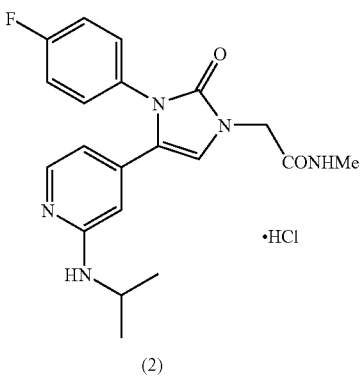

The compound of Example 182 was reacted with a corresponding halide in the same manner as in Reference example 1(6) to subject to alkylation to synthesize Compound (1). A mixture comprising 226 mg of Compound (1), 1.1 ml of 1N aqueous NaOH solution and 1.1 ml of ethanol was stirred at room temperature for 3 hours. The resulting mixture was neutralized with 1N hydrochloric acid, and precipitated crystals were collected by filtration to give 184 mg of the corresponding carboxylic acid. 148 mg of the obtained crystals was reacted with methylamine in the same manner as in Example 170 to give 96 mg of Compound (2).

MS 384 ([M+H]$^+$).

Example 227

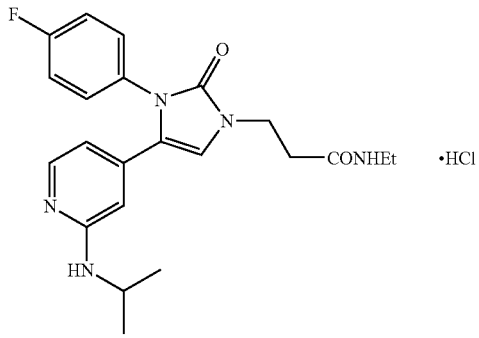

The compound of Example 226(1) was reacted with ethylamine in the same manner as in Example 226(2) to give the title compound.

MS 398 ([M+H]$^+$).

Examples 228 and 229

The compound of Reference example 1(5) was reacted with a corresponding compound in the same manner as in Reference example 1(6), subsequently the resulting compound was treated in the same manner as in Examples 5 and 13 to give the compounds shown in Table 26. Incidentally, the compound of Example 229 was synthesized by using 2,4-dimethoxybenzyl in place of 4-methoxybenzyl, and deprotecting with conc. hydrochloric acid/THF (70° C.).

TABLE 26

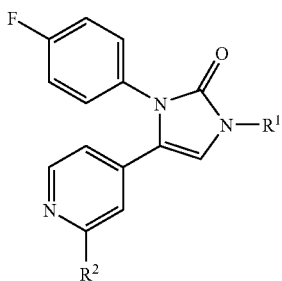

| Example | n | R$^1$ | MS ([M + H]$^+$) |
|---|---|---|---|
| 228 | 1 | 2-Fluorophenyl | 379 |
| 229 | 0 | Isopropyl | 313 |

*Monohydrochloride

Example 230

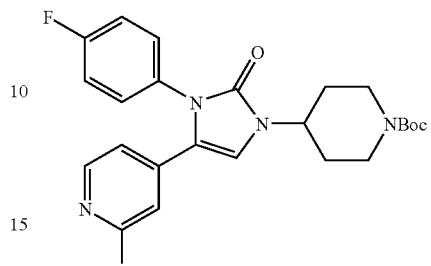

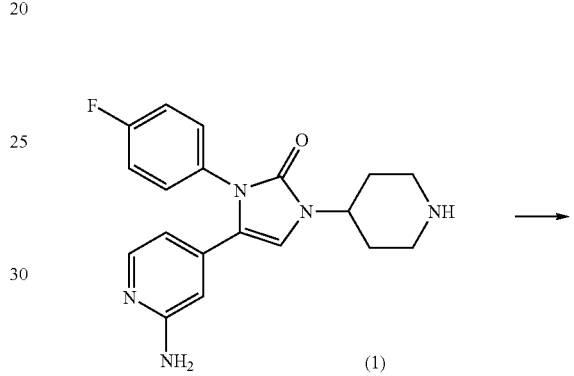

The compound (1.5 g) of Reference example 9 was reacted with 2,4-dimethoxybenzylamine and deprotected in the same manner as in Example 229 to give 707 mg of Compound (1). This compound (1) (707 mg) was dissolved in 7 ml of THF, and 410 mg of Boc$_2$O was added and the resulting mixture was stirred at room temperature for 30 minutes. After concentration under reduced pressure, diethyl ether was added to the mixture and precipitates cipitates were collected by filtration to give 770 mg of Compound (2) as colorless crystals.

MS 454 ([M+H]$^+$).

Examples 231 to 242

By using the compounds of Example 13 and Examples 228 to 230, they were reacted with an acid halide in the same manner as in Example 14, and if necessary, by removing t-butoxycarbonyl in the same manner as in Example 80 to give the compounds shown in Table 27.

TABLE 27

| Example | n | R¹ | R² | MS ([M + H]⁺) |
|---|---|---|---|---|
| 231 | 1 | 2-Cyanophenyl | Acetylamino | 428 |
| 232 | 1 | 2-Cyanophenyl | 2-Pyridylcarbonylamino | 491 |
| 233 | 1 | 2-Fluorophenyl | Acetylamino | 421 |
| 234 | 1 | 2-Fluorophenyl | Propionylamino | 435 |
| 235 | 1 | 2-Fluorophenyl | Isobutyrylamino | 449 |
| 236 | 1 | 2-Fluorophenyl | Methoxycarbonylacetylamino | 479 |
| 237 | 1 | 2-Fluorophenyl | 3-Methoxypropionylamino | 465 |
| 238 | 1 | 2-Fluorophenyl | Cyclopropylcarbonylamino | 447 |
| 239* | 0 | Isopropyl | Cyclopropylcarbonylamino | 381 |
| 240* | 0 | Isopropyl | Cyclopentylcarbonylamino | 409 |
| 241** | 0 | 4-Piperidyl | Isobutyrylamino | 424 |
| 242** | 0 | 4-Piperidyl | Cyclopropylcarbonylamino | 422 |

*Monohydrochloride;
**Dihydrochloride

Example 243

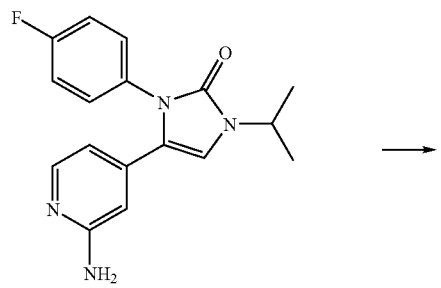

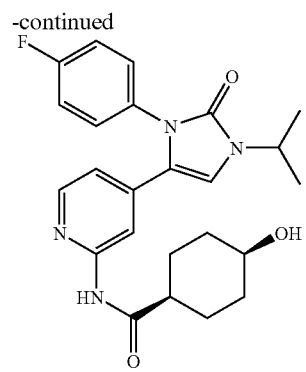

HCl

In 45 ml of acetonitrile was dissolved 4.5 g of cis-4-(methoxy-methoxy)cyclohexane carboxylic acid, 3.73 g of 1,1'-carbonyl-diimidazole was added to the solution, and the mixture was stirred at room temperature for one hour. To the mixture were added 4.07 g of the compound of Example 229 and 45 ml of acetonitrile, and the resulting mixture was refluxed under heating for 4 days. Water and an aqueous sodium bicarbonate solution were added to the reaction mixture, and the mixture was extracted with ethyl acetate. The extract was washed with brine and dried over anhydrous magnesium sulfate. After concentration under reduced pressure, 50 ml of methanol was added to the residue and the mixture was stirred for 30 minutes. The reaction mixture was concentrated under reduced pressure, and the obtained residue was purified by silica gel column chromatography to give an amide compound. This compound was treated in the same manner as in Example 81 to obtain 5.26 g of the title compound.

MS 439 ([M+H]⁺).

Examples 244 to 263

By using the compounds of Examples 228 to 230, they were reacted with a corresponding carboxylic acid in the same manner as in Example 243, and if necessary, by removing t-butoxycarbonyl in the same manner as in Example 80 to give the compounds shown in Tables 28 and 29.

TABLE 28

| Example | R² | MS ([M + H]⁺) |
|---|---|---|
| 244 | (Acetylamino)acetylamino | 478 |
| 245** | (S)-2-Amino-propionylamino | 450 |
| 246** | (S)-2-Methylamino-propionylamino | 464 |

TABLE 28-continued

[Structure shown]

| Example | R² | MS ([M + H]⁺) |
|---|---|---|
| 247** | (S)-2-Amino-3-methoxy-propionylamino | 480 |
| 248** | 3-Amino-propionylamino | 450 |
| 249** | (S)-2-Pyrrolidinylcarbonylamino | 476 |
| 250** | cis-4-Amino-cyclohexylcarbonylamino | 504 |
| 251** | 4-Piperidylcarbonylamino | 490 |
| 252 | 3-Acetylamino-propionylamino | 492 |
| 253 | (1-Acetyl-4-piperidyl)carbonylamino | 532 |

**Dihydrochloride

TABLE 29

[Structure shown]

| Example | n | R¹ | R² | MS ([M + H]⁺) |
|---|---|---|---|---|
| 254 | 1 | 2-Fluorophenyl | (S)-5-Oxopyrrolidin-2-ylcarbonylamino | 490 |
| 255* | 1 | 2-Fluorophenyl | cis-4-Hydroxy-cyclohexylcarbonylamino | 505 |
| 256 | 1 | 2-Fluorophenyl | cis-4-Acetylamino-cyclohexylcarbonyl-amino | 546 |
| 257 | 1 | 2-Fluorophenyl | (S)-1-Acetylpyrrolidin-2-ylcarbonylamino | 518 |
| 258** | 1 | 2-Fluorophenyl | trans-4-Amino-cyclohexylcarbonylamino | 504 |
| 259* | 1 | 2-Fluorophenyl | trans-4-Hydroxy-cyclohexylcarbonylamino | 505 |
| 260* | 0 | Isopropyl | (S)-5-Oxopyrrolidin-2-ylcarbonylamino | 424 |
| 261** | 0 | Isopropyl | cis-4-Amino-cyclohexylcarbonylamino | 438 |
| 262** | 0 | 4-Piperidyl | trans-4-Hydroxy-cyclohexylcarbonylamino | 480 |
| 263** | 0 | 4-Piperidyl | cis-4-Hydroxy-cyclohexylcarbonylamino | 480 |

*Monohydrochloride;
**Dihydrochloride

Examples 264 to 267

By using the compounds of Reference examples 14 and 15, they were reacted with a corresponding isocyanate in the same manner as in Example 1, subsequently, the resulting compounds were reacted with a corresponding carboxylic acid in the same manner as in Example 243 to give the compounds shown in Table 30.

TABLE 30

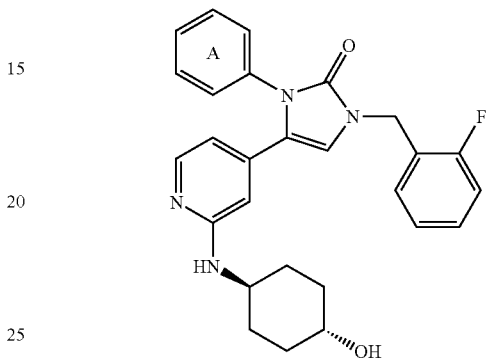

| Example | Ring A | R¹ | MS ([M + H]⁺) |
|---|---|---|---|
| 264* | 3-Chlorophenyl | Isopropyl | 455 |
| 265* | 3-Methylphenyl | Isopropyl | 435 |
| 266* | 3-Chlorophenyl | ethyl | 441 |
| 267* | 3-Methylphenyl | ethyl | 421 |

*Monohydrochloride

Example 268

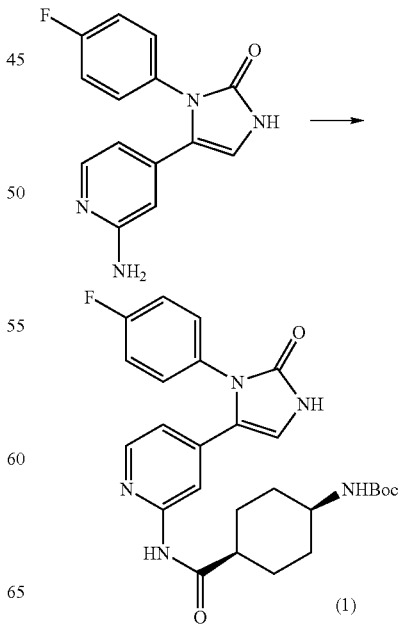

(1)

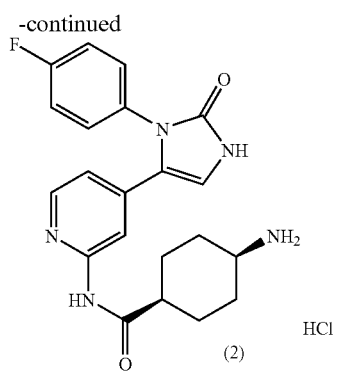

In 5 ml of acetonitrile were dissolved 540 mg of cis-4-(t-butoxycarbonyl(amino)cyclohexane carboxylic acid and 396 mg of 1,1'-carbonyldiimidazole, and the mixture was stirred at room temperature for an hour. Then, to the reaction mixture were added 200 mg of the compound of Example 198 and 5 ml of acetonitrile, and the mixture was refluxed under heating for 2 days. To the reaction mixture was added an aqueous sodium bicarbonate solution, and the mixture was extracted with chloroform. The extract was washed with brine and dried over anhydrous magnesium sulfate. After concentration under reduced pressure, the residue was dissolved in 5 ml of methanol, and 102 mg of potassium carbonate was added to the mixture. The resulting mixture was diluted with chloroform, washed with brine and dried over anhydrous magnesium sulfate. After concentration under reduced pressure, the residue was purified by silica gel column chromatography to give 255 mg of Compound (1) as colorless powder.

MS 496 ([M+H]$^+$).

Compound (1) (50 mg) was dissolved in a mixed solvent of methanol and chloroform, 0.5 ml of 4N hydrochloric acid-ethyl acetate solution was added to the mixture, and the resulting mixture was stirred at room temperature overnight. The reaction mixture was concentrated under reduced pressure to give 46 mg of Compound (2) as yellowish powder.

MS 396 ([M+H]$^+$).

Example 269

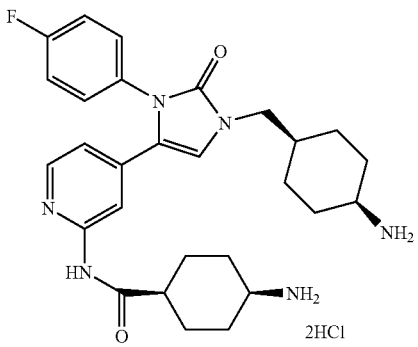

Compound (1) (100 mg) of Example 268 was dissolved in 5 ml of methylene chloride, and to the mixture were added 132 mg of diethylazodicarboxylate (40% solution in toluene), 79 mg of triphenylphosphine and 55 mg of t-butyl (4-hydroxymethylcyclohexyl) carbamate, and the resulting mixture was stirred at room temperature for 21 hours. The reaction mixture was concentrated under reduced pressure, the obtained residue was purified by silica gel column chromatography, and dissolved in 1 ml of methanol. 1 ml of 4N Hydrochloric acid-dioxane was added to the mixture, and the resulting mixture was stirred at room temperature for an hour. The reaction mixture was concentrated to give 118 mg of the title compound as yellowish powder.

MS 507 ([M+H]$^+$).

Example 270

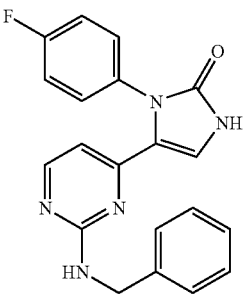

The compound of Reference example 7(1) was reacted with benzylamine in the same manner as in Example 17 to give the title compound.

MS 362 ([M+H]$^+$).

Examples 271 to 336

The compound of Reference example 5(4) was reacted in the same manner as in Example 2 or Reference example 1(6), oxidized with 3-chloroperoxybenzoic acid in the same manner as in Reference example 6(2), subsequently reacted with a corresponding amine in the same manner as in Example 17, and further, if necessary, t-butoxycarbonyl or methoxymethyl is removed in the same manner as in Example 80 or 81 to give the compounds shown in Tables 31 to 35.

TABLE 31

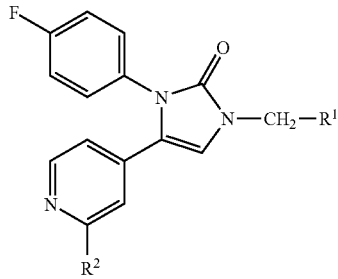

| Example | R$^2$ | MS ([M + H]$^+$) |
|---|---|---|
| 271 | Benzylamino | 477 |
| 272 | 2-Methoxyethylamino | 445 |
| 273 | Cyclopropylamino | 427 |
| 274 | Butylamino | 443 |
| 275 | Isopropylamino | 429 |
| 276 | Ethylamino | 415 |
| 277 | Cyclopropylmethylamino | 441 |
| 278 | trans-4-Hydroxycyclohexylamino | 485 |
| 279 | (S)-1-Hydroxymethyl-ethylamino | 445 |
| 280 | (S)-1-Hydroxymethyl-propylamino | 459 |

TABLE 32

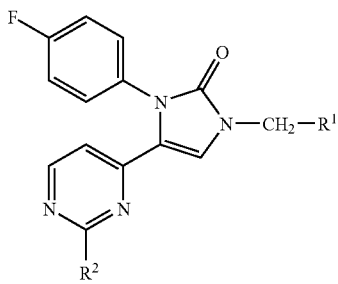

| Example | R² | MS ([M + H]⁺) |
|---|---|---|
| 281 | (S)-1-Hydroxymethyl-2-methylpropyl-amino | 473 |
| 282 | (R)-1-Hydroxymethyl-ethylamino | 445 |
| 283* | 1-Methyl-4-piperidylamino | 484 |
| 284 | 1-Benzyl-4-piperidylamino | 560 |
| 285 | 1-Ethoxycarbonyl-4-piperidylamino | 542 |
| 286 | 1-Hydroxymethyl-cyclopentylamino | 485 |
| 287 | 1-t-Butoxycarbonyl-4-piperidylamino | 570 |
| 288** | 4-Piperidylamino | 470 |
| 289 | 4-Methoxybenzylamino | 507 |
| 290** | trans-4-Aminocyclohexylamino | 484 |

*Monohydrochloride;
**Dihydrochloride

TABLE 33

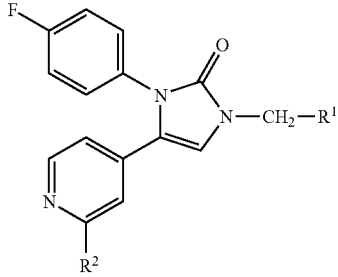

| Example | n | R¹ | R² | MS ([M + H]⁺) |
|---|---|---|---|---|
| 291 | 1 | 2-Fluorophenyl | trans-4-Hydroxy-cyclohexylamino | 478 |
| 292 | 1 | 2-Methoxyphenyl | trans-4-Hydroxy-cyclohexylamino | 490 |
| 293** | 1 | 4-Piperidyl | trans-4-Hydroxy-cyclohexylamino | 467 |
| 294** | 1 | 4-Piperidyl | Isopropylamino | 411 |
| 295 | 1 | 2-Fluorophenyl | Isobutylamino | 436 |
| 296** | 1 | 4-Piperidyl | Isobutylamino | 425 |
| 297** | 1 | 2-Fluorophenyl | 4-Piperidylamino | 463 |
| 298* | 0 | Methyl | trans-4-Hydroxy-cyclohexylamino | 384 |
| 299** | 0 | Methyl | trans-4-Aminocy-clohexylamino | 383 |
| 300* | 0 | Ethyl | trans-4-Hydroxy-cyclohexylamino | 398 |
| 301* | 0 | Ethyl | Isobutylamino | 356 |
| 302* | 0 | Isopropyl | trans-4-Hydroxy-cyclohexylamino | 412 |
| 303** | 0 | Isopropyl | trans-4-Aminocyclo-hexylamino | 411 |
| 304** | 0 | ethyl | trans-4-Aminocyclo-hexylamino | 397 |

TABLE 33-continued

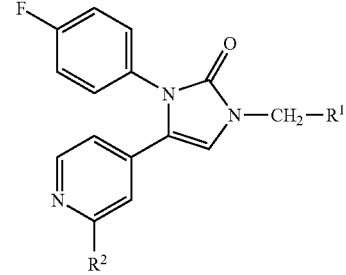

| Example | n | R¹ | R² | MS ([M + H]⁺) |
|---|---|---|---|---|
| 305* | 1 | cis-4-Hydroxy-cyclohexyl | Isopropylamino | 426 |

*Monohydrochloride;
**Dihydrochloride

TABLE 34

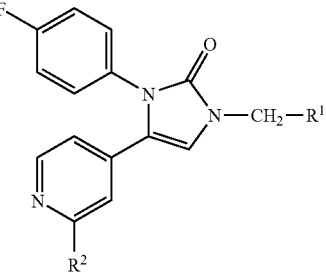

| Example | n | R¹ | R² | MS ([M + H]⁺) |
|---|---|---|---|---|
| 306* | 1 | cis-4-Hydroxycy-clohexyl | Isobutylamino | 440 |
| 307* | 1 | trans-4-Hydroxy-cyclohexyl | Isopropylamino | 426 |
| 308* | 1 | trans-4-Hydroxy-cyclohexyl | Isobutylamino | 440 |
| 309** | 1 | cis-4-Aminocy-clohexyl | Isopropylamino | 425 |
| 310** | 1 | cis-4-Aminocy-clohexyl | Isobutylamino | 439 |
| 311** | 1 | cis-4-Aminocy-clohexyl | trans-4-Hydroxycyclo-hexylamino | 481 |
| 312* | 0 | Ethyl | trans-4-acetylamino-cyclohexylamino | 439 |
| 313* | 0 | Isopropyl | trans-4-acetylamino-cyclohexylamino | 453 |
| 314*** | 1 | cis-4-Aminocy-clohexyl | trans-4-Aminocyclo-hexylamino | 480 |
| 315** | 1 | trans-4-Aminocy-clohexyl | Isopropylamino | 425 |
| 316** | 1 | trans-4-Aminocy-clohexyl | Isobutylamino | 439 |
| 317** | 1 | trans-4-Aminocy-clohexyl | trans-4-Hydroxycyclo-hexylamino | 481 |
| 318*** | 1 | trans-4-Aminocy-clohexyl | trans-4-Aminocyclo-hexylamino | 480 |
| 319* | 1 | cis-4-Hydroxycy-clohexyl | trans-4-Hydroxycyclo-hexylamino | 482 |
| 320* | 0 | Isobutyl | trans-4-Hydroxycyclo-hexylamino | 426 |

*Monohydrochloride;
**Dihydrochloride;
***Trihydrochloride

TABLE 35

[Structure: 4-fluorophenyl-imidazolone-pyridine with CH2-R1 and R2 substituents]

| Example | n | R1 | R2 | MS ([M + H]+) |
|---|---|---|---|---|
| 321* | 0 | propyl | trans-4-Hydroxycyclohexylamino | 412 |
| 322* | 0 | butyl | trans-4-Hydroxycyclohexylamino | 426 |
| 323* | 0 | Cyanomethyl | trans-4-Hydroxycyclohexylamino | 409 |
| 324* | 0 | 2-Methoxyethyl | trans-4-Hydroxycyclohexylamino | 428 |
| 325* | 0 | 3-hydroxypropyl | trans-4-Hydroxycyclohexylamino | 428 |
| 326* | 1 | Cyclopropyl | trans-4-Hydroxycyclohexylamino | 424 |
| 327* | 1 | Cyclobutyl | trans-4-Hydroxycyclohexylamino | 438 |
| 328* | 0 | Ethyl | 4-Tetrahydropyranylamino | 384 |
| 329* | 0 | Ethyl | (S)-1-Hydroxymethylethylamino | 358 |
| 330* | 0 | Ethyl | 2-Hydroxy-1,1-dimethylethylamino | 372 |
| 331* | 0 | Ethyl | 1-Hydroxymethyl-cyclopentylamino | 398 |
| 332* | 0 | Ethyl | 3-Methoxypropylamino | 372 |
| 333 | 0 | Isopropyl | 2-Hydroxy-1,1-dimethylethylamino | 386 |
| 334 | 0 | Isopropyl | 1-Hydroxymethyl-cyclopentylamino | 412 |
| 335 | 0 | Ethyl | cis-4-Hydroxycyclohexylamino | 398 |
| 336 | 0 | Isopropyl | cis-4-Hydroxycyclohexylamino | 412 |

*Monohydrochloride

Examples 337 to 343

The compound of Reference example 16 was reacted with a corresponding isocyanate in the same manner as in Example 1, oxidized with 3-chloroperoxybenzoic acid in the same manner as in Reference example 6(2), subsequently reacted with a corresponding amine in the same manner as in Example 17 to give the compounds shown in Table 36.

TABLE 36

[Structure: 4-fluorophenyl-imidazolone-pyridine with N-R1 and R2 substituents]

| Example | Ring A | MS ([M + H]+) |
|---|---|---|
| 337* | 3-Fluorophenyl | 412 |
| 338* | 3-Methylphenyl | 408 |
| 339* | Phenyl | 394 |
| 340* | 3-Chlorophenyl | 428 |
| 341* | 4-Chlorophenyl | 428 |
| 342* | 2,4-Difluorophenyl | 430 |
| 343* | 3-Methoxyphenyl | 424 |

*Monohydrochloride

Examples 344 to 349

The compound of Reference example 17(3) was reacted with a corresponding isocyanate in the same manner as in Example 1 to give the compounds shown in Table 37.

TABLE 37

[Structure: 4-fluorophenyl-imidazolone-pyridine with CH2-R1 and R2 substituents]

| Example | Ring A | MS([M + H]+) |
|---|---|---|
| 344* | 3-Chlorophenyl | 414 |
| 345* | 3-Methylphenyl | 394 |
| 346* | 3-Trifluoromethylphenyl | 448 |
| 347* | 4-Chlorophenyl | 414 |
| 348* | Phenyl | 380 |
| 349* | 3-Fluorophenyl | 398 |

*Monohydrochloride

Example 350

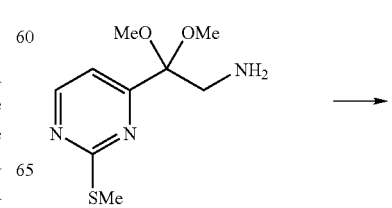

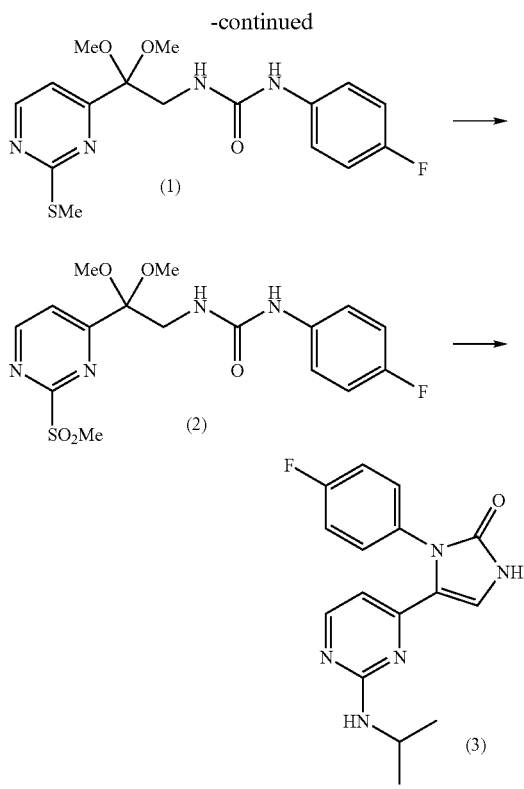

(1) To 300 ml of a diethyl ether solution containing 52.0 g of the compound of Reference example 5(3) was added dropwise 100 ml of a diethyl ether solution containing 30.2 g of 4-fluorophenyl isocyanate under ice-cooling, and the mixture was stirred at room temperature for 30 minutes. After concentration under reduced pressure, diisopropyl ether was added to the reaction mixture and crystals were collected by filtration to give 75.0 g of Compound (1) as colorless crystals.

(2) In chloroform was dissolved 30.0 g of Compound (1), and under ice-cooling, 46.4 g of 3-chloroperoxybenzoic acid was added to the solution and the mixture was stirred at room temperature for 2 hours. After concentration under reduced pressure, diethyl ether was added to the reaction mixture and crystals were collected by filtration to give 30.8 g of Compound (2) as colorless crystals.

(3) To the compound obtained by treating 20.0 g of Compound (2) with a corresponding starting material in the same manner as in Example 17 was added 100 ml of conc. hydrochloric acid, and the mixture was stirred at room temperature overnight. A 2N aqueous sodium hydroxide solution was added to the mixture to neutralize the same, ethyl acetate was added to the same and after stirring, precipitated crystals were collected by filtration to give 12.4 g of the title compound as colorless crystals.

MS 314 ([M+H]$^+$).

Examples 351 to 354

The compound of Reference example 5(3) and a corresponding starting material were treated in the same manner as in Example 350 to give the compounds shown in Table 38.

TABLE 38

| Example | Ring A | R$^2$ | MS ([M + H]$^+$) |
|---|---|---|---|
| 351 | 4-Fluorophenyl | trans-4-Hydroxycyclohexylamino | 370 |
| 352* | 4-Fluorophenyl | Isobutylamino | 328 |
| 353 | 2,4-Difluorophenyl | Isopropylamino | 332 |
| 354 | Phenyl | Isopropylamino | 296 |

*Monohydrochloride

Examples 355 to 367

By using the compound of Example 350, 353 or 354, or the compound produced by the same manner as in Example 350, they were treated in the same manner as in Reference example 1(6) to give the compounds shown in Table 39.

TABLE 39

| Example | Ring A | R$^1$ | MS ([M + H]$^+$) |
|---|---|---|---|
| 355* | 4-Fluorophenyl | Methyl | 328 |
| 356* | 4-Fluorophenyl | Ethyl | 342 |
| 357* | 4-Fluorophenyl | Methoxymethyl | 358 |
| 358 | 2,4-Difluorophenyl | Ethyl | 360 |
| 359 | Phenyl | Ethyl | 324 |
| 360 | 4-Chlorophenyl | Ethyl | 358 |
| 361 | 3-Fluorophenyl | Ethyl | 342 |
| 362 | 3-Methoxyphenyl | Ethyl | 354 |
| 363 | 2,4-Difluorophenyl | Methoxymethyl | 376 |
| 364 | Phenyl | Methoxymethyl | 340 |
| 365 | 4-Chlorophenyl | Methoxymethyl | 374 |
| 366* | 4-Fluorophenyl | 2-Methoxyethyl | 372 |
| 367* | 4-Fluorophenyl | Cyanomethyl | 353 |

*Monohydrochloride

Examples 368 to 382

Compound of Reference example 5(4) was reacted in the same manner as in Example 2 or Reference example 1(6), oxidized with 3-chloroperoxybenzoic acid in the same manner as in Reference example 6(2), subsequently reacted with a corresponding amine in the same manner as in Example 17, and if necessary, t-butoxycarbonyl was removed in the same manner as in Example 80 to give the compounds shown in Table 40.

TABLE 40

| Example | R¹ | R² | MS ([M + H]⁺) |
|---|---|---|---|
| 368* | Ethyl | cis-4-Hydroxymethyl-cyclohexylamino | 412 |
| 369* | Ethyl | trans-4-Hydroxymethyl cyclohexylamino | 412 |
| 370* | Ethyl | 3-Hydroxy-2,2-dimethyl-propylamino | 386 |
| 371* | Isopropyl | cis-4-Hydroxymethyl-cyclohexylamino | 426 |
| 372* | Isopropyl | trans-4-Hydroxymethyl-cyclohexylamino | 426 |
| 373* | Isopropyl | 3-Hydroxy-2,2-dimethyl-propylamino | 400 |
| 374* | Isopropyl | (S)-2-Hydroxypropylamino | 372 |
| 375* | Isopropyl | (R)-2-Hydroxypropylamino | 372 |
| 376* | Isopropyl | 1-Hydroxycyclohexyl-methylamino | 426 |
| 377** | Isopropyl | 2-Hydroxy-1-hydroxy-methyl-1-methylethyl-amino | 402 |
| 378** | Isopropyl | 4-Piperidyl | 397 |
| 379** | Isopropyl | (S)-1-(2-Pyridyl)ethyl-amino | 419 |
| 380* | Isopropyl | (1S,2S)-2-Hydroxycyclo-pentylamino | 398 |
| Examples | | | |
| 381* | Ethyl | (1S,2S)-2-Hydroxycyclo-pentylamino | 384 |
| 382* | Ethyl | trans-4-Carbamoylcyclo-hexylamino | 425 |

*Monohydrochloride;
**Dihydrochloride

Examples 383 to 386

The compound of Example 303 or 304 was subjected to methanesulfonylation or methoxycarbonylation according to the conventional methods to give the compounds shown in Table 41.

TABLE 41

| Examples | R¹ | R² | MS ([M + H]⁺) |
|---|---|---|---|
| 383* | Isopropyl | trans-4-Methanesulfonyl-aminocyclohexylamino | 489 |
| 384* | Isopropyl | trans-4-Methoxycarbonyl-aminocyclohexylamino | 469 |
| 385* | Ethyl | trans-4-Methanesulfonyl-aminocyclohexylamino | 475 |
| 386* | Ethyl | trans-4-Methoxycarbonyl-aminocyclohexylamino | 455 |

*Monohydrochloride

Example 387

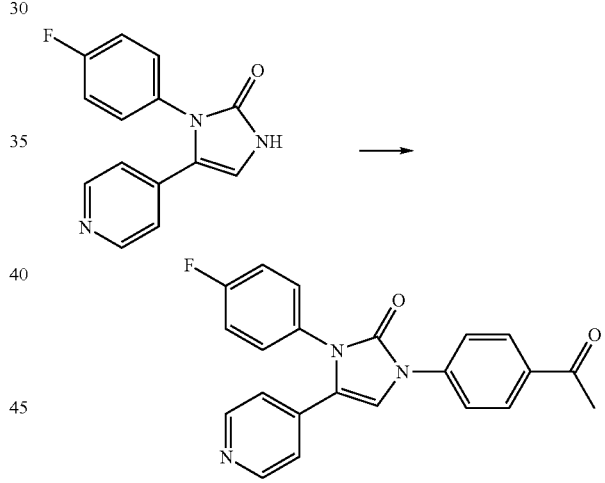

The compound of Example 1 (100 mg), 4-acetylphenylboronic acid (129 mg), copper (II) acetate (72 mg) and triethylamine (220 μl) were suspended in 10 ml of methylene chloride, and the suspension was stirred at room temperature for 24 hours. To the reaction mixture, 28% aqueous ammonia was added and the mixture was extracted with chloroform, washed with brine, and dried over anhydrous magnesium sulfate. The resultant mixture was concentrated under reduced pressure, and ether was added to the residue and precipitated crystals were collected by filtration to give 92 mg of the title compound. Melting point: 206° C. (decomposed)

Examples 388 to 389

The compound of Example 1 and the corresponding starting materials were reacted in the same manner as in Example 387 to give the compounds shown in Table 42.

TABLE 42

[Structure with F-phenyl, imidazolone, pyridyl-R², and N—CH₂—R¹]

| Examples | R¹ | Melting point (° C.) |
|---|---|---|
| 388 | 4-Pyridyl | 189 |
| 389 | 3-Thienyl | 193-195 |

Example 390

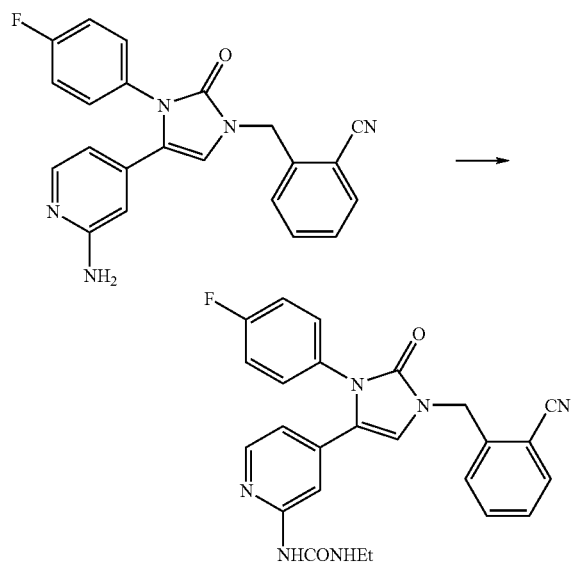

To a solution of the compound of Example 13 (50 mg) in THF was added ethyl isocyanate (12 µl), and the mixture was stirred at room temperature for 6 hours. The reaction mixture was concentrated under reduced pressure and purified by silica gel column chromatography to give 19 mg of the title compound as colorless crystal. Melting point: 20.9-210° C.

Examples 391 to 394

The compound of Example 16 and the compounds prepared in the same manner as in Example 16 were subjected to hydrolysis followed by amidation according to the conventional methods, or subjected to reduction followed by mesylation and dimethylamination, to give the compounds shown in Table 43.

TABLE 43

[Structure with F-phenyl, imidazolone, pyridyl-R², and N—CH₂—R¹]

| Examples | R¹ | R² | Melting point (° C.) |
|---|---|---|---|
| 391 | 2-Cyanobenzyl | Carboxy | 135 (decomposed) |
| 392 | 2-Cyanobenzyl | Carbamoyl | 209-210 (decomposed) |
| 393 | 2-Fluorobenzyl | Hydroxymethyl | 157-158 (decomposed) |
| 394 | 2-Fluorobenzyl | Dimethylaminomethyl | 231-236 (decomposed) |

Examples 395 to 398

The corresponding starting materials were reacted in the manner as in Example 368 to give the compounds shown in 44.

TABLE 44

[Structure with F-phenyl, imidazolone, pyridyl-R², and N—CH₂—R¹]

| Examples | R¹ | R² | MS ([M + H]⁺) |
|---|---|---|---|
| 395* | Ethyl | trans-4-Hydroxycyclohexyl-methylamino | 412 |
| 396* | Isopropyl | trans-4-Hydroxycyclohexyl-methylamino | 426 |
| 397* | Ethyl | cis-4-Hydroxycyclohexyl-methylamino | 412 |
| 398* | Isopropyl | cis-4-Hydroxycyclohexyl-methylamino | 426 |

*Monohydrochloride

Examples 399 to 416

The compound of Reference example 5(4) and the corresponding starting materials were reacted in the same manner as in Reference example 1(6), oxidized with 3-chloroperbenzoic acid in the same manner as in Reference example 6(2), subsequently reacted with the corresponding amine in the same manner as in Example 17, and, if necessary, subjected to removal of t-butoxycarbonyl in the same manner as in Example 80 to give the compounds in Tables 45 and 46.

TABLE 45

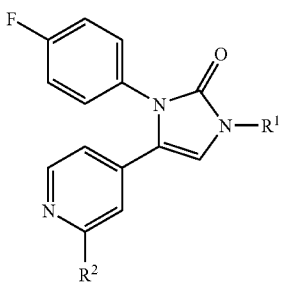

| Example | R¹ | R² | MS ([M + H]⁺) |
|---|---|---|---|
| 399* | Ethyl | 1,1-Dioxotetrahydrothiophen-3-ylamino | 418 |
| 400* | Ethyl | trans-4-(Methylcarbamoyl)cyclohexylamino | 439 |
| 401* | Ethyl | 1,5-Dimethyl-5-hydroxyhexylamino | 428 |
| 402* | Isopropyl | 1,5-Dimethyl-5-hydroxyhexylamino | 442 |
| 403* | Ethyl | cis-4-Hydroxy-4-methylcyclohexylamino | 412 |
| 404* | Isopropyl | trans-4-Hydroxy-4-methylcyclohexylamino | 426 |
| 405* | Isopropyl | trans-4-(1-Hydroxy-1-methylethyl)cyclohexylamino | 454 |
| 406* | Ethyl | trans-4-Hydroxy-4-methylcyclohexylamino | 412 |
| 407* | Isopropyl | cis-4-Hydroxy-4-methylcyclohexylamino | 426 |

*monohydrochloride

TABLE 46

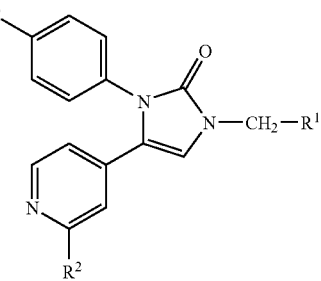

| Example | R¹ | R² | MS ([M + H]⁺) |
|---|---|---|---|
| 408* | Ethyl | trans-4-(1-Hydroxy-1-methylethyl)cyclohexylamino | 440 |
| 409* | Ethyl | (S)-1,2-Dimethyl-2-hydroxypropylamino | 386 |
| 410* | Isopropyl | (S)-1,2-Dimethyl-2-hydroxypropylamino | 400 |
| 411* | Ethyl | 1,3-Dimethyl-3-hydroxybutylamino | 400 |
| 412* | Isopropyl | 1,3-Dimethyl-3-hydroxybutylamino | 414 |
| 413* | Isopropyl | 2-Mercapto-2-methylpropylamino | 402 |
| 414* | Isopropyl | 1,1-Bishydroxymethylpropylamino | 416 |
| 415* | Isopropyl | 2-Hydroxy-2-methylpropylamino | 386 |
| 416** | Ethyl | 4-Piperidylamino | 383 |

*monohydrochloride;
**dihydrochloride

Examples 417 to 433

The compound of Reference example 5(4) was reacted in the same manner as in Example 2 or Reference example 1(6), reacted with methymagnesium bromide if necessary, subsequently oxidized with 3-chloroperbenzoic acid in the same manner as in Reference example 6(2), and reacted with the corresponding amine in the same manner as in Example 17 to give the compounds in Tables 47 and 48.

TABLE 47

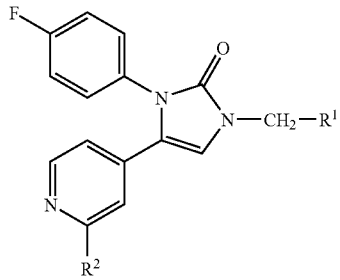

| Example | R¹ | R² | MS ([M + H]⁺) |
|---|---|---|---|
| 417* | 1,2-Dimethyl-2-hydroxypropyl | Isopropylamino | 400 |
| 418* | 1,2-Dimethyl-2-hydroxypropyl | cis-4-Hydroxy-4-methylcyclohexylamino | 470 |
| 419* | 1,2-Dimethyl-2-hydroxypropyl | (S)-1,2-Dimethyl-2-hydroxypropylamino | 444 |
| 420* | 1,2-Dimethyl-2-hydroxypropyl | Trans-4-Hydroxy-4-methylcyclohexylamino | 470 |
| 421* | 2-Hydroxy-1,1,2-trimethylpropyl | Isopropylamino | 414 |
| 422* | 2-Hydroxy-1,1,2-trimethylpropyl | Trans-4-Hydroxy-4-methylcyclohexylamino | 484 |
| 423* | 3-Hydroxy-3-methylbutyl | Isopropylamino | 400 |
| 424* | 3-Hydroxy-3-methylbutyl | 1,1-Dimethyl-2-hydroxyethylamino | 430 |

*monohydrochloride

TABLE 48

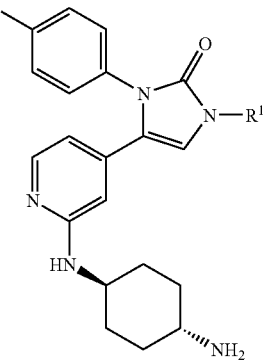

| Example | R¹ | R² | MS ([M + H]⁺) |
|---|---|---|---|
| 425* | 3-Hydroxy-3-methylbutyl | 2,2-Dimethyl-3-hydroxypropylamino | 444 |
| 426* | 3-Hydroxy-3-methylbutyl | 1-Hydroxymethylcyclopentylamino | 456 |
| 427* | 3-Hydroxy-3-methylbutyl | trans-4-Hydroxy-4-methylcyclohexylamino | 470 |

TABLE 48-continued

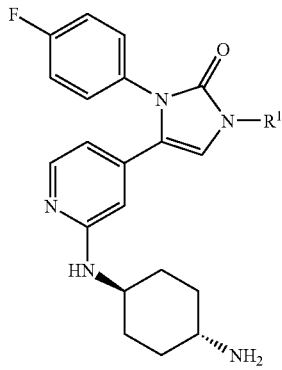

| Example | R¹ | R² | MS ([M + H]⁺) |
|---|---|---|---|
| 428* | 3-Hydroxy-3-methylbutyl | 4-Tetrahydropyranylamino | 442 |
| 429* | 3-Hydroxy-3-methylbutyl | (R)-1,2-Dimethyl-2-hydroxypropylamino | 444 |
| 430* | 3-Hydroxy-3-methylbutyl | (S)-1,2-Dimethyl-2-hydroxypropylamino | 444 |
| 431* | 3-Hydroxy-3-methylbutyl | trans-4-Hydroxycyclohexylamino | 456 |
| 432* | 3-Hydroxy-3-methylbutyl | 1-Methanesulfonylpiperidin-4-ylamino | 519 |
| 433* | 3-Hydroxy-3-methylbutyl | 1-Ethanesulfonylpiperidin-4-ylamino | 533 |

*monohydrochloride

Examples 434 to 460

The compound of Reference example 5(3) and the corresponding starting materials were reacted in the same manner as in Reference example 9, oxidized with 3-chloroperbenzoic acid in the same manner as in Reference example 6(2), and subsequently reacted with the corresponding compound in the same manner as in Example 17 to give the compounds in Tables 49 to 51.

TABLE 49

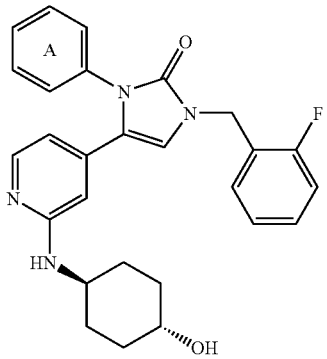

| Example | R¹ | R² | MS ([M + H]⁺) |
|---|---|---|---|
| 434* | 4-Tetrahydropyranyl | Isobutylamino | 412 |
| 435* | 4-Tetrahydropyranyl | Isopropylamino | 398 |

TABLE 49-continued

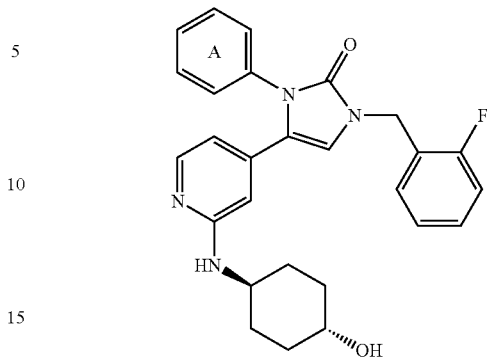

| Example | R¹ | R² | MS ([M + H]⁺) |
|---|---|---|---|
| 436* | 4-Tetrahydropyranyl | trans-4-Hydroxy-4-methylcyclohexylamino | 468 |
| 437* | 4-Tetrahydropyranyl | Cyclopropylamino | 396 |
| 438* | 4-Tetrahydropyranyl | 2,2-Dimethylpropylamino | 426 |
| 439* | 1-Acetylpiperidin-4-yl | trans-4-Hydroxy-4-methylcyclohexylamino | 509 |
| 440* | 1-Acetylpiperidin-4-yl | 2,2-Dimethylpropylamino | 467 |
| 441* | 1-Acetylpiperidin-4-yl | Isopropylamino | 439 |
| 442* | 1-Acetylpiperidin-4-yl | Isobutylamino | 453 |
| 443* | 1-Acetylpiperidin-4-yl | Cyclopropylamino | 437 |
| 444* | 4-Tetrahydropyranyl | (R)-1,2-Dimethyl-2-hydroxypropylamino | 442 |
| 445* | 4-Tetrahydropyranyl | (S)-1,2-Dimethyl-2-hydroxypropylamino | 442 |
| 446* | 4-Tetrahydropyranyl | (S)-2-Hydroxy-1-methylethylamino | 414 |

*monohydrochloride

TABLE 50

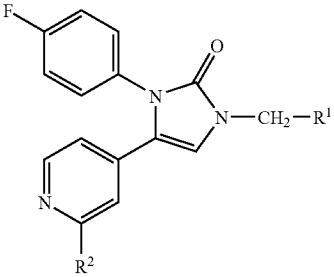

| Example | R¹ | R² | MS ([M + H]⁺) |
|---|---|---|---|
| 447* | 4-Tetrahydropyranyl | (S)-1-Hydroxymethylpropylamino | 428 |
| 448* | 4-Tetrahydropyranyl | 1,1-Dimethyl-2-hydroxyethylamino | 428 |
| 449* | 4-Tetrahydropyranyl | 4-Tetrahydropyranylamino | 440 |
| 450* | 1-Acetylpiperidin-4-yl | 1,1-Dimethyl-2-hydroxyethylamino | 469 |

TABLE 50-continued

Examples 451–453 (structure: 4-fluorophenyl-imidazolinone with pyridine bearing R², N-CH₂-R¹)

| Example | R¹ | R² | MS ([M + H]⁺) |
|---|---|---|---|
| 451* | 1-Acetylpiperidin-4-yl | 4-Tetrahydropyranylamino | 481 |
| 452* | 1-Acetylpiperidin-4-yl | (S)-1-Hydroxymethylpropylamino | 469 |
| 453* | 1-Acetylpiperidin-4-yl | (S)-1,2-Dimethyl-2-hydroxypropylamino | 483 |

*monohydrochloride

TABLE 51

| Example | R¹ | R² | MS ([M + H]⁺) |
|---|---|---|---|
| 454* | 4-Tetrahydropyranyl | trans-4-Hydroxycyclohexylamino | 454 |
| 455* | 1-Acetylpiperidin-4-yl | trans-4-Hydroxycyclohexylamino | 495 |
| 456* | 1-Methanesulfonyl-piperidin-4-yl | trans-4-Hydroxycyclohexylamino | 531 |
| 457* | 1-Methanesulfonyl-piperidin-4-yl | trans-4-Hydroxy-4-methylcyclohexylamino | 545 |
| 458* | 1-Methanesulfonyl-piperidin-4-yl | Isopropylamino | 475 |
| 459* | 4-Tetrahydropyranyl | 1-Methanesulfonyl-piperidin-4-ylamino | 517 |
| 460* | 1-Acetylpiperidin-4-yl | 1-Methanesulfonyl-piperidin-4-ylamino | 558 |

*monohydrochloride

Examples 461 to 476

The compound of Example 378 or Example 416 was subjected to alkylsulfonylation and acylation by the conventional manner, or reacted with isocyanate to give the compounds in Tables 52 and 53.

TABLE 52

| Example | R¹ | R² | MS ([M + H]⁺) |
|---|---|---|---|
| 461* | Isopropyl | 1-Acetylpiperidin-4-yl-amino | 439 |
| 462* | Isopropyl | 1-Methanesulfonylpiperidin-4-ylamino | 475 |
| 463* | Isopropyl | 1-(Isopropylsulfonyl)piperidin-4-ylamino | 503 |
| 464* | Isopropyl | 1-(Propylsulfonyl)piperidin-4-ylamino | 503 |
| 465* | Isopropyl | 1-(Butylsulfonyl)piperidin-4-ylamino | 517 |
| 466* | Isopropyl | 1-(Isobutyloxycarbonyl)piperidin-4-ylamino | 497 |
| 467* | Isopropyl | 1-butyrylpiperidin-4-ylamino | 467 |
| 468* | Ethyl | 1-Acetylpiperidin-4-ylamino | 425 |

*monohydrochloride

TABLE 53

| Example | R¹ | R² | MS ([M + H]⁺) |
|---|---|---|---|
| 469* | Ethyl | 1-Methanesulfonylpiperidin-4-ylamino | 461 |
| 470* | Ethyl | 1-Ethanesulfonylpiperidin-4-ylamino | 475 |
| 471* | Isopropyl | 1-Ethylcarbamoylpiperidin-4-ylamino | 468 |
| 472* | Isopropyl | 1-Propylcarbamoylpiperidin-4-ylamino | 482 |
| 473* | Isopropyl | 1-Isopropylcarbamoylpiperidin-4-ylamino | 482 |
| 474* | Isopropyl | 1-Ethanesulfonylpiperidin-4-ylamino | 489 |
| 475* | Isopropyl | 1-Methoxycarbonylpiperidin-4-ylamino | 455 |
| 476* | Isopropyl | 1-Ethoxycarbonylpiperidin-4-ylamino | 469 |

*monohydrochloride

Examples 477, 478

The compound of Example 147 was subjected to alkylsulfonylation by the conventional manner to give the compounds in Table 54.

TABLE 54

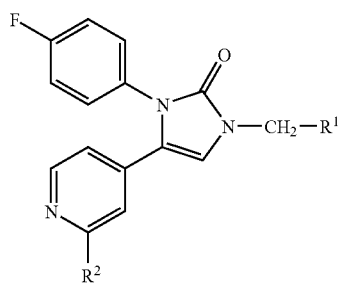

| Example | R¹ | R² | MS ([M + H]⁺) |
|---|---|---|---|
| 477* | 1-Methanesulfonyl-piperidin-4-yl | Isopropylamino | 474 |
| 478* | 1-Ethanesulfonyl piperidin-4-yl | Isopropylamino | 488 |

*monohydrochloride

In a similar manner to those described in the Examples above, the following compounds were prepared.

TABLE 55

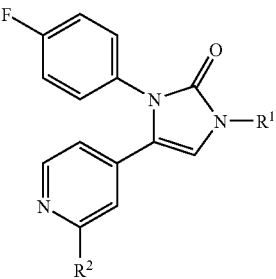

| Example | R¹ | R² | MS ([M + H]⁺) |
|---|---|---|---|
| 479* | 1-(methanesulfonyl) piperidin-4-yl | (1S)-1,2-Dimethyl-2-hydroxypropylamino | 519 |
| 480* | 2-Hydroxy-2-methylpropyl | 1-(Isopropylsulfonyl) piperidin-4-ylamino | 533 |
| 481 | Isopropyl | (3R)-3-pyrrolidinyl-amino | 383 |
| 482* | Isopropyl | (3R)-1-Methanesulfonyl-pyrrolidin-3-ylamino | 461 |
| 483* | Isobutyl | 1-(Ethanesulfonyl) piperidin-4-ylamino | 503 |
| 484* | Isobutyl | 1-(Isopropylsulfonyl) piperidin-4-ylamino | 517 |
| 485* | Cyclopropylmethyl | 1-(Methanesulfonyl) piperidin-4-ylamino- | 487 |
| 486* | Isopropyl | trans-4-(N-Methane-sulfonyl-N-methylamino) cyclohexylamino | 503 |
| 487* | 4-Tetrahydropyranyl | 1-(Ethanesulfonyl) piperidin-4-ylamino | 531 |
| 488* | 4-Tetrahydropyranyl | 1-(Isopropylsulfonyl) piperidin-4-ylamino | 545 |
| 489* | 4-Tetrahydropyranyl | 1-(Methoxycarbonyl) piperidin-4-ylamino | 497 |
| 490* | 4-Tetrahydropyranyl | 1-propionylpiperidin-4-ylamino | 495 |
| 491* | 4-Tetrahydropyranyl | 1-Acetylpiperidin-4-ylamino | 481 |

*monohydrochloride

TABLE 56

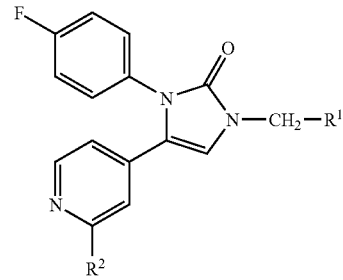

| Example | R¹ | R² | MS ([M + H]⁺) |
|---|---|---|---|
| 492* | Isobutyl | 1-Acetylpiperidin-4-ylamino | 453 |
| 493* | Methoxymethyl | 1-(Ethanesulfonyl)piperi-din-4-ylamino | 491 |
| 494* | Methoxymethyl | 1-(Isopropylsulfonyl) piperidin-4-ylamino | 505 |
| 495* | 4-Tetrahydro-pyranyl | 1-(Dimethylaminosulfonyl) piperidin-4-ylamino | 546 |
| 496* | 4-Tetrahydropy-ranyl | trans-4-(Methanesulfonyl-amino)cyclohexylamino | 531 |
| 497* | 2-hydroxy-2-methylpropyl | (1S)-1,2-Dimethyl-2-hydroxypropylamino | 430 |
| 498* | Cyclobutyl | trans-4-Hydroxycyclo-hexylamino | 424 |
| 499* | Cyclobutyl | trans-4-Methyl-4-hy-droxycyclohexylamino | 438 |
| 500* | Cyclobutyl | 1-(Methanesulfonyl)piperi-din-4-ylamino | 487 |
| 501* | Cyclobutyl | 1-(Ethanesulfonyl)piperi-din-4-ylamino | 501 |
| 502* | Cyclobutyl | 1-(Isopropylsulfonyl) piperidin-4-ylamino | 515 |
| 503* | Cyclobutyl | 1-(Dimethylaminosulfonyl) piperidin-4-ylamino | 516 |

*monohydrochloride

TABLE 57

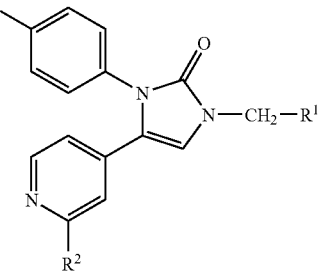

| Example | R¹ | R² | MS ([M + H]⁺) |
|---|---|---|---|
| 504* | 4-Tetrahydro-pyranyl | trans-4-(N-Methanesulfonyl-N-methylamino)cyclo-hexylamino | 545 |
| 505* | Cyclobutyl | (1S)-1,2-Dimethyl-2-hy-droxypropylamino | 412 |
| 506* | Isopropyl | (3S)-1-(Methanesulfonyl) piperidin-3-ylamino | 475 |
| 507* | Methoxymethyl | 1-(Dimethylaminosulfonyl) piperidin-4-ylamino | 506 |
| 508* | 2-Hydroxy-2-methylpropyl | 1-(Dimethylaminosulfonyl) piperidin-4-ylamino | 534 |
| 509* | 3-Hydroxy-3-methylbutyl | 1-(Dimethylaminosulfonyl) piperidin-4-ylamino | 548 |

TABLE 57-continued

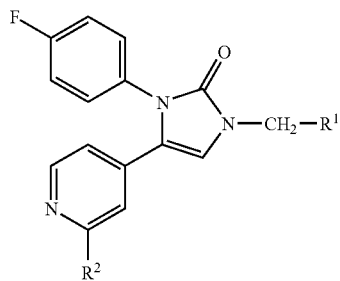

| Example | R¹ | R² | MS ([M + H]⁺) |
|---|---|---|---|
| 510* | 2-Hydroxy-2-methylpropyl | trans-4-(N-Methanesulfonyl-N-methylamino)cyclohexyl-amino | 533 |
| 511* | 3-Hydroxy-3-methylbutyl | trans-4-(N-Methanesulfonyl-N-methylamino)cyclohexylamino | 547 |
| 512* | 4-Tetrahydropyranyl | trans-4-(N-Ethyl-N-methanesulfonylamino)cyclohexylamino | 559 |
| 513 | Isopropyl | 3-Amino-2,2-dimethylpropylamino | 399 |
| 514 | Isopropyl | 2-amino-2-methylpropyl-amino | 385 |
| 515* | Isobutyl | trans-4-Hydroxy-4-methylcyclohexylamino | 440 |
| 516** | Cyclobutyl | trans-4-aminocyclohexylamino | 423 |

*monohydrochloride,
**dihydrochloride

TABLE 58

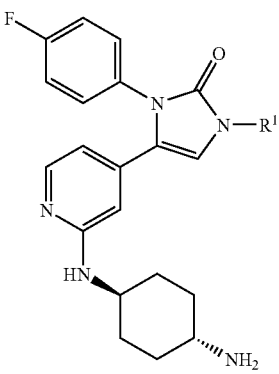

| Example | R¹ | R² | Ring A | MS ([M + H]⁺) |
|---|---|---|---|---|
| 517* | 1-Acetyl-piperidin-4-yl | trans-4-Hydroxy-4-methylcyclohexylamino | 3-Methyl-phenyl | 505 |
| 518* | 4-Tetrahydropyranyl | (1S)-1,2-Dimethyl-2-hydroxypropylamino | 3-Methylphenyl | 438 |
| 519* | 4-Tetrahydropyranyl | (1S)-1,2-Dimethyl-2-hydroxypropylamino | 3-Chlorophenyl | 458 |
| 520* | 4-Tetrahydropyranyl | trans-4-Hydroxycyclohexylamino | 3-Methylphenyl | 207-209 °C.(melting point) |
| 521* | 4-Tetrahydropyranyl | trans-4-Hydroxy-4-methylcyclohexylamino | 3-Methylphenyl | 212-214 °C.(melting point) |

TABLE 58-continued

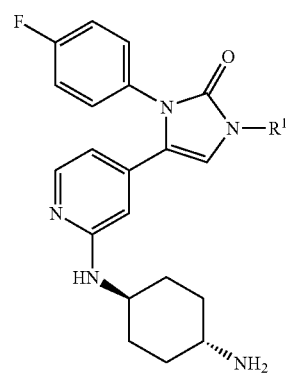

| Example | R¹ | R² | Ring A | MS ([M + H]⁺) |
|---|---|---|---|---|
| 522* | 4-Tetrahydropyranyl | trans-4-Hydroxy-4-methylcyclohexylamino | 4-Chlorophenyl | 195-199 °C.(melting point) |
| 523* | 4-Tetrahydropyranyl | trans-4-Hydroxycyclohexylamino | 4-Chlorophenyl | 272-275 °C.(melting point) |
| 524* | 4-Tetrahydropyranyl | trans-4-Hydroxy-4-methylcyclohexylamino | 3-Chlorophenyl | 213-215 °C.(melting point) |
| 525 | 4-Tetrahydropyranyl | trans-4-Hydroxy-4-methylcyclohexylamino | 4-Fluorophenyl | 233-236 °C.(melting point) |

*monohydrochloride

TABLE 59

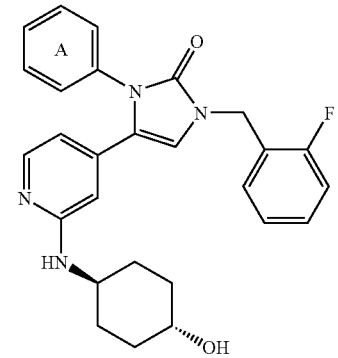

| Example | R¹ | R² | MS ([M + H]⁺) |
|---|---|---|---|
| 526* | 4-Tetrahydropyranyl | 1,1-Dioxotetrahydrothiopyran-4-ylamino | 488 |
| 527* | Isopropyl | 2-Acetylamino-2-methylpropylamino | 427 |
| 528* | Isopropyl | 2-Methanesulfonylamino-2-methylpropylamino | 463 |
| 529* | Isopropyl | 3-Acetylamino-2,2-dimethylpropylamino | 441 |
| 530* | Isopropyl | 2,2-Dimethyl-3-methanesulfonylaminopropylamino | 477 |
| 531* | Cyclopentyl | trans-4-Hydroxymethylcyclohexylamino | 452 |
| 532* | Cyclopentyl | 1-Ethanesulfonylpiperidin-4-ylamino | 515 |

*monohydrochloride

TABLE 60

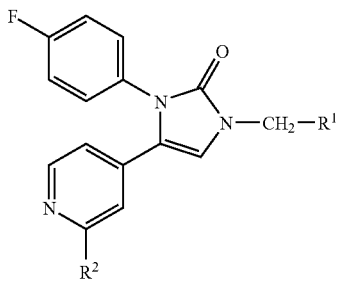

| Example | R¹ | R² | MS ([M + H]⁺) |
|---|---|---|---|
| 533* | Cyclopentyl | 1-Isopropylsulfonylpiperidin-4-ylamino | 529 |
| 534* | Cyclopentyl | 1-Methanesulfonylpiperidin-4-ylamino | 501 |
| 535* | Cyclopentyl | 4-Tetrahydropyranylamino | 424 |
| 536* | Cyclopentyl | trans-4-Hydroxy-4-methylcyclohexylamino | 452 |
| 537* | Cyclopentyl | (1S)-1,2-Dimethyl-2-hydroxypropylamino | 426 |
| 538* | Cyclopentyl | 1,1-Dimethyl-2-hydroxyethylamino | 412 |
| 539* | Cyclopentyl | 2,2-Dimethyl-3-hydroxypropylamino | 426 |
| 540* | Cyclopentyl | trans-4-Hydroxycyclohexylamino | 438 |
| 541* | Cyclopentyl | trans-4-aminocyclohexylamino | 437 |
| 542* | Cyclohexyl | trans-4-hydroxymethylcyclohexylamino | 466 |
| 543* | Cyclohexyl | 1-Ethanesulfonylpiperidin-4-ylamino | 529 |
| 544* | Cyclohexyl | 1-Isopropylsulfonylpiperidin-4-ylamino | 543 |

*monohydrochloride

TABLE 61

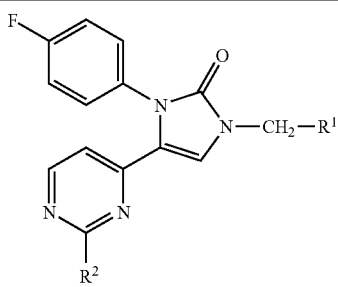

| Example | R¹ | R² | MS ([M + H]⁺) |
|---|---|---|---|
| 545* | Cyclohexyl | 1-Methanesulfonylpiperidin-4-ylamino | 515 |
| 546* | Cyclohexyl | 4-Tetrahydropyranylamino | 438 |
| 547* | Cyclohexyl | trans-4-Hydroxy-4-methylcyclohexylamino | 466 |
| 548* | Cyclohexyl | (1S)-1,2-Dimethyl-2-hydroxypropylamino | 440 |
| 549* | Cyclohexyl | 1,1-Dimethyl-2-hydroxyethylamino | 426 |
| 550* | Cyclohexyl | 2,2-Dimethyl-3-hydroxypropylamino | 440 |
| 551* | Cyclohexyl | trans-4-Hydroxycyclohexylamino | 452 |
| 552* | Cyclohexyl | trans-4-aminocyclohexylamino | 451 |

TABLE 61-continued

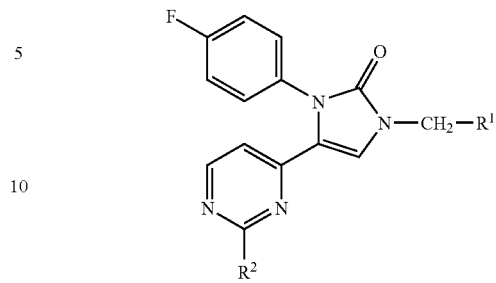

| Example | R¹ | R² | MS ([M + H]⁺) |
|---|---|---|---|
| 553* | Isopropyl | 2,2-Dimethyl-3-(N-methanesulfonyl-N-methylamino)propylamino | 491 |
| 554* | Isopropyl | 2-(N-Methanesulfonyl-N-methylamino)-2-methylpropylamino | 477 |

*monohydrochloride

TABLE 62

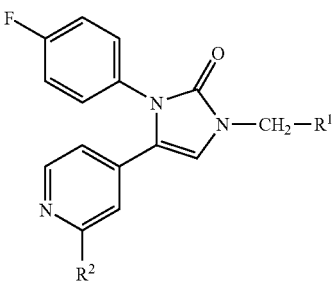

| Example | R¹ | R² | Ring A | MS ([M + H]⁺) |
|---|---|---|---|---|
| 555* | 4-Tetrahydropyranyl | 1-Methanesulfonylpiperidin-4-ylamino | 3-Methylphenyl | 513 |
| 556* | 4-Tetrahydropyranyl | 1-Methanesulfonylpiperidin-4-ylamino | 3-Chlorophenyl | 533 |

*monohydrochloride

In a similar manner to those described in the Examples above, the following compounds are prepared.

TABLE 63

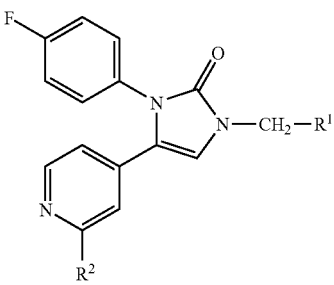

| No. | R¹ | R² | Ring A |
|---|---|---|---|
| 1 | 4-Tetrahydropyranyl | 1-Acetyl-4-methylpiperidin-4-ylamino | 4-Fluorophenyl |
| 2 | 4-Tetrahydropyranyl | 1-Methanesulfonyl-4-methylpiperidin-4-ylamino | 4-Fluorophenyl |

TABLE 63-continued

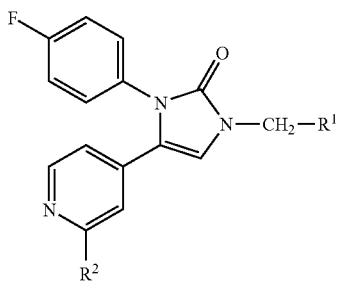

| No. | R¹ | R² | Ring A |
|---|---|---|---|
| 3 | 4-Tetrahydropyranyl | trans-4-amino-4-methyl-cyclohexylamino | 4-Fluorophenyl |
| 4 | 4-Tetrahydropyranyl | trans-4-Methoxycyclo-ylamino | 4-Fluorophenyl |
| 5 | 4-Tetrahydropyranyl | trans-4-Hydroxymethyl-cyclohexylamino | 4-Fluorophenyl |
| 6 | 4-Tetrahydropyranyl | trans-4-(1-Hydroxy-1-methyl-ethyl) cyclohexylamino | 4-Fluorophenyl |
| 7 | 4-Tetrahydropyranyl | cis-4-Hydroxycyclohexyl-methylamino | 4-Fluorophenyl |
| 8 | 4-Tetrahydropyranyl | cis-4-Hydroxy-4-methyl-cyclohexylmethylamino | 4-Fluorophenyl |
| 9 | 4-Tetrahydropyranyl | 1-Acetyl-4-methylpiperi-din-4-ylamino | 3-Methylphenyl |
| 10 | 4-Tetrahydropyranyl | 1-Methanesulfonyl-4-methylpiperidin-4-ylamino | 3-Methylphenyl |
| 11 | 4-Tetrahydropyranyl | trans-4-amino-4-methyl-cyclohexylamino | 3-Methylphenyl |
| 12 | 4-Tetrahydropyranyl | trans-4-Methoxycyclo-hexylamino | 3-Methylphenyl |
| 13 | 4-Tetrahydropyranyl | trans-4-Hydroxymethyl-cyclohexylamino | 3-Methylphenyl |

TABLE 64

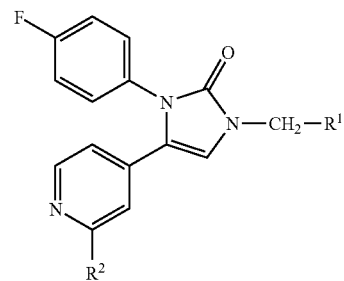

| No. | R¹ | R² | Ring A |
|---|---|---|---|
| 14 | 4-Tetrahydropyranyl | trans-4-(1-Hydroxy-1-methylethyl)cyclohexylamino | 3-Methylphenyl |
| 15 | 4-Tetrahydropyranyl | cis-4-Hydroxycyclohexyl-methylamino | 3-Methylphenyl |
| 16 | 4-Tetrahydropyranyl | cis-4-Hydroxy-4-methyl-cyclohexylmethylamino | 3-Methylphenyl |
| 17 | 4-Tetrahydropyranyl | 1-Acetyl-4-methylpiperi-din-4-ylamino | 3-Chlorophenyl |
| 18 | 4-Tetrahydropyranyl | 1-Methanesulfonyl-4-methylpiperidin-4-ylamino | 3-Chlorophenyl |
| 19 | 4-Tetrahydropyranyl | trans-4-amino-4-methyl-cyclohexylamino | 3-Chlorophenyl |
| 20 | 4-Tetrahydropyranyl | trans-4-Methoxycyclo-hexylamino | 3-Chlorophenyl |
| 21 | 4-Tetrahydropyranyl | trans-4-Hydroxymethyl-cyclohexylamino | 3-Chlorophenyl |
| 22 | 4-Tetrahydropyranyl | trans-4-(1-Hydroxy-1-methylethyl)cyclohexylamino | 3-Chlorophenyl |
| 23 | 4-Tetrahydropyranyl | cis-4-Hydroxycyclohexyl methylamino | 3-Chlorophenyl |
| 24 | 4-Tetrahydropyranyl | cis-4-Hydroxy-4-methyl cyclohexylmethylamino | 3-Chlorophenyl |
| 25 | 4-Tetrahydropyranyl | 1-Acetylpiperidin-4-ylamino | 3-Trifluoro-methylphenyl |

TABLE 65

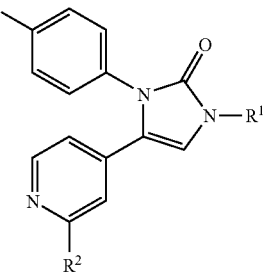

| No. | R¹ | R² | Ring A |
|---|---|---|---|
| 26 | 4-Tetrahydropyranyl | 1-Methanesulfonylpiperi-din-4-ylamino | 3-Trifluoromethyl-phenyl |
| 27 | 4-Tetrahydropyranyl | 1-Ethanesulfonylpiperi-din-4-ylamino | 3-Trifluoro-methylphenyl |
| 28 | 4-Tetrahydropyranyl | 1-Isopropylsulfonylpiperi-din-4-ylamino | 3-Trifluoro-methylphenyl |
| 29 | 4-Tetrahydropyranyl | 1-Acetyl-4-methylpiperi-din-4-ylamino | 3-Trifluoro-methylphenyl |
| 30 | 4-Tetrahydropyranyl | 1-Methanesulfonyl-4-methylpiperidin-4-ylamino | 3-Trifluoro-methylphenyl |
| 31 | 4-Tetrahydropyranyl | trans-4-Amino-4-methyl cyclohexylamino | 3-Trifluoro-methylphenyl |
| 32 | 4-Tetrahydropyranyl | trans-4-Hydroxycyclo-hexylamino | 3-Trifluoro-methylphenyl |
| 33 | 4-Tetrahydropyranyl | trans-4-Methoxycyclo-hexylamino | 3-Trifluoro-methylphenyl |
| 34 | 4-Tetrahydropyranyl | trans-4-Hydroxy-4-methylcyclohexylamino | 3-Trifluoro-methylphenyl |
| 35 | 4-Tetrahydropyranyl | cis-4-Hydroxycyclo-hexylmethylamino | 3-Trifluoro-methylphenyl |
| 36 | 4-Tetrahydropyranyl | cis-4-Hydroxy-4-methyl cyclohexylmethylamino | 3-Trifluoro-methylphenyl |
| 37 | 4-Tetrahydropyranyl | (1S)-1,2-Dimethyl-2-hydroxypropylamino | 3-Trifluoro-methylphenyl |
| 38 | 4-Tetrahydropyranylmethyl | 1-Acetylpiperidin-4-ylamino | 4-Fluorophenyl |

TABLE 66

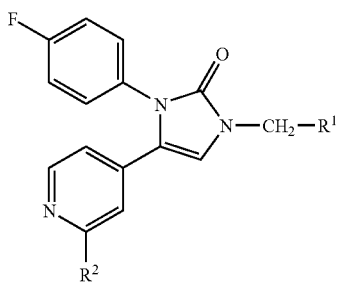

| No. | R¹ | R² | Ring A |
|---|---|---|---|
| 39 | 4-Tetrahydropyranylmethyl | 1-Methanesulfonylpiperidin-4-ylamino | 4-Fluorophenyl |
| 40 | 4-Tetrahydropyranylmethyl | 1-Ethanesulfonylpiperidin-4-ylamino | 4-Fluorophenyl |
| 41 | 4-Tetrahydropyranylmethyl | 1-Isopropylsulfonylpiperidin-4-ylamino | 4-Fluorophenyl |
| 42 | 4-Tetrahydropyranylmethyl | 1-Acetyl-4-methylpiperidin-4-ylamino | 4-Fluorophenyl |
| 43 | 4-Tetrahydropyranylmethyl | 1-Methanesulfonyl-4-methylpiperidin-4-ylamino | 4-Fluorophenyl |
| 44 | 4-Tetrahydropyranylmethyl | trans-4-Amino-4-methylcyclohexylamino | 4-Fluorophenyl |
| 45 | 4-Tetrahydropyranylmethyl | trans-4-Methoxycyclohexylamino | 4-Fluorophenyl |
| 46 | 4-Tetrahydropyranylmethyl | trans-4-Hydroxy-4-methylcyclohexylamino | 4-Fluorophenyl |
| 47 | 4-Tetrahydropyranylmethyl | trans-4-(N-methanesulfonyl-N-methylamino)cyclohexylamino | 4-Fluorophenyl |
| 48 | 4-Tetrahydropyranylmethyl | cis-4-Hydroxycyclohexylmethylamino | 4-Fluorophenyl |
| 49 | 4-Tetrahydropyranylmethyl | cis-4-Hydroxy-4-methylcyclohexylmethylamino | 4-Fluorophenyl |
| 50 | 4-Tetrahydropyranylmethyl | (1S)-1,2-Dimethyl-2-hydroxypropylamino | 4-Fluorophenyl |
| 51 | 4-Tetrahydropyranylmethyl | 2,2-Dimethyl-3-hydroxypropylamino | 4-Fluorophenyl |

TABLE 67

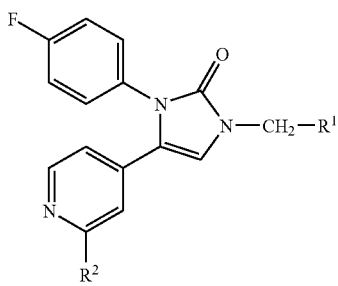

| No. | R¹ | R² | Ring A |
|---|---|---|---|
| 52 | 3-Tetrahydrofuryl | 1-Acetylpiperidin-4-ylamino | 4-Fluorophenyl |
| 53 | 3-Tetrahydrofuryl | 1-Methanesulfonylpiperidin-4-ylamino | 4-Fluorophenyl |
| 54 | 3-Tetrahydrofuryl | 1-Ethanesulfonylpiperidin-4-ylamino | 4-Fluorophenyl |
| 55 | 3-Tetrahydrofuryl | 1-Isopropylsulfonylpiperidin-4-ylamino | 4-Fluorophenyl |
| 56 | 3-Tetrahydrofuryl | 1-Acetyl-4-methylpiperidin-4-ylamino | 4-Fluorophenyl |
| 57 | 3-Tetrahydrofuryl | 1-Methanesulfonyl-4-methylpiperidin-4-ylamino | 4-Fluorophenyl |
| 58 | 3-Tetrahydrofuryl | trans-4-Amino-4-methylcyclohexylamino | 4-Fluorophenyl |

TABLE 67-continued

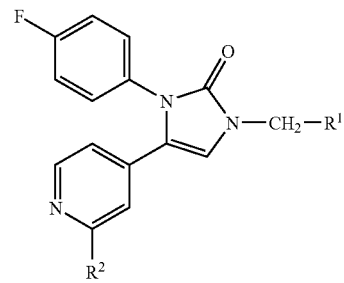

| No. | R¹ | R² | Ring A |
|---|---|---|---|
| 59 | 3-Tetrahydrofuryl | trans-4-Methoxycyclohexylamino | 4-Fluorophenyl |
| 60 | 3-Tetrahydrofuryl | trans-4-Hydroxycyclohexylamino | 4-Fluorophenyl |
| 61 | 3-Tetrahydrofuryl | trans-4-Hydroxy-4-methylmethylcyclohexylamino | 4-Fluorophenyl |
| 62 | 3-Tetrahydrofuryl | trans-4-(N-methanesulfonyl-N-methylamino)cyclohexylamino | 4-Fluorophenyl |
| 63 | 3-Tetrahydrofuryl | cis-4-Hydroxycyclohexylmethylamino | 4-Fluorophenyl |
| 64 | 3-Tetrahydrofuryl | cis-4-Hydroxy-4-methylcyclohexylmethylamino | 4-Fluorophenyl |

TABLE 68

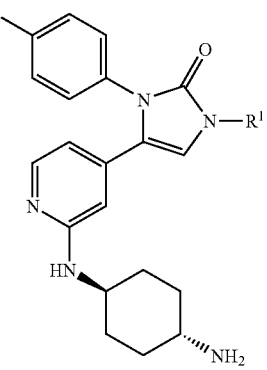

| No. | R¹ | R² | Ring A |
|---|---|---|---|
| 65 | 3-Tetrahydrofuryl | (1S)-1,2-Dimethyl-2-hydroxypropylamino | 4-Fluorophenyl |
| 66 | 3-Tetrahydrofuryl | 2,2-Dimethyl-3-hydroxypropylamino | 4-Fluorophenyl |
| 67 | 1-Methylpropyl | 1-Acetylpiperidin-4-ylamino | 4-Fluorophenyl |
| 68 | 1-Methylpropyl | 1-Methanesulfonylpiperidin-4-ylamino | 4-Fluorophenyl |
| 69 | 1-Methylpropyl | 1-Ethanesulfonylpiperidin-4-ylamino | 4-Fluorophenyl |
| 70 | 1-Methylpropyl | 1-Isopropylsulfonylpiperidin-4-ylamino | 4-Fluorophenyl |
| 71 | 1-Methylpropyl | 1-Acetyl-4-methylpiperidin-4-ylamino | 4-Fluorophenyl |
| 72 | 1-Methylpropyl | 1-Methanesulfonyl-4-methylpiperidin-4-ylamino | 4-Fluorophenyl |
| 73 | 1-Methylpropyl | trans-4-Amino-4-methylcyclohexylamino | 4-Fluorophenyl |
| 74 | 1-Methylpropyl | trans-4-Methoxycyclohexylamino | 4-Fluorophenyl |
| 75 | 1-Methylpropyl | trans-4-Hydroxycyclohexylamino | 4-Fluorophenyl |
| 76 | 1-Methylpropyl | trans-4-Hydroxy-4-methylcyclohexylamino | 4-Fluorophenyl |

TABLE 69

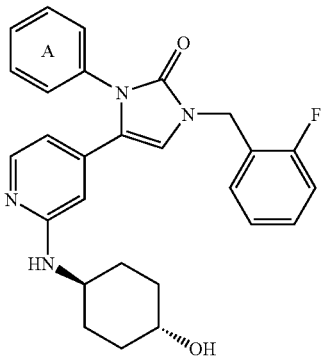

| No. | R¹ | R² | Ring A |
|---|---|---|---|
| 77 | 1-Methylpropyl | trans-4-(N-methanesulfonyl-N-methylamino)cyclohexylamino | 4-Fluorophenyl |
| 78 | 1-Methylpropyl | cis-4-Hydroxycyclohexylmethylamino | 4-Fluorophenyl |
| 79 | 1-Methylpropyl | cis-4-Hydroxy-4-methylcyclohexylmethylamino | 4-Fluorophenyl |
| 80 | 1-Methylpropyl | (1S)-1,2-Dimethyl-2-hydroxypropylamino | 4-Fluorophenyl |

TABLE 69-continued

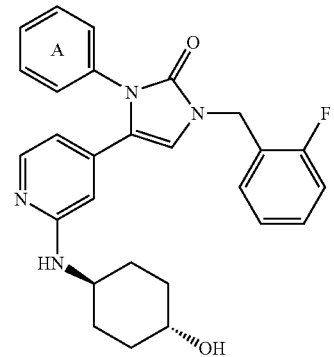

| No. | R¹ | R² | Ring A |
|---|---|---|---|
| 81 | 1-Methylpropyl | 2,2-Dimethyl-3-hydroxypropylamino | 4-Fluorophenyl |

According to the production methods described in the above Examples and the present specification and methods conventionally employed in the field of organic synthetic chemistry, compounds, which is respectively combined with each of the substitutents shown in Tables 70 to 77, can be produced.

TABLE 70

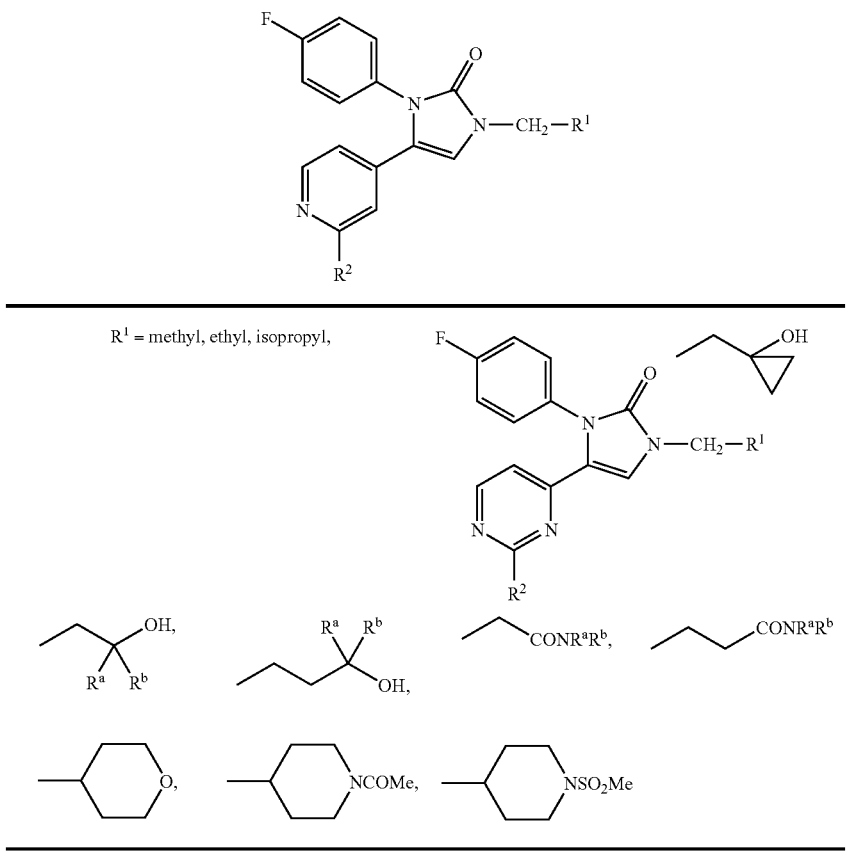

TABLE 70-continued
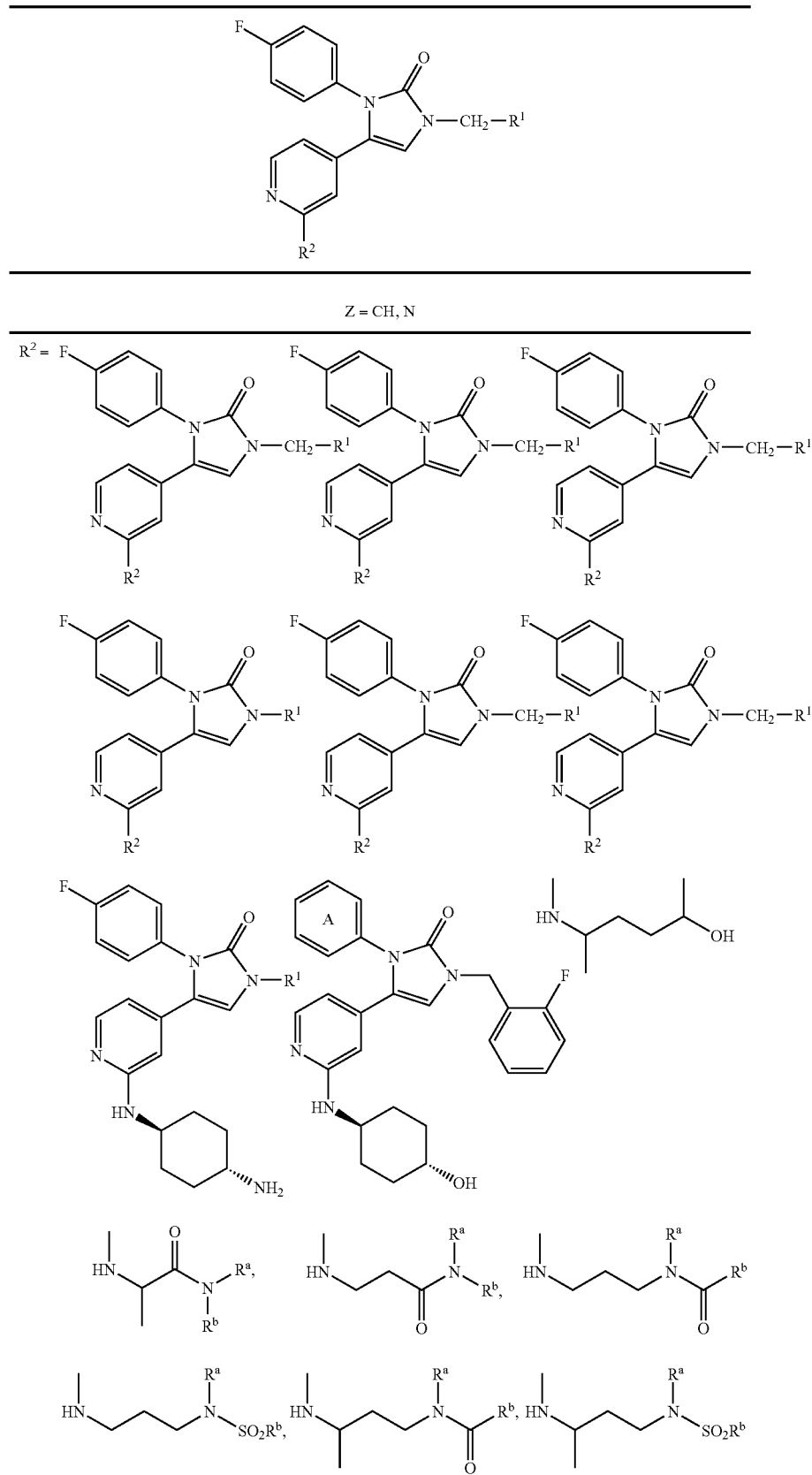
Z = CH, N

TABLE 70-continued
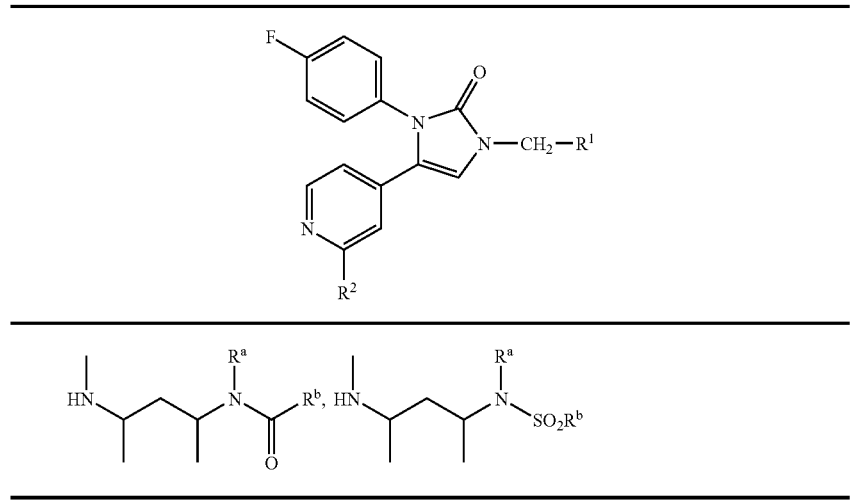
$R^a$, $R^b$ = each independently, hydrogen, $C_1$~$C_3$ alkyl
TABLE 71
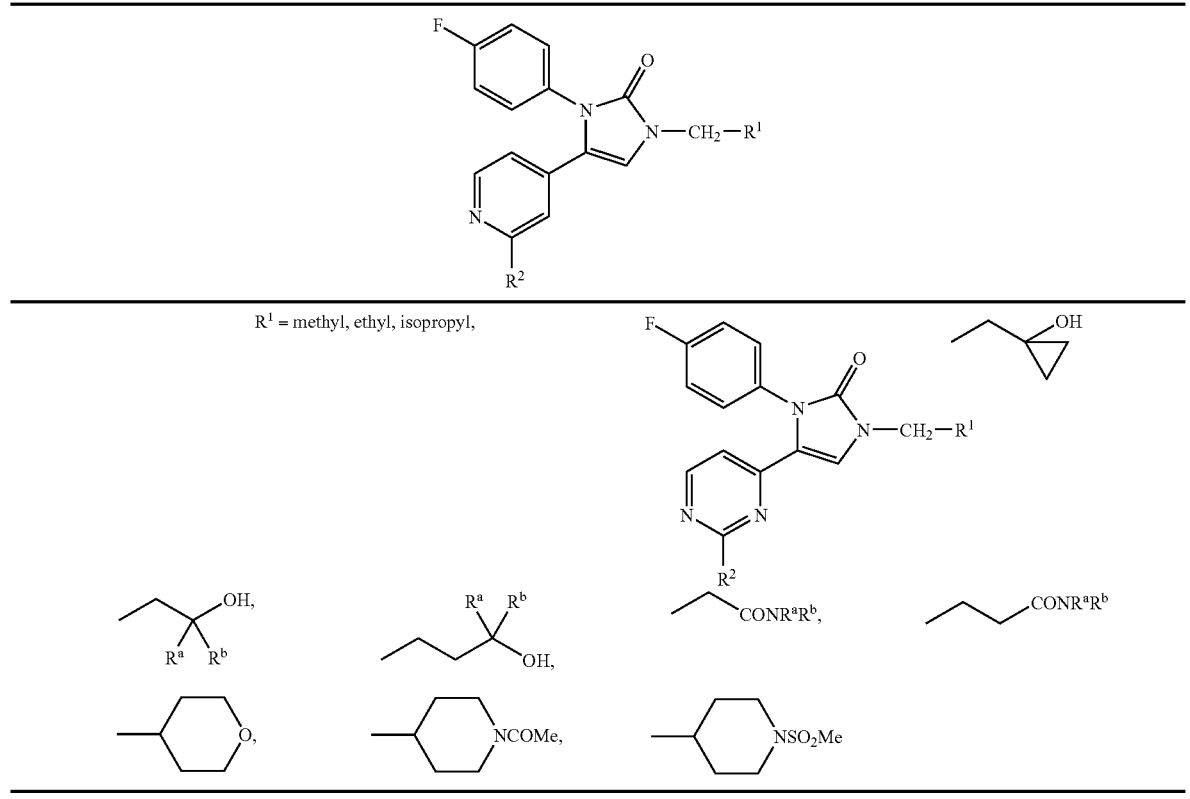
$R^1$ = methyl, ethyl, isopropyl,
Z = CH, N
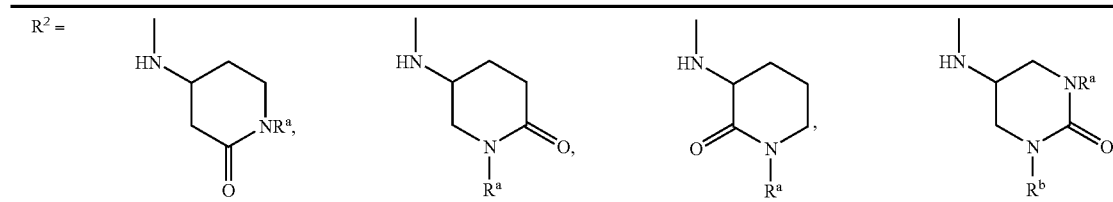

TABLE 71-continued
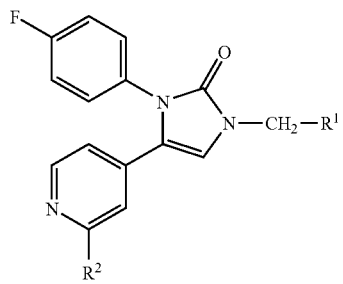
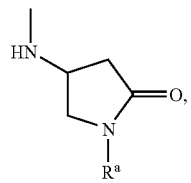 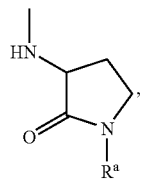 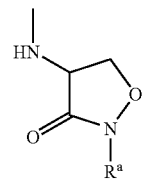 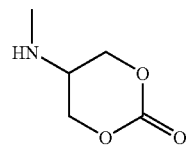
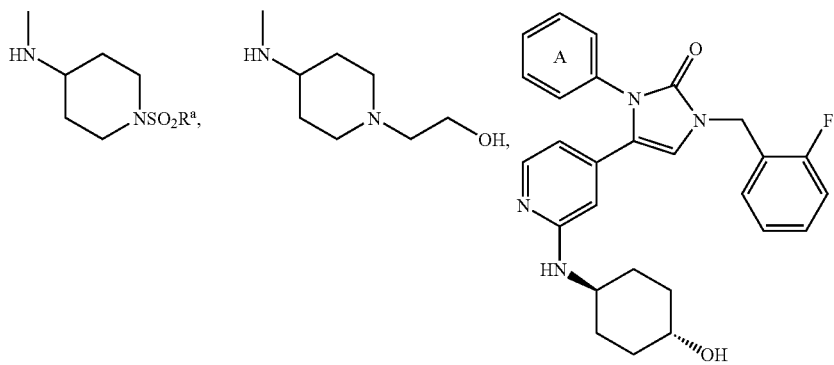
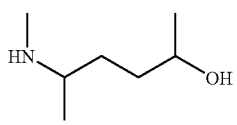
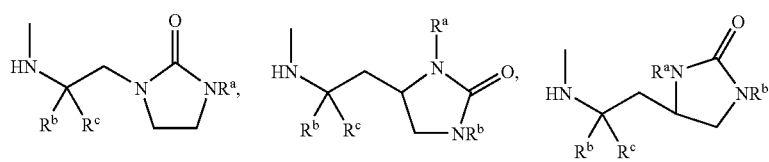
$R^a$, $R^b$, $R^c$, $R^d$ = each independently, hydrogen, $C_1$~$C_3$ alkyl TABLE 72
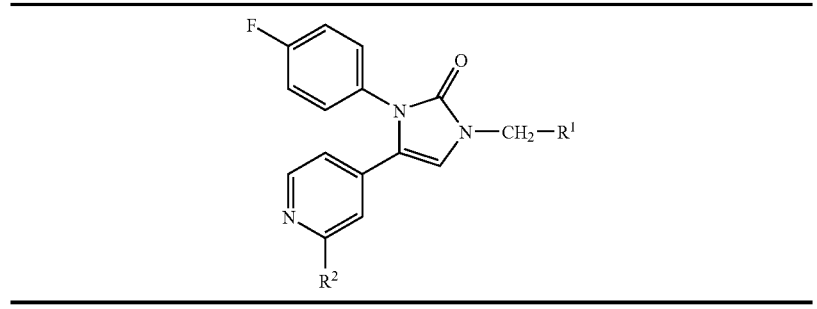
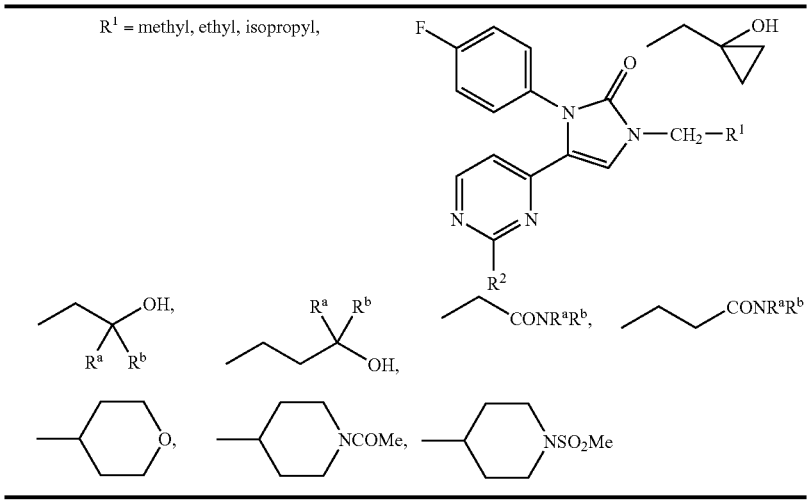
Z = CH, N
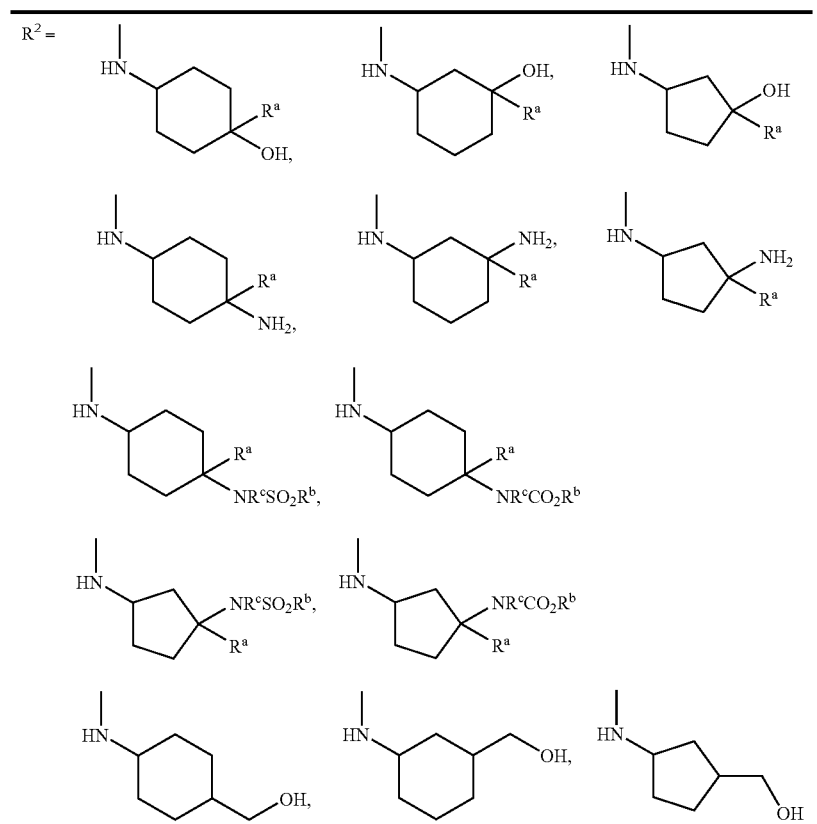

TABLE 72-continued
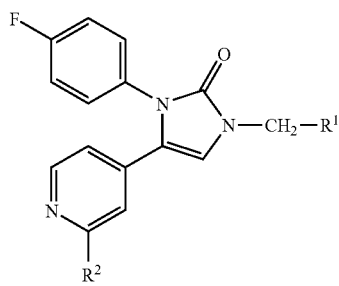
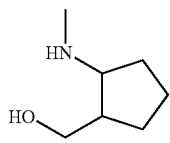
$R^a$, $R^b$, $R^c$, $R^d$ = each independently, hydrogen, $C_1\sim C_3$ alkyl
TABLE 73
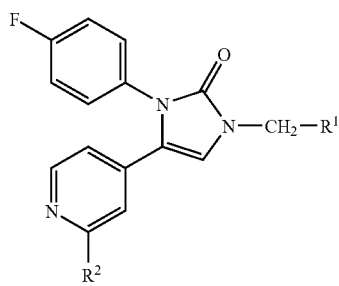
$R^1$ = methyl, ethyl, isopropyl, 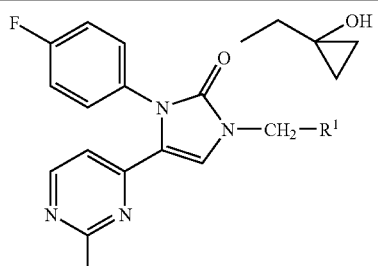
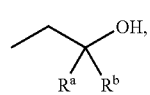 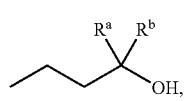 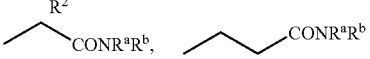
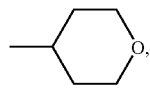 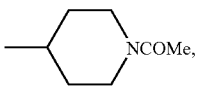 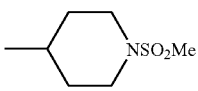
Z = CH, N
$R^2$ = 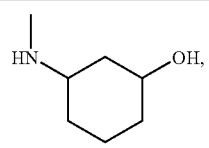 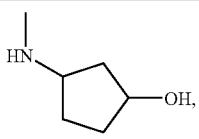 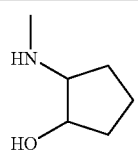

TABLE 73-continued
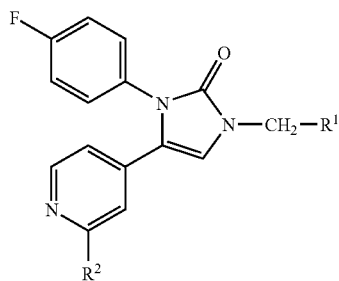
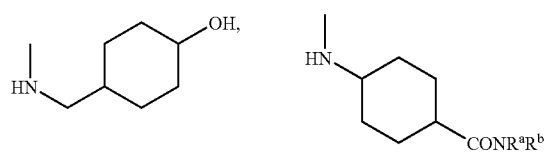
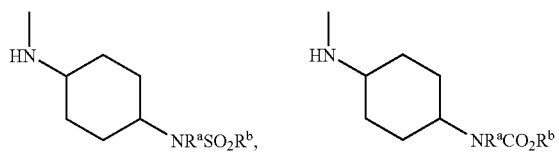
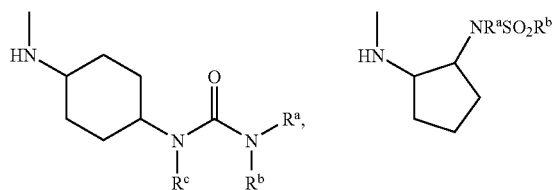
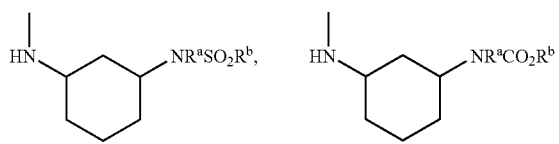
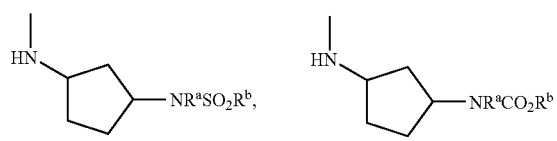
$R^a$, $R^b$, $R^c$ = each independently, hydrogen, $C_1$~$C_3$ alkyl TABLE 74
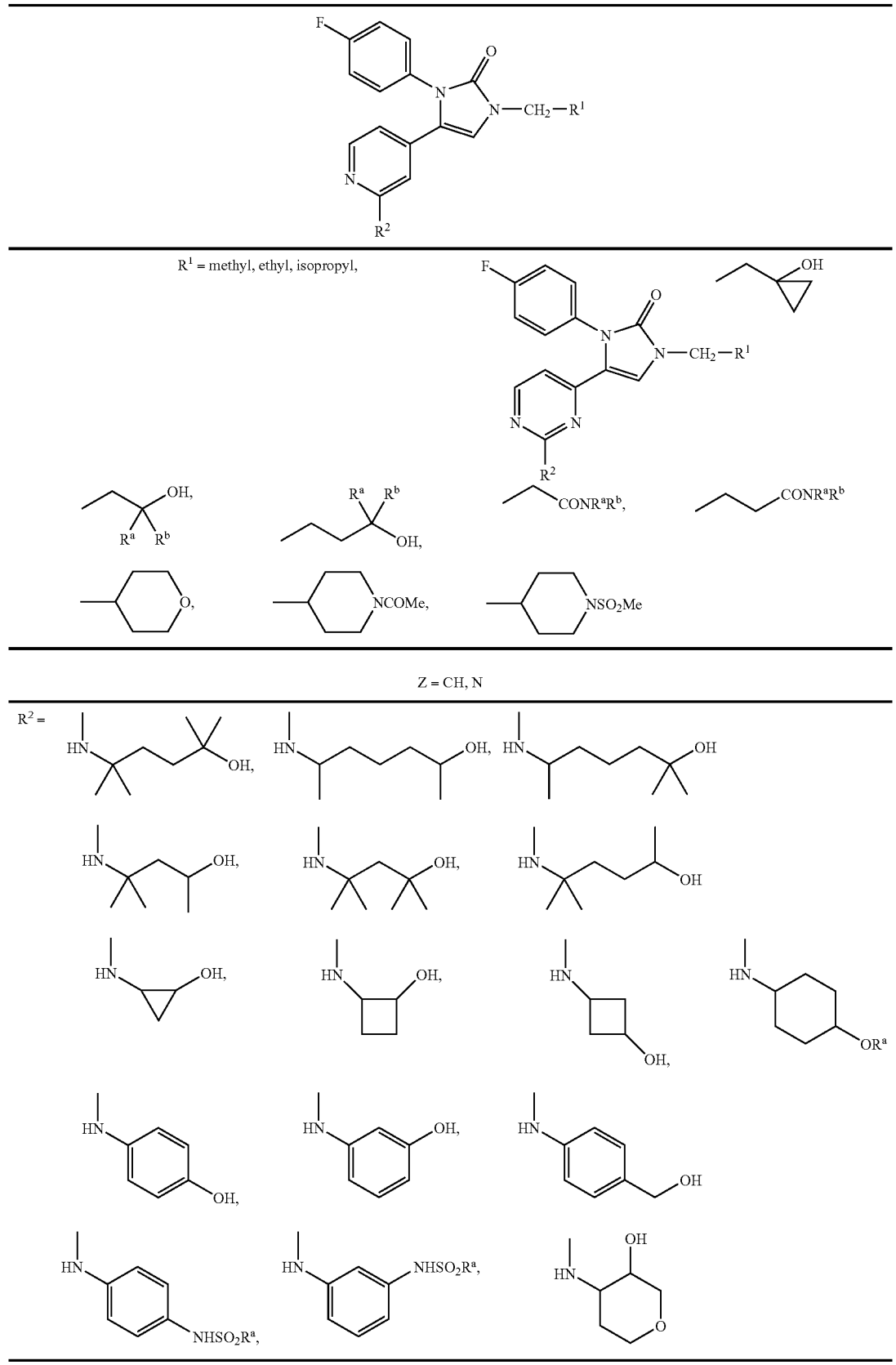
$R^a$, $R^b$ = each independently, hydrogen, $C_1$~$C_3$ alkyl TABLE 75
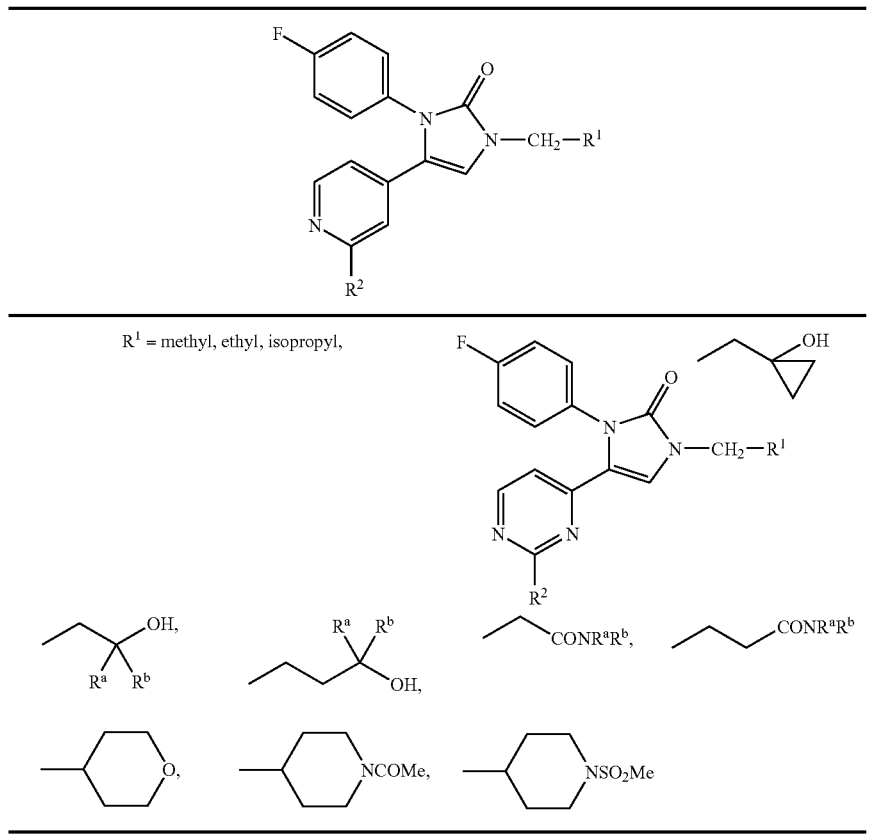
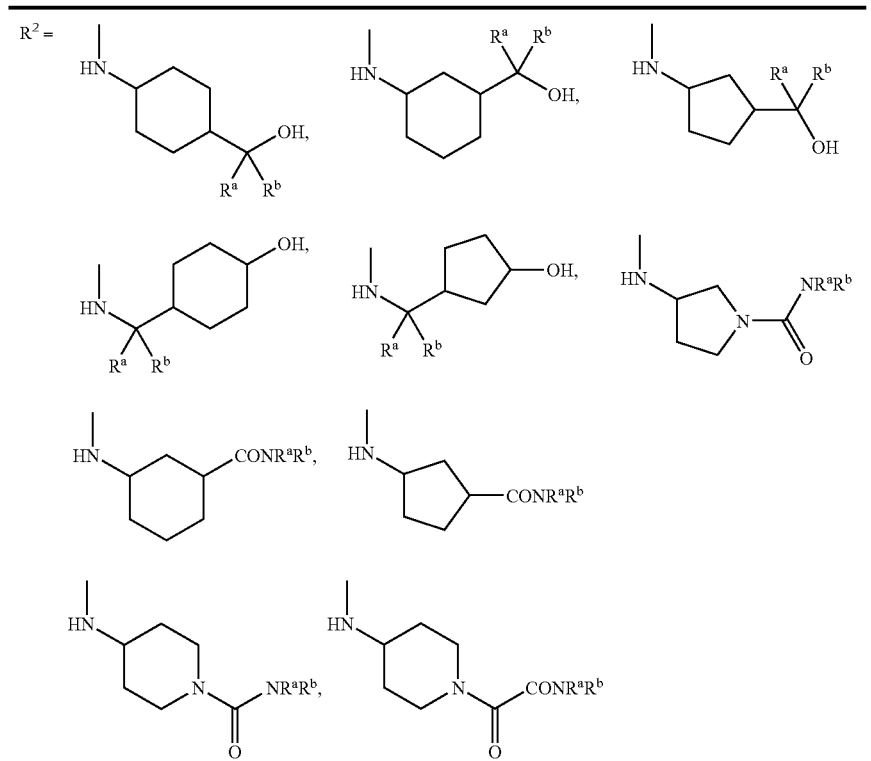
Z = CH, N TABLE 75-continued
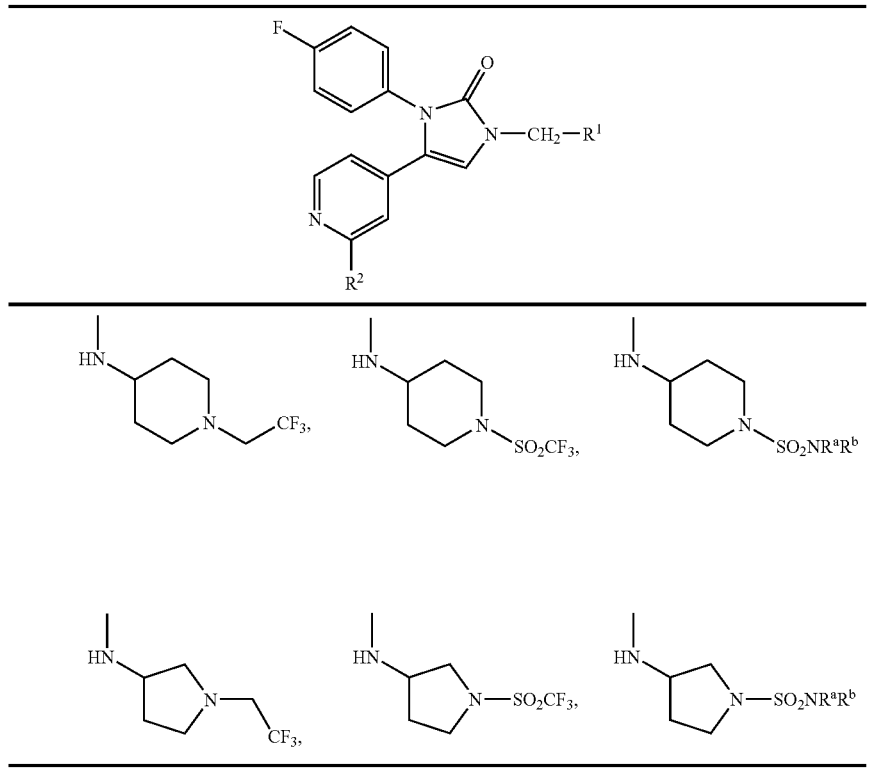
$R^a$, $R^b$ = each independently, hydrogen, $C_1$~$C_3$ alkyl
TABLE 76
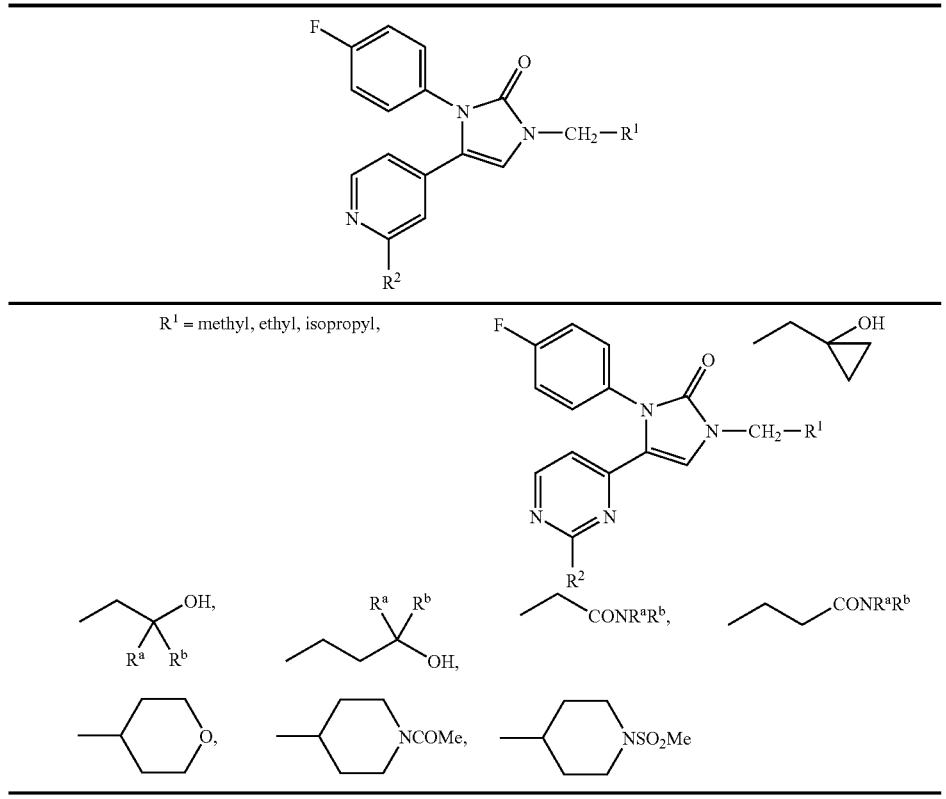

TABLE 76-continued
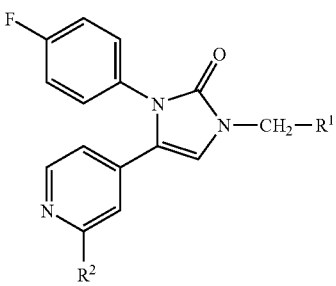
Z = CH, N
R² =
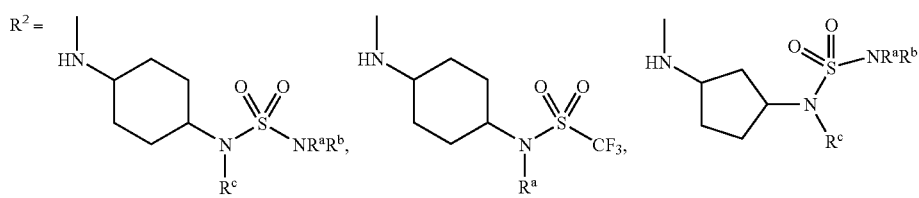
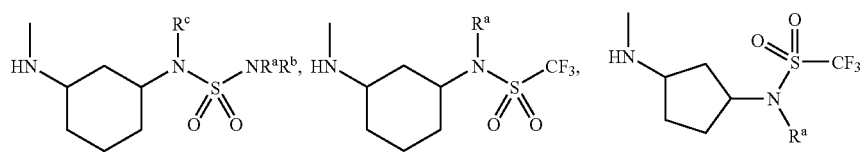
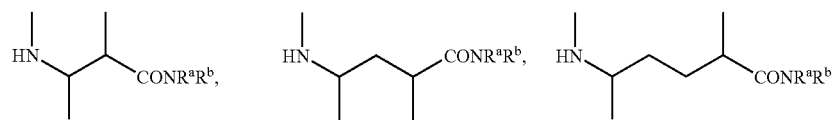
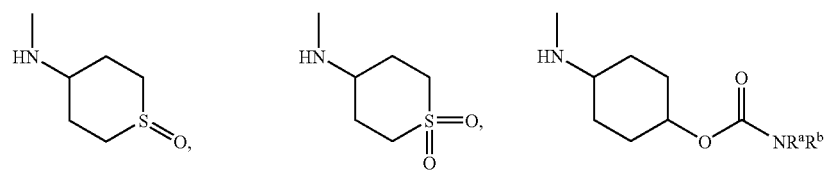
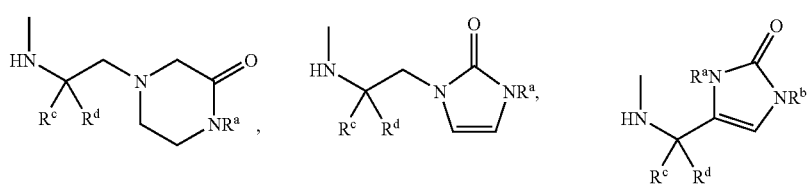
$R^a$, $R^b$, $R^c$, $R^d$ = each independently, hydrogen, $C_1$~$C_3$ alkyl TABLE 77
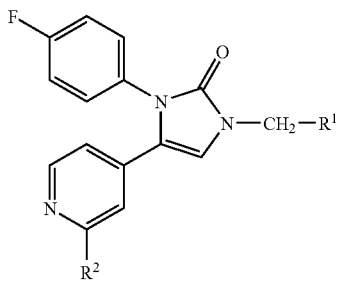
R¹ = methyl, ethyl, isopropyl,
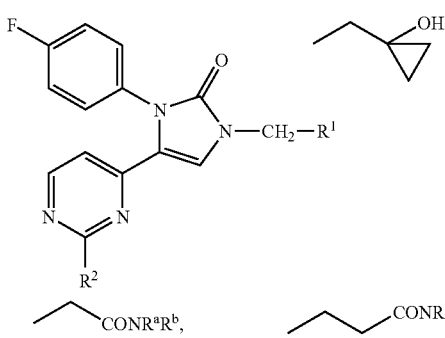
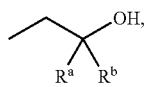, 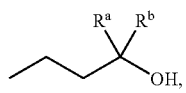, 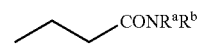
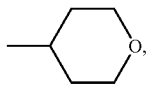, 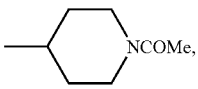, 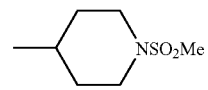
Z = CH, N
R² =
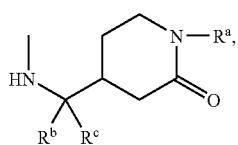 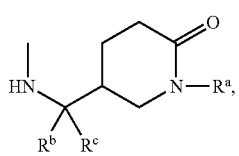 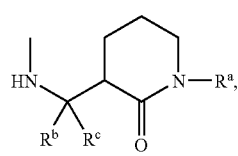 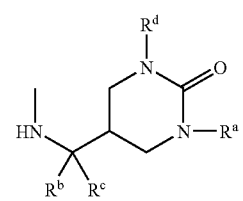
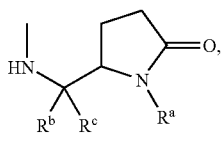 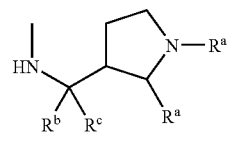 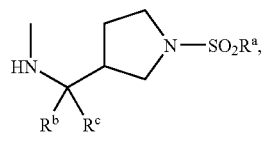 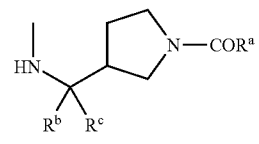
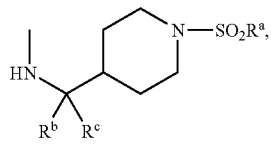 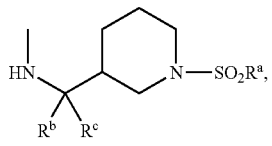 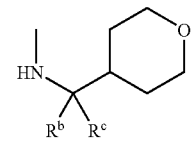
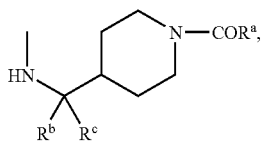 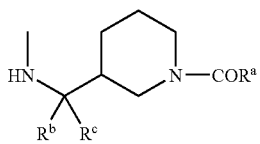

TABLE 77-continued

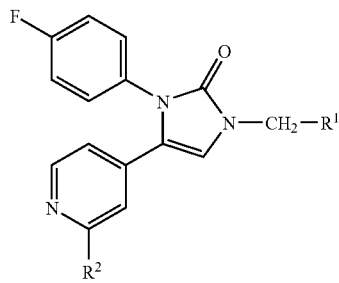

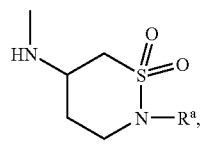 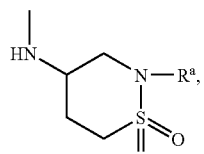 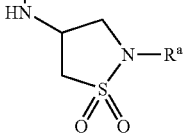

$R^a$, $R^b$, $R^c$, $R^d$ = each independently, hydrogen, $C_1\sim C_3$ alkyl

Reference Example 1

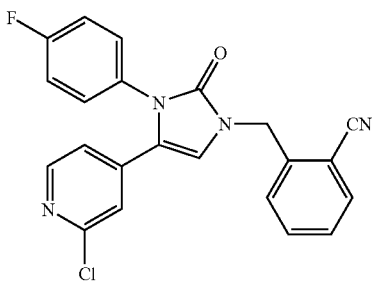

(1) In 440 ml of THF was suspended 22 g of 2-chloroisonicotinic acid, and under nitrogen flow, the mixture was cooled to −70° C. or lower, 245 ml of methyl lithium (1.14 M solution in diethyl ether) was added dropwise to the mixture. After stirring at the same temperature for an hour, a temperature of the mixture was raised to 0° C. over an hour, and stirred at the same temperature for further an hour. To the reaction mixture was added 500 ml of water, and the reaction mixture was extracted with ethyl acetate, washed with brine and dried over magnesium sulfate. Activated charcoal was added to the mixture, and after filtration, the filtrate was concentrated under reduced pressure to give 19.5 g of 4-acetyl-2-chloropyridine as colorless crystals. Melting point: 36° C.

(2) In 550 ml of ethanol were suspended 55.1 g of the compound obtained in (1), 49.2 g of hydroxylamine hydrochloride and 58.1 g of sodium acetate, and the mixture was refluxed under heating for an hour. After cooling the mixture to room temperature by allowing to stand, ethanol was distilled away under reduced pressure and precipitated crystals were collected by filtration and washed with water. The crystals were air-dried at 60° C. overnight to give 55 g of 1-(2-chloropyridin-4-yl)ethanone oxime as colorless crystals. Melting point: 143° C.

(3) In methylene chloride were suspended 105 g of the compound obtained in (2) and 123 g of tosyl chloride, and under ice-cooling, 94 ml of triethylamine was added dropwise to the mixture, and the mixture was raised to room temperature and stirred for 4 hours. To the reaction mixture was added 500 ml of water, and the mixture was extracted with methylene chloride, washed with brine and dried over magnesium sulfate. After filtration, the mixture was concentrated under reduced pressure, and the resulting crystals were collected by filtration and washed with isopropyl ether to give 192 g of 1-(2-chloropyridin-4-yl)ethanone oxime tosylate as colorless crystals. Melting point: 153° C.

(4) Under nitrogen flow, 3.11 g of sodium metal was added to 220 ml of anhydrous ethanol at room temperature, and the mixture was dissolved under stirring. The solution was ice-cooled, and 40 g of the compound obtained in (3) was added thereto, then the mixture was stirred at room temperature for an hour. To the mixture was added 220 ml of anhydrous ether, and insoluble matters were removed. To the filtrate was added 62 ml of 4N hydrochloric acid/dioxane solution under ice-cooling and the mixture was stirred for 15 minutes. After the reaction mixture was concentrated under reduced pressure, the residue was dissolved in water and the solution was made alkaline by addition of potassium carbonate. This mixture was extracted with ethyl acetate several times, and the combined extracts were washed with brine and dried over magnesium sulfate. After concentration under reduced pressure, 100 ml of hexane was added to the residue and red insoluble matters were removed by filtration. The filtrate was concentrated under reduced pressure, hexane was again added to the concentrate and insoluble matters were removed by filtration through Celite. The filtrate was concentrated under reduced pressure and dried by a vacuum pump to give 26.9 g of 2-(2-chloropyridin-4-yl)-2,2-diethoxyethylamine as reddish oily product.

(5) A solution, in which 20 g of the compound obtained in (4) was dissolved in 50 ml of THF, was water-cooled, and 11.2 g of 4-fluorophenylisocyanate was added dropwise thereto. After dropwise addition, the reaction mixture was concentrated under reduced pressure, and 30 ml of conc. hydrochloric acid was added to the obtained residue and the mixture was stirred at room temperature overnight. The reaction mixture was added to ice-cooled 180 ml of 2N aqueous NaOH solution to neutralize the mixture, and after collecting the precipitated crystals by filtration, the crystals were washed with water and ether. The crystals were air-dried at 60° C. to give 22.3 g of 5-(2-chloropyridin-4-yl)-1-(4-fluorophenyl)-1)-4-imidazolin-2-one as colorless crystals. Melting point: 270° C.

(6) In 50 ml of DMF was suspended 10 g of the compound obtained in (5), and under ice-cooling, 1.46 g of 63% sodium hydride was added to the suspension, then the mixture was stirred at room temperature for 30 minutes. The mixture was again ice-cooled, and after adding 7.44 g of 2-cyanobenzyl bromide, the mixture was stirred at room temperature for 3 hours. The reaction mixture was poured into 250 ml of ice-cold water, extracted with ethyl acetate. The extract was washed with water and brine, and dried over anhydrous magnesium sulfate. After concentration under reduced pressure, the residue was purified by silica gel column chromatography to give 11.4 g of 4-(2-chloropyridin-4-yl)-3-(4-fluorophenyl)-1-(2-cyanobenzyl)-4-imidazolin-2-one as colorless crystals. Melting point: 109° C.

Reference Example 2

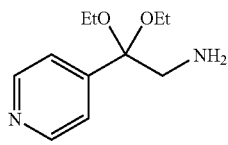

By using 4-acetylpyridine (commercially available product) as a starting material, the same treatments as in Reference examples 1(2) to (4) were carried out to give 2,2-diethoxy-2-pyridin-4-yl ethylamine as brownish oily product.

Reference Example 3

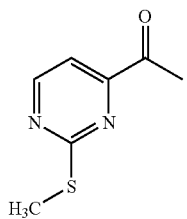

(1) A mixture of 100 g of 3,3-dimethoxy-2-butanone and 99.2 g of N,N-dimethylformamide dimethylacetal was stirred at 100° C. for 42 hours. After cooling the reaction mixture, the mixture was concentrated under reduced pressure to give 141 g of 1-dimethylamino-4,4-dimethoxy-1-penten-3-one.

(2) In 800 ml of methanol was dissolved 141 g of the compound obtained in (1), and after adding 114 g of thiourea and 292 g of 28% sodium methoxide-methanol, the mixture was stirred at 70° C. for 3 hours. The mixture was ice-cooled, and after adding 215 g of methyl iodide drowise, the mixture was stirred at room temperature for an hour. After concentration of the reaction mixture, water was added to the mixture and the resulting mixture was extracted with ethyl acetate. The organic layer was washed, dried and concentrated to give 142 g of 4-(1,1-dimethoxyethyl)-2-methylsulfanylpyrimidine.

(3) In 570 ml of acetone was dissolved 142 g of the compound obtained in (2), and under ice-cooling, 114 ml of 6M hydrochloric acid was added to the solution and the mixture was stirred at room temperature for 3 hours. After adding 450 ml of water to the mixture, the solvent was removed and the residue was extracted with ethyl acetate. The organic layer was washed, dried and concentrated to give 107 g of 1-(2-methyl-sulfanylpyrimidin-4-yl)ethanone.

Reference Example 4

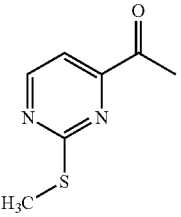

(1) A mixture comprising 16.4 g of 4-chloro-2-methyl-sulfanylpyrimidine, 38 g of tributyl(1-ethoxyvinyl)tin, 1.43 g of bis(triphenylphosphine)palladium (II) dichloride and 100 ml of DMF was stirred at 80° C. for 3 hours. After cooling the reaction mixture, 300 ml of ethyl acetate and 17.8 g of potassium fluoride were added to the mixture, and the resulting mixture was stirred at room temperature overnight. After filtration with Celite, the filtrate was washed, dried and concentrated. The residue was purified by silica gel column chromatography (hexane:ethylacetate=20:1) to give 18.9 g of 4-(1-ethoxy-vinyl)-2-methylsulfanylpyrimidine.

(2) In 200 ml of acetone was dissolved 18.9 g of the compound obtained in (1), 60 ml of 4M hydrochloric acid was added to the solution and the mixture was stirred at room temperature for an hour. The reaction mixture was added to a saturated aqueous sodium bicarbonate solution, and extracted with ethyl acetate. The organic layer was washed, dried and concentrated to give 15.9 g of 1-(2-methylsulfanylpyrimidin-4-yl)ethanone.

Reference Example 5

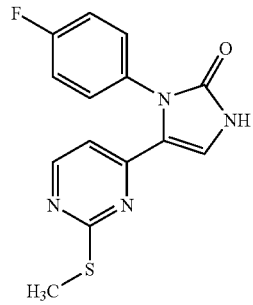

(1) In 180 ml of methanol was dissolved 17.6 g of the compound obtained in Reference example 3(3) or Reference example 4(2), 14.5 g of hydroxylamine hydrochloride and 17.2 g of sodium acetate were added to the solution, and the mixture was refluxed under heating for 30 minutes. After cooling the reaction mixture, the solvent was removed, water was added to the residue and the mixture was extracted with ethyl acetate. The organic layer was washed, dried and concentrated. To the residue was added hexane and the precipitated crystals were collected by filtration to give 18.3 g of 1-(2-methylsulfanylpyrimidin-4-yl)ethanone oxime. Melting point: 150-152° C.

(2) In 1200 ml of methylene chloride was suspended 89 g of the compound obtained in (1), and 81.2 ml of triethylamine and 102 g of tosyl chloride were added to the suspension, and the mixture was stirred at room temperature overnight. The reaction mixture was washed, dried and concentrated. To the residue was added diethyl ether and the precipitated crystals were collected by filtration to give 159 g of 1-(2-methylsulfanylpyrimidin-4-yl)ethanoneoxime tosylate. Melting point: 141-142° C.

(3) To 30 ml of methanol solution containing 12.9 g of 28% sodium methoxide-methanol was added dropwise 120 ml of a THF solution containing 15 g of the compound obtained in (2) under ice-cooling, and the mixture was stirred at room temperature overnight. To the mixture was added 100 ml of 4M hydrochloric acid-dioxane solution under ice-cooling, and after stirring at room temperature for 4 hours, the reaction mixture was concentrated. The residue was added to an aqueous potassium carbonate solution and extracted with chloroform. The organic layer was dried and concentrated, and the residue was purified by silica gel column chromatography (chloroform:methanol=15:1) to give 8.14 g of 2,2-dimethoxy-2-(2-methyl-sulfanylpyrimidin-4-yl)ethylamine.

(4) To 120 ml of a THF solution containing 8 g of the compound obtained in (3) was added dropwise under ice-cooling 30 ml of a THF solution containing 4.78 g of 4-fluorophenyl isocyanate, and the mixture was stirred at room temperature for 30 minutes. After 120 ml of conc. hydrochloric acid was added to the mixture under ice-cooling, the resulting mixture was stirred at room temperature overnight. Precipitated crystals were collected by filtration, washed with water and ether, and dried to give 7.35 g of 1-(4-fluorophenyl)-5-(2-methylsulfanylpyrimidin-4-yl)-4-imidazolin-2-one. Melting point: 260-261° C.

Reference Example 6

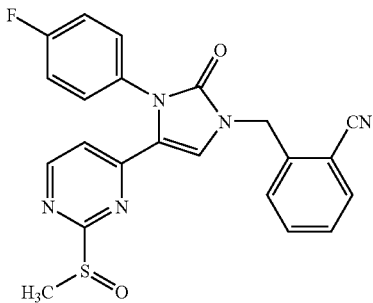

(1) To 40 ml of a DMF solution containing 2.6 g of the compound obtained in Reference example 5(4) was added 327 mg of sodium hydride at room temperature, and the mixture was stirred at room temperature for 30 minutes. To the mixture was added 1.77 g of 2-cyanobenzyl bromide, and after stirring at room temperature for 30 minutes, 33 mg of sodium hydride and 85 mg of 2-cyanobenzyl bromide were added to the mixture, and the resulting mixture was stirred at room temperature for an hour. Water was added to the reaction mixture and the mixture was extracted with ethyl acetate. The organic layer was washed, dried and concentrated, and crystallized from diethyl ether to give 3.28 g of 1-(2-cyanobenzyl)-3-(4-fluorophenyl)-4-(2-methylsulfanylpyrimidin-4-yl)-4-imidazolin-2-one. Melting point: 141-142° C.

(2) To a chloroform solution containing 3.27 g of the compound obtained in (1) was added 2.03 g of 3-chloroperoxybenzoic acid at room temperature, and the mixture was stirred at room temperature for an hour. To the reaction mixture was added 1.16 g of calcium hydroxide and the mixture was stirred at room temperature for 2 hours, and then, filtered through Celite, and the filtrate was concentrated. The residue was crystallized from ethyl acetate to give 2.39 g of 1-(2-cyanobenzyl)-3-(4-fluorophenyl)-4-(2-methylsulfinylpyrimidin-4-yl)-4-imidazolin-2-one. Melting point: 133-136° C.

Reference Example 7

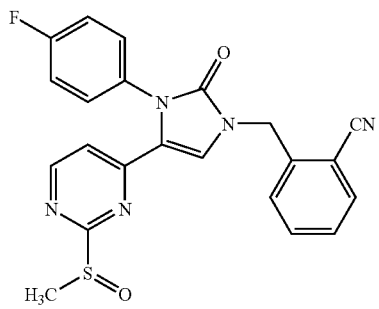

(1) To 150 ml of a methanol solution containing 1.47 g of the compound obtained in Reference Example 5(4) was added dropwise 10 ml of an aqueous solution containing 1.79 g of Oxone® at room temperature. After 30 minutes and 2 hours, 2 ml of an aqueous solution containing 299 mg of Oxone® was added dropwise, and the mixture was stirred at room temperature for 2 hours. After removing insoluble matters by filtration, the filtrate was concentrated, an aqueous sodium bicarbonate solution was added to the concentrate and the mixture was extracted with chloroform. The organic layer was washed, dried and concentrated, and the precipitated crystals were collected by a mixed solvent of ethyl acetate-ether (1:1) to give 1.03 g of 1-(4-fluorophenyl)-5-(2-methylsulfinylpyrimiidin-4-yl)-4-imidazolin-2-one. Melting point: 208-211° C. (decomposed).

(2) The compound (930 mg) obtained in (1) was treated in the same manner as in the above-mentioned Reference Example 6(1) to give 541 mg of 1-(2-cyanobenzyl)-3-(4-fluorophenyl)-4-(2-methylsulfinylpyrimidin-4-yl)-4-imidazolin-2-one.

Reference Example 8

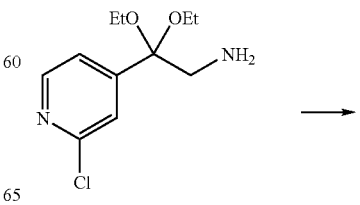

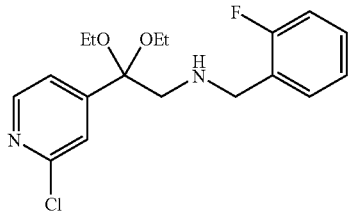

In 10 ml of methanol was dissolved 1.0 g of the compound obtained in Reference Example 1(4), 0.51 g of 2-fluorobenzaldehyde was added to the solution, and the mixture was stirred at room temperature for 30 minutes. To the mixture was added 155 mg of sodium borohydride, and the resulting mixture was further stirred at room temperature for an hour. After concentration under reduced pressure, water was added to the reside and the mixture was extracted with ethyl acetate. The extract was washed with brine and dried over anhydrous magnesium sulfate. After concentration under reduced pressure, the residue was purified by silica gel column chromatography (hexane:ethylacetate=2:1) to give 1.45 g the title compound as an oily product.

Reference Example 9

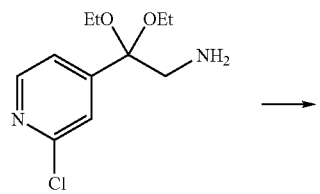

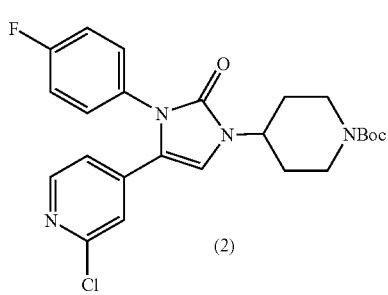

The compound (5 g) obtained in Reference Example 1(4) and a corresponding starting material were treated in the same manner as in Reference Example 8 to give 8.47 g of Compound (1). Compound (1) (3 g) was treated in the same manner as in Example 1 to carry out cyclization, subsequently the resulting compound was dissolved in 20 ml of THF, 1.1 g of Boc$_2$O was added thereto. The resulting mixture was stirred at room temperature for 30 minutes, concentrated under reduced pressure and diisopropyl ether was added to the residue, and the residue was collected by filtration to give 2.53 g of Compound (2).

Reference Example 10

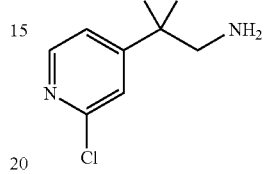

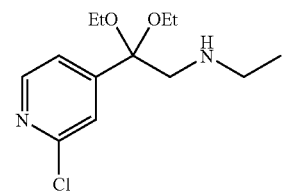

A mixture comprising 3.8 g of the compound obtained in Reference example 1 (4), 1.7 ml of ethyl iodide and 3.0 ml of triethylamine was stirred at 50° C. overnight. After neutralizing with 2N aqueous NaOH solution, the reaction mixture was extracted with chloroform and dried over anhydrous magnesium sulfate. The resulting mixture was purified by NH silica gel column chromatography (hexane:ethyl acetate=4:1) to give 1.9 g of the title compound as an oily product.

Reference Example 11

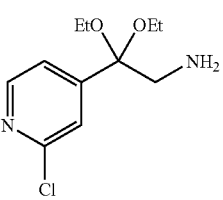
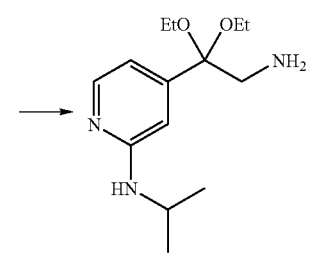

In 75 ml of toluene were suspended 5.0 g of the compound obtained in Reference Example 1(4), 35 ml of isopropylamine, 458 mg of palladium acetate, 1.28 g of 2,2'-bis(diphenylphosphino)-1,1'-binaphthyl and 3.0 g of sodium t-butoxide, and under nitrogen flow, the mixture was stirred under heating at 70° C. for 8 hours. After concentration under reduced pressure, water was added to the residue, and the mixture was extracted with chloroform, washed with brine and dried over anhydrous magnesium sulfate. After concentration under reduced pressure, the residue was purified by silica gel column chromatography (chloroform:methanol=10:1) to give 4.3 g of the title compound as an oily product.

Reference Example 12

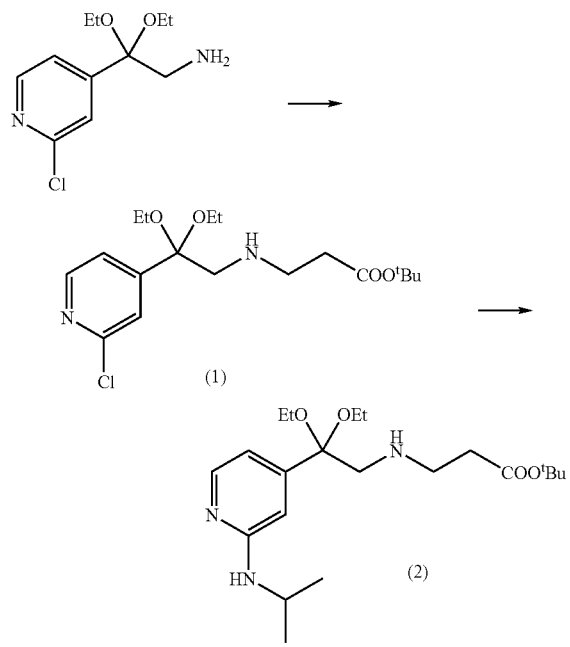

A mixture comprising 2.0 g of the compound obtained in Reference example 1(4), 0.82 ml of t-butyl acrylate and 10 ml of THF was stirred under reflux for 4 days. The reaction mixture was concentrated under reduced pressure to give 3.1 g of Compound (1) as an oily product. Then, Compound (1) and a corresponding starting material were treated in the same manner as in Example 4 to give 2.12 g of Compound (2) as an oily product.

Reference Example 13

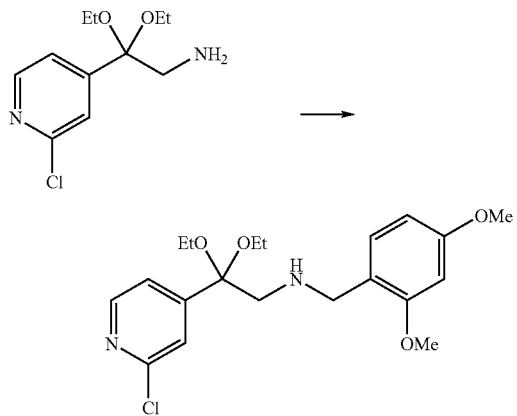

The compound (5.0 g) obtained in Reference Example 1(4) was reacted with 2,4-dimethoxybenzaldehyde in the same manner as in Reference Example 8 to give 6.4 g of the title compound.

Reference Example 14

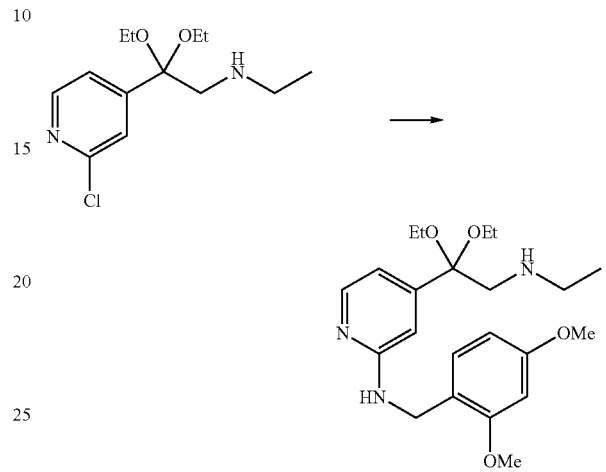

The compound (1.39 g) of Reference Example 10 was reacted with 2,4-dimethoxybenzylamine in the same manner as in Reference example 11 to give 1.58 g of the title compound.

Reference Example 15

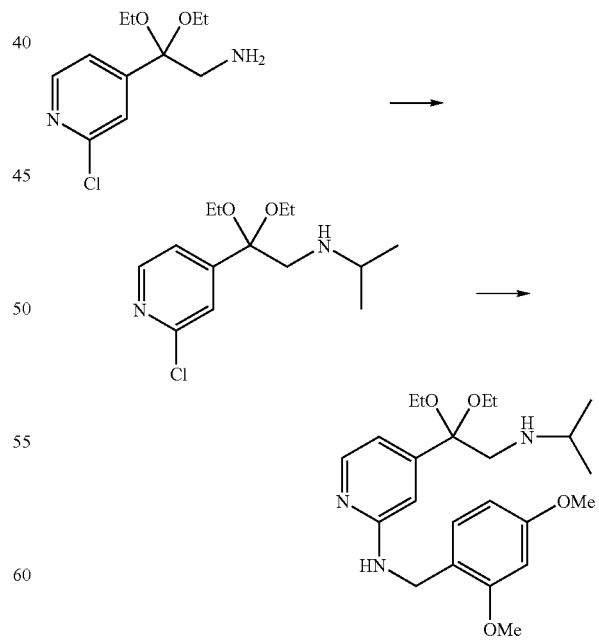

The compound (10.0 g) of Reference Example 1(4) was reacted with a corresponding starting material in the same manner as in Reference Example 8, and then, reacted with 2,4-dimethoxy-benzylamine in the same manner as in Reference Example 11 to give 9.75 g of the title compound.

Reference Example 16

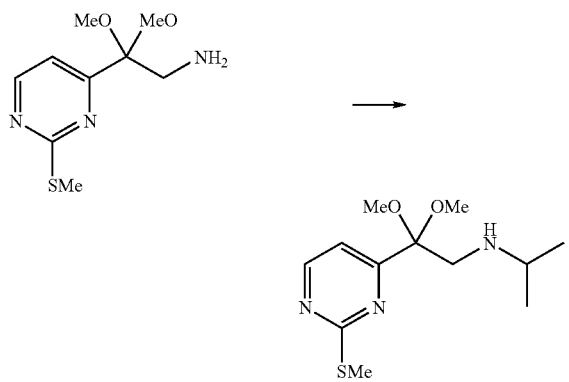

The compound (26.8 g) of Reference Example 5(3) and a corresponding starting material were treated in the same manner as in Reference Example 8 to give 30.8 g of the title compound.

Reference Example 17

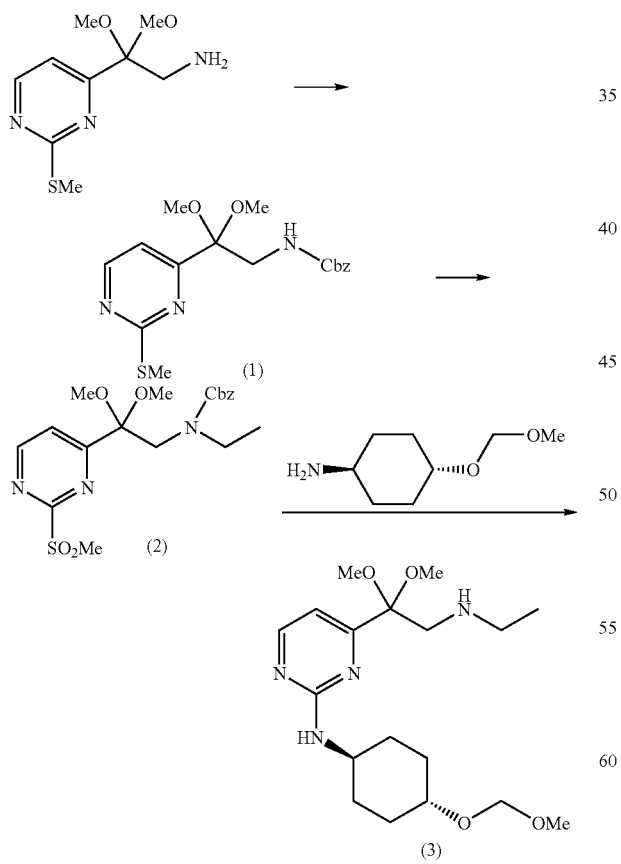

(1) In 30 ml of methylene chloride was dissolved 3.0 g of the compound of Reference Example 5(3), 3.65 ml of triethylamine was added to the solution, and under ice-cooling, 3.35 g of benzyloxycarbonyl chloride was added dropwise to the mixture, and the mixture was stirred at room temperature overnight. The reaction mixture was washed with water and brine, and dried over anhydrous magnesium sulfate. After concentration under reduced pressure, the residue was purified by silica gel column chromatography to give 2.23 g of Compound (1) as colorless crystals.

MS 364 ([M+H]$^+$).

(2) In 17 ml of DMF was dissolved 4.2 g of Compound (1), and under ice-cooling, 528 mg of sodium hydride was added to the solution, and the mixture was stirred at room temperature for an hour. The mixture was again ice-cooled, 1.39 ml of ethyl iodide was added thereto, and the resulting mixture was stirred at room temperature for 30 minutes. Water was added to the reaction mixture and the mixture was extracted with ethyl acetate, the extract was washed with water and brine, and dried over anhydrous magnesium sulfate. After concentration under reduced pressure, the residue was dissolved in 50 ml of chloroform, 6.26 g of 3-chloroperoxybenzoic acid was added to the mixture at room temperature, and the resulting mixture was stirred at the same temperature for 30 minutes. To the reaction mixture was added 2.58 g of calcium hydroxide and after stirring the mixture, the insoluble matters were removed by filtration. The filtrate was concentrated under reduced pressure, and purified,by silica gel column chromatography to give 4.55 g of Compound (2) as a colorless oily product.

MS 423 ([M+H]$^+$).

(3) In 30 ml of dioxane was dissolved 2.19 g of Compound (2), 1.65 g of trans-4- (Methoxymethoxy) cyclohexylamine and 1.08 ml of 1,1'-diisopropylethylamine were added to the solution, and the mixture was stirred at 100° C. for 14 hours. Water was added to the reaction mixture and the mixture was extracted with ethyl acetate, washed with brine and dried over anhydrous magnesium sulfate. After concentration under reduced pressure, the residue was purified by silica gel column chromatography to give 2.0 g of a brownish oily product. This product was dissolved in 40 ml of methanol, 1 g of 10% palladium-carbon was added thereto, and the mixture was subjected to catalytic reduction under hydrogen pressure (2.7 atm) for 2 hours. Palladium was removed by filtration, and after concentration under reduced pressure, the residue was purified by NH silica gel column chromatography to give 1.04 g of Compound (3) as a brownish oily product.

MS 369 ([M+H]$^+$).

Experimental Example 1

Pharmacological Test

Inhibition of Lipopolysaccharide (LPS)-stimulated TNF-α Production in Mice in vivo Tests were carried out to measure an inhibitory effects of the compounds of the present invention on LPS-stimulated TNF-α production in mice.

To Balb/cAnNCrj mice (6-8 weeks old, female, available from Japan Charlesriver, Co.) were administered test compounds (10 mg/kg, p.o.) dissolved in 0.5% methyl cellulose and 0.2% PEG-60 hydrogenated caster oil (HCO60, available from Nikko Chemicals, Co.). After 30 minutes, LPS (*E. coli* 0111:B4, available from Difco, with a final concentration of 1 mg/kg adjusted by phosphate buffered saline) was administered (0.4 ml/head, i.p.). 90 minutes later, blood was collected from abdominal vein of the mouse under diethyl ether anesthesia. The collected blood was subjected to centrifugation with 3000 g to collect serum. TNF-α in the sera was measured by DuoSet mouse TNF-α ELISA kit (trade name, available from genzymeTECHNE).

As a result, the compounds of the present invention significantly reduced the production of TNF-α as shown in Table 78.

TABLE 78

| Examples | TNF-α inhibition rate |
|---|---|
| 182 | 64% |
| 202 | 57% |
| 239 | 69% |
| 296 | 52% |
| 300 | 57% |

INDUSTRIAL APPLICABILITY

According to the present invention, a novel 4-imidazolin-2-one compound having excellent p38MAP kinase inhibitory activity, which is useful as a medicine, can be provided.

The invention claimed is:

1. A compound of the formula [I]:

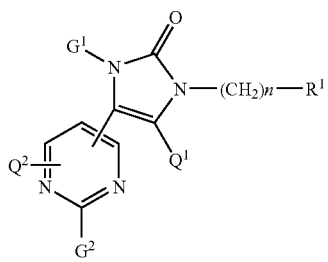

wherein $G^1$ is a group of the formula:

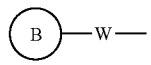

wherein ring B is benzene ring, naphthalene ring, or a cycloalkane, and the benzene ring, the naphthalene ring, and the cycloalkane may be substituted by 1 to 3 substituent(s), which is(are) the same or different, and selected from the group consisting of a halogen atom, nitro, an optionally substituted alkyl, an optionally substituted alkoxy, an optionally substituted amino, an optionally substituted carbamoyl, hydroxy and cyano, W is a single bond, or a $C_1$-$C_4$ alkylene which may be substituted by 1 or 2 alkyl(s), $Q^1$ and $Q^2$ may be the same or different, and each is hydrogen atom, a halogen atom or an alkyl, n is 0, 1, 2, 3 or 4, $R^1$ is hydrogen atom, an optionally substituted alkyl, an optionally substituted cycloalkyl, an optionally substituted phenyl or an optionally substituted heterocyclic group, $G^2$ is hydrogen atom, —$NR^3R^4$, —$OR^5$, —$SR^5$ —$COR^6$ or —$CHR^7R^8$, where $R^3$ $R^8$ each independently is hydrogen atom, an optionally substituted alkyl, an alkenyl, an alkynyl, hydroxy, an alkoxy, an optionally substituted amino, an optionally substituted alkanoyl, an optionally substituted carbamoyl, an alkoxyoxalyl, an alkylsulfonyl, an optionally substituted cycloalkyl, an optionally substituted phenyl, an optionally substituted heterocyclic group, a carbonyl substituted by an optionally substituted cycloalkyl, a carbonyl substituted by an optionally substituted phenyl or a carbonyl substituted by an optionally substituted heterocyclic group, or a pharmaceutically acceptable salt thereof.

2. A compound of the formula [Ia]:

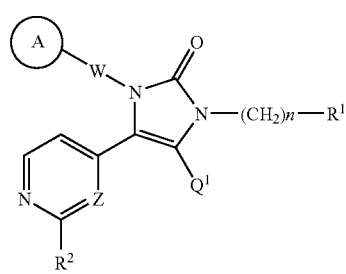

wherein ring A is benzene ring, and the benzene ring may be substituted by 1 to 3 substituent(s), which is (are) the same or different, and selected from the group consisting of a halogen atom, nitro, an optionally substituted alkyl, an optionally substituted alkoxy, an optionally substituted amino, an optionally substituted carbamoyl, hydroxy and cyano, $Q^1$ is hydrogen atom, a halogen atom or an alkyl, W is a single bond, or a $C_1$-$C_4$ alkylene which may be substituted by 1 or 2 alkyl(s), n is 0, 1, 2, 3 or 4, $R^1$ is hydrogen atom, an optionally substituted alkyl, an optionally substituted cycloalkyl, an optionally substituted phenyl or an optionally substituted heterocyclic group, $R^2$ is hydrogen atom, —$NR^3R^4$, —$OR^5$, $COR^6$ or —$CHR^7R^8$, where $R^3$ $R^8$, each independently is hydrogen atom, an optionally substituted alkyl, an alkenyl, an alkynyl, hydroxy, an alkoxy, an optionally substituted amino, an optionally substituted alkanoyl, an optionally substituted carbamoyl, an alkoxyoxalyl, an alkylsulfonyl, an optionally substituted cycloalkyl, an optionally substituted phenyl, an optionally substituted heterocyclic group, a carbonyl substituted by an optionally substituted cycloalkyl, a carbonyl substituted by an optionally substituted phenyl or a carbonyl substituted by an optionally substituted heterocyclic group, or a pharmaceutically acceptable salt thereof.

3. The compound according to claim 2, wherein $Q^1$ is hydrogen atom, or a pharmaceutically acceptable salt thereof.

4. The compound according to claim 2, wherein the ring A is a benzene ring which may be substituted by 1 to 3 substituent(s), which is(are) the same or different, and selected from the group consisting of a halogen atom, nitro, an optionally substituted alkyl, an optionally substituted alkoxy, an optionally substituted amino and cyano, and W is a single bond, or a pharmaceutically acceptable salt thereof.

5. The compound according to claim 2, wherein n is 0 or 1, or a pharmaceutically acceptable salt thereof.

6. The compound according to claim 2, wherein (1) n is 0 and $R^1$ is an optionally substituted alkyl, (2) n is 1 and $R^1$ is an optionally substituted cycloalkyl, (3) n is 1 and $R^1$ is an optionally substituted phenyl, (4) n is 1 and $R^1$ is an optionally substituted heterocyclic group, (5) n is 0 and $R^1$ is an optionally substituted cycloalkyl, and (6) n is 0 and $R^1$ is an optionally substituted heterocyclic group, or a pharmaceutically acceptable salt thereof.

7. The compound according to claim 2, wherein $R^2$ is —$NR^3R^4$ or —$OR^5$, or a pharmaceutically acceptable salt thereof.

8. The compound according to claim 2, wherein $R^2$ is —$NHR^4$, and $R^4$ is an optionally substituted alkyl, an alkenyl, an optionally substituted alkanoyl, an optionally substituted carbamoyl, an optionally substituted cycloalkyl, an optionally substituted phenyl, an optionally substituted heterocyclic group, a carbonyl substituted by an optionally substituted cycloalkyl or a carbonyl substituted by an optionally substituted heterocyclic group, or a pharmaceutically acceptable salt thereof.

9. The compound according to claim 3, wherein the ring A is a benzene ring which may be substituted by 1 or 2 substituent(s), which is(are) the same or different, and selected from the group consisting of a halogen atom, an optionally substituted alkyl, an optionally substituted alkoxy, an optionally substituted amino and cyano, W is a single bond, n is 0 or 1, $R^1$ is hydrogen atom, an optionally substituted alkyl, an optionally substituted cycloalkyl, an optionally substituted phenyl or an optionally substituted heterocyclic group, Z is CH or N, $R^2$ is hydrogen atom, —$NR^3R^4$, —$OR^5$, $COR^6$ or —$CHR^7R^8$, Where $R^3$ to $R^8$ each independently is hydrogen atom, an optionally substituted alkyl, an alkenyl, an alkoxy, an optionally substituted alkanoyl, an optionally substituted carbamoyl, an alkoxyoxalyl, an optionally substituted cycloalkyl, an optionally substituted phenyl, an optionally substituted heterocyclic group, a carbonyl substituted by an optionally substituted cycloalkyl or a carbonyl substituted by an optionally substituted heterocyclic group, or a pharmaceutically acceptable salt thereof.

10. The compound according to claim 3, wherein the ring A is a beuzene ring which may be substituted by 1 or 2 substituent(s), which is(are) the same or different, and selected from the group consisting of a halogen atom, an alkyl optionally substituted by halogen(s), an alkoxy, an amino optionally substituted by alkyl(s) and cyano, W is a single bond, n is 0 or 1, $R^1$ is (1) hydrogen atom, (2) an alkyl optionally substituted by group(s) selected from the group consisting of phenyl, an alkoxy, an alkylamino, a dialkylamino, an alkanoylamino, an alkylsulfonylamino, a carbamoyl optionally substituted by alkyl(s), hydroxy, carboxy and cyano, (3) a cycloalkyl optionally substituted by group(s) selected from the group consisting of the following (i) to (v):

(i) hydroxy, (ii) an alkoxy optionally substituted by alkoxy(s), (iii) an amino optionally substituted by group(s) selected from the group consisting of an alkyl, an alkanoyl and an alkylsulfonyl, (iv) a carbainoyl optionally substituted by alkyl(s), and (v) an alkyl optionally substituted by group(s) selected from the group consisting of hydroxy, an alkoxy and amino, (4) a phenyl optionally substituted by group(s) selected from the group consisting of the following (i) to (vi):

(i) a halogen atom, (ii) an alkyl optionally substituted by group(s) selected from the group consisting of a halogen atom, hydroxy and phenylsulfonyl, (iii) cyano, (iv) an alkoxy, (v) an amino optionally substituted by group(s) selected from the group consisting of an alkyl and an alkylsulfonyl, (vi) a carbonyl substituted by a heterocyclic group, or (5) a heterocyclic group optionally substituted by group(s) selected from the group consisting of the following (i) to (iv):

(i) an alkoxycarbonyl, (ii) an alkyl optionally substituted by group(s) selected from the group consisting of hydroxy, an alkoxy and a carbamoyl optionally substituted by alkyl(s), (iii) an alkanoyl and (iv) an alkylsulfonyl, Z is CH or N, $R^2$ is hydrogen atom, —$NR^3R^4$, —$OR^5$, $COR^6$ or —$CHR^7R^8$, where $R^3$ to $R^8$ each independently is:

(1) hydrogen atom, (2) an alkyl optionally substituted by group(s) selected from the group consisting of the following (i) to (vii):

(i) hydroxy, (ii) an alkoxy, (iii) an amino optionally substituted by group(s) selected from the group consisting of an alkyl, an alkanoyl and an alkylsulfonyl, (iv) an alkoxycarbonyl, (v) a cycloalkyl optionally substituted by group(s) selected from the group consisting of the following a) to g):

a) hydroxy, b) an amino optionally substituted by alkyl(s), c) an alkanoylamino, d) an alkylsulfonylamino, e) an alkyl optionally substituted by group(s) selected from the group consisting of hydroxy, an alkoxy, amino, a carbamoyl optionally substituted by alkyl(s), f) carboxy and g) a carbamoyl optionally substituted by alkyl(s), (vi) a phenyl optionally substituted by group(s) selected from the group consisting of a halogen atom, an alkoxy and morpholinylcarbonyl, and (vii) a heterocyclic group optionally substituted by alkyl(s), (3) an alkenyl, (4) an alkoxy, (5) an alkanoyl optionally substituted by group(s) selected from the group consisting of the following (i) to (iv):

(i) hydroxy, (ii) an alkoxy, (iii) an amino optionally substituted by group(s) selected from the group consisting of an alkyl and an alkanoyl, (iv) an alkoxycarbonyl, (6) a carbamoyl optionally substituted by alkyl(s), (7) an alkoxyoxalyl,
(8) a cycloalkyl optionally substituted by group(s) selected from the group consisting of the following (i) to (vii):
   (i) a halogen atom,
   (ii) hydroxy,
   (iii) an alkoxy,
   (iv) an amino optionally substituted by group(s) selected from the group consisting of an alkyl, an alkanoyl, an alkoxycarbonyl and an alkylsulfonyl,
   (v) an alkyl optionally substituted by group(s) selected from the group consisting of hydroxy, an alkoxy, amino, a carbamoyl optionally substituted by alkyl(s),
   (vi) an alkanoyloxy and
   (vii) a carbamoyl optionally substituted by alkyl(s),
(9) a phenyl optionally substituted by group(s) selected from the group consisting of a halogen atom and an alkoxy,
(10) a heterocyclic group optionally substituted by group(s) selected from the group consisting of the following (i) to (vii):
   (i) an alkyl optionally substituted by group(s) selected from the group consisting of phenyl, hydroxy, an alkoxy, amino and a carbamoyl optionally substituted by alkyl(s),
   (ii) an alkoxycarbonyl,
   (iii) an alkanoyl,
   (iv) an alkylsulfonyl,
   (v) oxo,
   (vi) a carbamoyl optionally substituted by alkyl(s),
   (vii) an amino sulfonyl optionally substituted by alkyl(s),
(11) a carbonyl substituted by a cycloalkyl optionally substituted by group(s) selected from the group consisting of hydroxy, amino and an alkanoylamino, or
(12) a heterocyclic group-substituted carbonyl,
or a pharmaceutically acceptable salt thereof.

11. The compound according to claim 3, wherein the ring A is a benzene ring which may be substituted by 1 or 2 substituent(s), which is(are) the same or different, and selected from the group consisting of fluorine atom, chlorine atom, an alkyl optionally substituted by halogen(s) and an alkoxy,
W is a single bond,
n is 0 or 1,
$R^1$ is
(1) hydrogen atom,
(2) an alkyl optionally substituted by group(s) selected from the group consisting of phenyl, an alkoxy, an alkylamino, a dialkylamino, an alkanoylamino, an alkylsulfonylamino, a carbamoyl optionally substituted by alkyl(s), hydroxy, carboxy, cyano, and cycloalkyl,
(3) a cycloalkyl optionally substituted by group(s) selected from the group consisting of the following (i) to (v):
   (i) hydroxy,
   (ii) an alkoxy optionally substituted by alkoxy(s),
   (iii) an amino optionally substituted by group(s) selected from the group consisting of an alkyl, an alkanoyl and an alkylsulfonyl,
   (iv) a carbamoyl optionally substituted by alkyl(s),
   (v) an alkyl optionally substituted by group(s) selected from the group consisting of hydroxy and amino,
(4) a phenyl optionally substituted by group(s) selected from the group consisting of the following (i) to (iv):
   (i) a halogen atom,
   (ii) an alkyl optionally substituted by halogen atom(s),
   (iii) cyano, and
   (iv) an alkoxy, or
(5) a heterocyclic group optionally substituted by alkylsulfonyl or alkanoyl,
Z is CR or N,
$R^2$ is hydrogen atom, $-NR^3R^4$, $-OR^5$, or $COR^6$,
where R3 to R6 each independently is:
(1) hydrogen atom,
(2) an alkyl optionally substituted by group(s) selected from the group consisting of the following (i) to (vii):
   (i) hydroxy,
   (ii) an alkoxy,
   (iii) an alkoxycarbonyl.,
   (iv) a cycloalkyl optionally substituted by group(s) selected from the group consisting of the following a) to e):
      a) hydroxy,
      b) an amino optionally substituted by alkyl(s),
      c) an alkanoylamino,
      d) an alkyl optionally substituted by group(s) selected from the group consisting of hydroxy, amino and a carbamoyl optionally substituted by alkyl(s), and
      e) a carbamoyl optionally substituted by alkyl(s),
   (v) a phenyl optionally substituted by alkoxy(s),
   (vi) a heterocyclic group, and
   (vii) an amino optionally substituted by the group(s) selected from alkanoyl(s) and alkylsulfonyl(s),
(3) an alkenyl,
(4) an alkoxy,
(5) an alkanoyl optionally substituted by group(s) selected from the group consisting of an ailcoxy, an amino optionally substituted by alkanoyl(s), and an alkoxycarbonyl,
(6) a cycloalkyl optionally substituted by group(s) selected from the group consisting of the following (i) to (v):
   (i) hydroxy,
   (ii) an alkoxy,
   (iii) an amino optionally substituted by group(s) selected from the group consisting of an alkyl, an alkanoyl, an alkoxycarbonyl and an alkylsulfonyl,
   (iv) an alkyl optionally substituted by group(s) selected from the group consisting of hydroxy, amino and a carbamoyl optionally substituted by alkyl(s),
   (v) a carbamoyl optionally substituted by alkyl(s),
(7) a heterocyclic group optionally substituted by group(s) selected from the group consisting of the following (i) to (vi):
   (i) an alkyl optionally substituted by phenyl(s),
   (ii) an alkoxycarbonyl,
   (iii) an alkylsulfonyl
   (iv) an alkanoyl,
   (v) a carbamoyl optionally substituted by alkyl(s), and
   (vi) an aminosulfonyl optionally substituted by alkyl(s),
(8) a carbonyl substituted by a cycloalkyl optionally substituted by group(s) selected from the group consisting of hydroxy and amino, or
(9) a heterocyclic group-sub stituted carbonyl,
or a pharmaceutically acceptable salt thereof.

12. A compound of the formula [Ib]:

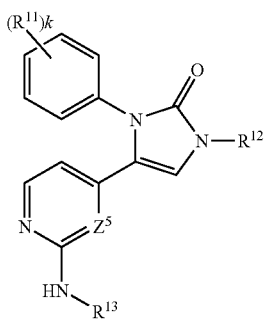

wherein $R^{11}$ is a group selected from the group consisting of hydrogen atom, a halogen atom, a
  $C_1$-$C_4$ alkyl optionally substituted by halogen(s) and a $C_1$-$C_4$ alkoxy,
k is 1 or 2, and when k is 2, two of $R^{11}$ s may be the same or different,
$R^{12}$ is
  (1) a $C_1$-$C_5$ alkyl optionally substituted by group(s) selected from the group consisting of hydroxy, an alkoxy, cyano, amino, tetrahydropyranyl, tetrahydrofuryl and a carbamoyl optionally substituted by alkyl(s),
  (2) a $C_3$-$C_4$ cycloalkylmethyl,
  (3) a $C_3$-$C_4$ cycloalkyl,
  (4) carbamoylmethyl,
  (5) a benzyl optionally substituted by group(s) selected from the group consisting of cyano, a halogen atom, a $C_1$-$C_3$ alkoxy, a $C_1$-$C_3$ alkyl and a halogen-substituted $C_1$-$C_3$ alkyl,
  (6) tetrahydropyranyl,
  (7) tetrahydrofuryl, and
  (8) a piperidyl optionally substituted by group(s) selected from the group consisting of an alkyl, an alkanoyl, an alkylsulfonyl, an alkoxycarbonyl and a carbamoylalkyl optionally substituted by alkyl(s),
$R^{13}$ is
  (1) a $C_1$-$C_6$ alkyl optionally substituted by group(s) selected from the group consisting of the following (i) to (xiv):
  (i) a $C_5$-$C_7$ cycloalkyl optionally substituted by group(s) selected from the group consisting of the following a) to e):
  a) hydroxy
  b) an amino optionally substituted by $C_1$-$C_4$ alkyl(s),
  c) a $C_1$-$C_4$ alkanoylamino,
  d) a $C_1$-$C_4$ alkyl optionally substituted by group(s) selected from the group consisting of hydroxy, amino, and a carbamoyl optionally substituted by $C_1$-$C_4$ alkyl(s), and
  e) a carbamoyl optionally substituted by $C_1$-$C_4$ alkyl(s),
  (ii) hydroxy,
  (iii) a carbamoyl optionally substituted by $C_1$-$C_4$ alkyl(s),
  (iv) a piperidyl optionally substituted by group(s) selected from the group consisting of an alkyl, an alkanoyl, an alkylsulfonyl and oxo,
  (v) a pyrrolidinyl optionally substituted by group(s) selected from the group consisting of an alkyl, an alkanoyl, an alkylsulfonyl and oxo,
  (vi) a tetrahydropyranyl optionally substituted by hydroxy(s),
  (vii) an imidazolinyl optionally substituted by group(s) selected from the group consisting of an ailcyl and oxo,
  (viii) an imidazolidinyl optionally substituted by group(s) selected from the group consisting of an alkyl and oxo,
  (ix) a piperadinyl optionally substituted by group(s) selected from the group consisting of an alkyl and oxo,
  (x) a hexahydropyrimidinyl optionally substituted by group(s) selected from the group consisting of an alkyl and oxo,
  (xi) a pyridyl optionally substituted by alkyl(s),
  (xii) furyl,
  (xiii) tetrahydroisothiazolyl optionally substituted by oxo(s), and
  (xiv) an amino optionally substituted by the group(s) selected from alkanoyl(s) and alkylsulfonyl(s),
  (2) a $C_5$-$C_7$ cycloalkyl optionally substituted by group(s) selected from the group consisting of the following (i) to (v):
  (i) hydroxy,
  (ii) a $C_1$-$C_4$ alkoxy,
  (iii) a $C_1$-$C_4$ alkyl optionally substituted by group(s) selected from the group consisting of hydroxy, amino and a carbamoyl optionally substituted by $C_1$-$C_4$ alkyl(s),
  (iv) a carbamoyl optionally substituted by $C_1$-$C_4$ alkyl(s), and
  (v) an amino optionally substituted by group(s) selected from the group consisting of $C_1$-$C_4$ alkyl(s) and $C_1$-$C_4$ alkylsulfonyl(s), or
  (3) a heterocyclic group optionally substituted by group(s) selected from the group consisting of the following (i) to (vii):
  (i) an alkyll optionally substituted by group(s) selected from the group consisting of a halogen, amino, hydroxy, phenyl and oxo,
  (ii) an aminosulfonyl optionally substituted by alkyl(s),
  (iii) an alkylisulfonyl optionally substituted by halogen(s),
  (iv) a carbamoyl optionally substituted by alkyl(s),
  (v) hydroxy,
  (vi) an alkoxycarbonyl, and
  (vii) oxo,
or a pharmaceutically acceptable salt thereof.

13. The compound according to claim 12, wherein
$R^{12}$ is
  (1) a $C_1$-$C_5$ alkyl optionally substituted by group(s) selected from the group consisting of hydroxy, alkoxy, tetrahydropyranyl and tetrahydrofliryl,
  (2) a $C_3$-$C_4$ cycloalkylmethyl,
  (3) a $C_3$-$C_4$ cycloalkyl,
  (4) carbamoylmethyl,
  (5) a benzyl optionally substituted by group(s) selected from the group consisting of cyano, a halogen atom, a $C_1$-$C_3$ alkoxy, a $C_1$-$C_3$ alkyl and a halogen-substituted $C_1$-$C_3$ alkyl,
  (6) tetrahydropyranyl,
  (7) tetrahydrofuryl, or
  (8) a piperidyl optionally substituted by alkylsulfonyl or alkanoyl,
$R^{13}$ is
  (1) a $C_1$-$C_6$ alkyl optionally substituted by group(s) selected from the group consisting of the following (i) to (iv):
  (i) a $C_5$-$C_7$ cycloalkyl optionally substituted by group(s) selected from the group consisting of the following a) to e):
  a) hydroxy
  b) an amino optionally substituted by $C_1$-$C_4$ alkyl(s),
  c) a $C_1$-$C_4$ alkanoylamino, d) a $C_1$-$C_4$ alkyl optionally substituted by group(s) selected from the group consisting of hydroxy, amino, and a carbamoyl optionally substituted by $C_1$-$C_4$ alkyl(s), and
e) a carbamoyl optionally substituted by $C_1$-$C_4$ alkyl(s),
   (ii) hydroxy,
   (iii) a carbamoyl optionally substituted by $C_1$-$C_4$ alkyl(s), and
   (iv) amino optionally substituted by the group(s) selected from alkanoyl(s) and alkylsulfonyl(s),
(2) a $C_5$-$C_7$ cycloalkyl optionally substituted by group(s) selected from the group consisting of the following (i) to (v):
   (i) hydroxy,
   (ii) a $C_1$-$C_4$ alkoxy
   (iii) a $C_1$-$C_4$ alkyl optionally substituted by group(s) selected from the group consisting of hydroxy, amino and a carbamoyl optionally substituted by $C_1$-$C_4$ alkyl(s),
   (iv) a carbamoyl optionally substituted by $C_1$-$C_4$ alkyl(s), and
   (v) an amino optionally substituted by group(s) selected from the group consisting of $C_1$-$C_4$ alkyl(s) and $C_1$-$C_4$ alkylsulfonyl(s), or
(3) a heterocyclic group optionally substituted by group(s) selected from the group consisting of the following (i) to (vi):
   (i) alkylsulfonyl(s),
   (ii) alkoxycarbonyl(s),
   (iii) carbamoyl(s) optionally substituted by alkyl(s),
   (iv) alkanoyl(s),
   (v) aminosulfonyl(s) optionally substituted by alkyl(s), and
   (vi) alkyl(s)
or a pharmaceutically acceptable salt thereof.

14. The compound according to claim 13, wherein $R^{11}$ is a group selected from the group consisting of hydrogen atom, fluorine atom, chlorine atom, methyl, trifluoromethyl and methoxy,
   k is 1 or 2, and when k is 2, two of $R^{11}$s may be the same or different,
   $R^{12}$ is a $C_1$-$C_5$ alkyl optionally substituted by hydroxy, cyclopropylmethyl, cyclobutyl, carbamoylmethyl, tetrahydropyranyl, tetrahydrofuryl, tetrahydropyranylinethyl, tetrahydrofurylmethyl or piperidyl optionally substituted by the group selected from alkylsulfonyl and alkanoyl,
or a pharmaceutically acceptable salt thereof.

15. The compound according to claim 13, wherein $R^{11}$ is hydrogen atom, fluorine atom, chlorine atom, trifluoromethyl or methyl,
   k is 1,
   $R^{12}$ ethyl, isopropyl, isobutyl, 2-hydroxy-2-methylpropyl, cyclopropylmethyl, cyclobutyl, carbamoylmethyl,4-tetrahydropyranyl, 3-tetrahydrofuryl, tetrahydropyranylmethyl, tetrahydrofurylmethyl , methoxymethyl, 3-hydroxy-3-methylbutyl or 4-piperidyl substituted by methanesulfonyl or acetyl, $R^{13}$ is
   (1) a $C_1$-$C_6$ alkyl optionally substituted by group(s) selected from the group consisting of the following (i) and (iii):
   (i) a $C_5$-$C_7$ cycloalkyl optionally substituted by group(s) selected from the group consisting of hydroxy, a hydroxy $C_1$-$C_4$ alkyl, a $C_1$-$C_4$ alkyl, amino and a carbamoyl optionally substituted by $C_1$-$C_4$ alkyl(s),
   (ii) hydroxy, and
   (iii) an amino optionally substituted by group(s) selected from the group consisting of alkyl(s) and alkylsulfonyl(s),
(2) a $C_5$-$C_7$ cycloalkyl optionally substituted by group(s) selected from the group consisting of the following (i) to (v):
   (i) hydroxy,
   (ii) a $C_1$-$C_4$ alkoxy
   (iii) a $C_1$-$C_4$ alkyl optionally substituted by group(s) selected from the group consisting of hydroxy, amino and a carbamoyl optionally substituted by $C_1$-$C_4$ alkyl(s),
   (iv) a carbamoyl optionally substituted by $C_1$-$C_4$ alkyl(s), and
   (v) an amino optionally substituted by group(s) selected from the group consisting of alkyl(s) and alkylsulfonyl(s),
(3) piperidinyl optionally substituted by group(s) selected from the group consisting of the following (i) to (vi):
   (i) alkylsulfonyl(s),
   (ii) alkoxycarbonyl(s),
   (iii) carbamoyl(s) optionally substituted by alkyl(s),
   (iv) alkanoyl(s),
   (v) aminosulfonyl(s) optionally substituted by alkyl(s), and
   (vi) alkyl(s)
(4) pirrolidinyl optionally substituted by alkylsulfonyl,
or a pharmaceutically acceptable salt thereof.

16. A pharmaceutical composition comprising the compound according to any one of claims 1 to 15 or a pharmaceutically acceptable salt thereof and a pharmaceutically acceptable carrier.

17. A method of treatment for diseases selected from the group consisting of rheumatoid arthritis, osteoarthritis, gouty arthritis, synovitis, ulcerative colitis, Crohn's disease, psoriasis, atopic dermatitis, contact dermatitis, asthma, bronchitis, pneumonia, pleurisy, rhinitis, conjunctivitis, keratitis, uveitis, nephritis, hepatitis, Beheet's syndrome, Systemic lupus erythematosus, septic shock, brain hemorrhage, ischemic heart disease, congestive heart failure, osteoporosis, diabetes, cachexia, Alzheimer's disease, Parkinson's disease, arterial sclerosis, and disseminated intravascular coagulation syndrome, which comprises administering the compound according to any one of claims 1 to 15 or a pharmaceutically acceptable salt thereof to a human in need thereof.

* * * * *